(12) United States Patent
 Hamersky et al.

(10) Patent No.: US 12,371,820 B2
(45) Date of Patent: Jul. 29, 2025

(54) NATURAL POLYMER-BASED FIBROUS ELEMENTS COMPRISING A SURFACTANT AND METHODS FOR MAKING SAME

(71) Applicant: The Procter & Gamble Company, Cincinnati, OH (US)

(72) Inventors: Mark William Hamersky, Hamilton, OH (US); Mark Robert Sivik, Mason, OH (US); John David Sadler, Cincinnati, OH (US); Luke Andrew Zannoni, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 358 days.

(21) Appl. No.: 17/824,529

(22) Filed: May 25, 2022

(65) Prior Publication Data
US 2022/0403558 A1    Dec. 22, 2022

Related U.S. Application Data

(60) Provisional application No. 63/194,335, filed on May 28, 2021.

(51) Int. Cl.
 *D01F 9/00* (2006.01)
 *C08L 3/04* (2006.01)
(52) U.S. Cl.
 CPC .  *D01F 9/00* (2013.01); *C08L 3/04* (2013.01)
(58) Field of Classification Search
 CPC ..................................... D01F 9/00; C08L 3/04
 See application file for complete search history.

(56) References Cited

U.S. PATENT DOCUMENTS

| 2016/0101026 | A1  | 4/2016 | Pratt et al. |
| 2018/0209101 | A1* | 7/2018 | Cabell ...................... D21F 11/16 |
| 2020/0093711 | A1* | 3/2020 | Hamersky ............ A61K 8/0279 |
| 2021/0030632 | A1  | 2/2021 | Wei et al. |
| 2021/0032572 | A1  | 2/2021 | Aouad et al. |

FOREIGN PATENT DOCUMENTS

| WO | 2005061763 A1 | 7/2005 |
| WO | 2012003307 A2 | 1/2012 |
| WO | 2013126492 A1 | 8/2013 |
| WO | 2013126531 A1 | 8/2013 |
| WO | 2016057353 A1 | 4/2016 |
| WO | 2021022306 A1 | 2/2021 |
| WO | 2021026556 A1 | 2/2021 |
| WO | 2022251838 A1 | 12/2022 |

OTHER PUBLICATIONS

Yu et al., "Effects of native starch and modified starches on the textural, rheological and microstructural characteristics of soybean protein gel," International Journal of Biological Macromolecules 142 (2020) 237-243. (Year: 2020).*
PCT Search Report and Written Opinion for PCT/US2022/072548 dated Sep. 14, 2022,11 pages.

* cited by examiner

*Primary Examiner* — Jeremy R Pierce
(74) *Attorney, Agent, or Firm* — James E. Oehlenschlager

(57) ABSTRACT

Natural polymer-based fibrous elements including a modified polymer derived from a natural polymer and a surfactant, method for making such natural polymer-based fibrous elements and methods for making such fibrous structures are provided.

12 Claims, 8 Drawing Sheets

NATURAL POLYMER-BASED FIBROUS ELEMENTS COMPRISING A SURFACTANT AND METHODS FOR MAKING SAME

FIELD OF THE INVENTION

The present invention relates to natural polymer-based fibrous elements comprising a modified polymer derived from a natural polymer and a surfactant, and more particularly to natural polymer-based fibrous elements comprising a modified polysaccharide, for example an acetylated polysaccharide, such as acetylated starch, and a surfactant, for example an anionic surfactant, methods for making such natural polymer-based fibrous elements, fibrous structures made from such natural polymer-based fibrous elements, and methods for making such fibrous structures.

BACKGROUND OF THE INVENTION

Polyvinyl alcohol ("PVOH"), a synthetic polymer produced from polyvinyl acetate, is a workhorse filament-forming material (for example a structurant) for making fibrous elements, for example filaments and/or fibers, especially in nonwoven (fibrous structure) making processes. PVOH is available in a wide range of weight average molecular weights. It is easily processed via extrusion processing (for example a continuous extrusion process) and/or batch processing. PVOH is strong, but flexible due to its Tg, which is about 80-85° C. It also exhibits excellent miscibility across a wide range of surfactants. Many of the PVOH grades are biodegradable.

With the current interest in natural materials and products, formulators have been exploring possible replacements for PVOH with a natural polymer, for example a polysaccharide such as starch. However, current polysaccharides, such as starch, are less compatible with surfactants, for example high levels of surfactants, than PVOH. Further, in order to make a polysaccharide such as starch function more like PVOH, better compatibility with surfactants, in particular high levels of surfactants, less hydrogen bonding, lower Tg, and/or more hydrophobicity of the polysaccharide, especially starch, will be needed.

Derivatives of starch may provide starch with properties more similar to PVOH. For example, acetylated starch is one starch derivative that shows promise. Acetylated starches are known in the art. Such known acetylated starches have been made with various degrees of substitution (DS) ranging from 0.1 to 3. Further, Food & Drug Administration currently requires acetylated starches, for example used in foods, to have less than 2.5% acetyl groups (a DS of less than 0.1).

There is a need for a natural polymer-based material, for example a polysaccharide-based material, such as a starch-based material, for example a starch derivative, for example a modified polysaccharide and/or modified starch, that exhibits properties, for example Tg, hydrophobicity, less hydrogen bonding, and/or better compatibility with surfactants, especially higher levels of surfactants than is currently achievable, for example that can be used as a replacement for PVOH, fibrous elements, for example water soluble fibrous elements, made from such natural polymer-based material, fibrous structures made from such natural polymer-based fibrous elements, and methods for making the natural polymer-based material, natural polymer-based fibrous elements, and fibrous structure.

Although fibrous elements, namely crosslinked, water insoluble fibrous elements, and fibrous structures comprising such fibrous elements have been made using starch and/or starch derivatives, such as ethoxylated starches, such fibrous elements and fibrous structures have been limited to low surfactant levels (less than 1:1 weight ratio of surfactant to starch). Further, unlike polyvinyl alcohol, especially polyvinyl alcohol having a specific degree of hydrolysis (about 84-87% hydrolysis), which has been made into a high surfactant-containing (greater than 1:1 weight ratio of surfactant to polyvinyl alcohol) aqueous fibrous element-forming composition that is then spun into water soluble fibrous elements since the aqueous fibrous element-forming composition's polyvinyl alcohol is miscible with the high level surfactant and high solids levels (for example greater than 15% and/or greater than 20% and/or at least 25% by weight), starch to date has not been as successful. In fact, when utilizing unmodified starch (regardless of amylose to amylopectin ratio), at similarly high surfactant levels (for example greater than 0.15:1 and/or greater than 0.20:1 and/or greater than 0.25:1 and/or greater than 0.5:1 and/or greater than 1:1 weight ratio of surfactant to starch) and high solids levels (greater than 15% and/or greater than 20% and/or at least 25% by weight), an immiscible aqueous fibrous element-forming composition results, making conversion to a fibrous element, for example a water soluble fibrous element, difficult if not impossible.

Since unmodified polysaccharides, namely unmodified starch has not been successful, starch derivatives have been explored. Starch derivatives that are commercially available for food use, such as acetylated starch with a maximum 2.5% acetyl groups (DS less than 0.1) have been tried by formulators, but they too are not compatible with high levels of surfactants (for example greater than 0.15:1 and/or greater than 0.20:1 and/or greater than 0.25:1 and/or greater than 0.5:1 and/or greater than 1:1 weight ratio of surfactant to acetylated starch) and thus result in phase separation of the surfactant and acetylated starch, which causes failure or less than satisfactory spun fibrous elements.

In light of the foregoing, there is a need for a natural polymer-based material, for example a modified polysaccharide, such as a starch derivative, that is suitable for combining with high levels of surfactant to produce spun natural polymer-based fibrous elements, for example "meltblown" spun natural polymer-based fibrous elements, that contain a weight ratio of surfactant to natural polymer-based material of greater than 0.15:1 and/or greater than 0.20:1 and/or greater than 0.25:1 and/or greater than 0.5:1 and/or greater than 1:1, fibrous structures made from such natural polymer-based fibrous elements and methods for making the same.

SUMMARY OF THE INVENTION

The present invention fulfills the need described above by providing a natural polymer-based material that is suitable for combining with high levels of surfactant to produce spun natural polymer-based fibrous elements, for example "meltblown" spun natural polymer-based fibrous elements, that contain a weight ratio of surfactant to natural polymer-based material, for example a modified polysaccharide, such as a starch derivative, for example an acetylated starch, of greater than 0.15:1 and/or greater than 0.20:1 and/or greater than 0.25:1 and/or greater than 0.5:1 and/or greater than 1:1 and/or to about to about 6:1 or to about 5.5:1 or to about 5:1, fibrous structures made from such natural polymer-based fibrous elements, methods for making the same, a fibrous element-forming composition comprising a natural polymer-based fibrous element-forming material, for example a modified polysaccharide, such as a starch derivative, for example an acetylated starch, and a surfactant, which can be spun into the natural polymer-based fibrous elements of the present invention.

To solve this problem, chemical modification of a natural polymer, for example a polysaccharide, such as a starch, such that the natural polymer can be used as a natural polymer-based fibrous element-forming material is needed. Such a natural polymer-based fibrous element-forming material, for example a modified polysaccharide, such as a starch derivative, for example an acetylated starch, can be combined with a surfactant, for example a high level of surfactant, to form an aqueous natural polymer-based fibrous element-forming composition that is suitable for spinning natural polymer-based fibrous elements according to the present invention. The specific natural polymer, for example polysaccharide, such as starch, chemical modification type and modification level can be approximated by calculating a solubility parameter using the "Fedors Method" as described in Robert F. Fedors' A Method for Estimating Both the Solubility Parameters and Molar Volumes of Liquids. POLYMER ENGINEERING AND SCIENCE, FEBRUARY, 1974, Vol. 14, No. 2, 147 (hereinafter referred to as the "Fedors Method" described herein), relevant parts of which are described hereinbelow that matches the solubility parameter of other filament-forming materials, such as PVOH (solubility parameter number 14-16), where miscible filament-forming material/surfactant aqueous formulations at high surfactant and high solids levels exist. Additionally, the natural polymer, for example polysaccharide, such as a starch, weight average molecular weight impacts miscibility in a high surfactant/high solids formulation. Therefore, the characteristics of the natural polymers of the present invention, for example polysaccharides, such as starches, weight average molecular weights, level of chemical modification, and type of chemical modification result in a natural polymer-based fibrous element-forming material that forms a miscible aqueous formulation with surfactant at high surfactant and high solids levels such that the natural polymer-based fibrous element-forming material is spinnable into a natural polymer-based fibrous element according to the present invention. For example, an unmodified starch, for example an unmodified amioca starch exhibits a solubility parameter number of 17.2, but an acetylated starch having a DS of 0.3 exhibits a solubility parameter number of 16.2 and an acetylated starch having a DS of 0.7 exhibits a solubility parameter number of 14.7.

In one example of the present invention, a fibrous element, for example a natural polymer-based fibrous element, for example a water-soluble natural polymer-based fibrous element, comprising one or more fibrous element-forming materials, for example one or more natural polymer-based fibrous element-forming materials, for example one or more water-soluble natural polymer-based fibrous element-forming materials, comprising a modified polysaccharide, for example a modified starch, such as an acetylated starch, and one or more active agents wherein at least one of the active agents comprises a surfactant, wherein the surfactant and the one or more natural polymer-based fibrous element-forming materials, for example a modified polysaccharide, are present in the natural polymer-based fibrous element at a weight ratio of from about 0.15:1 to about 6:1 and/or from about 0.20:1 to about 5.5:1 and/or from about 0.25:1 to about 5:1, is provided.

In another example of the present invention, a fibrous structure, for example a water-soluble fibrous structure, comprising a plurality of fibrous elements, for example a plurality of natural polymer-based fibrous elements, which may be inter-entangled, for example a plurality of water-soluble natural polymer-based fibrous elements, wherein the plurality of fibrous elements, for example natural polymer-based fibrous elements, comprise one or more fibrous element-forming materials, for example one or more natural polymer-based fibrous element-forming materials, for example one or more water-soluble natural polymer-based fibrous element-forming materials, at least one of the one or more fibrous element-forming materials comprising a modified polysaccharide, for example a modified starch, such as acetylated starch, and one or more active agents, for example present in and releasable from the plurality of fibrous elements, wherein at least one of the active agents comprises a surfactant, wherein the surfactant and the one or more fibrous element-forming materials, for example natural polymer-based fibrous element-forming materials, such as a modified polysaccharide, are present with the plurality of fibrous elements at a weight ratio of from about 0.15:1 to about 6:1 and/or from about 0.20:1 to about 5.5:1 and/or from about 0.25:1 to about 5:1, is provided.

In another example of the present invention, a package comprising one or more fibrous structures of the present invention is provided.

In yet another example of the present invention, a method for making one or more fibrous elements, for example one or more natural polymer-based fibrous elements, for example one or more water-soluble natural polymer-based fibrous elements, the method comprising the steps of:
a. providing a fibrous element-forming composition, for example an aqueous fibrous element-forming composition, comprising a fibrous element-forming material, for example a natural polymer-based fibrous element-forming material, for example a water-soluble natural polymer-based fibrous element-forming material, comprising a modified polysaccharide, for example a modified starch, such as acetylated starch, and one or more active agents comprising at least one surfactant, wherein the surfactant and the one or more natural polymer-based fibrous element-forming materials, for example a modified polysaccharide, are present with the plurality of fibrous elements at a weight ratio of from about 0.15:1 to about 6:1 and/or from about 0.20:1 to about 5.5:1 and/or from about 0.25:1 to about 5:1; and
b. spinning the fibrous element-forming composition into one or more natural polymer-based fibrous elements, for example one or more water-soluble natural polymer-based fibrous elements, is provided.

In another example of the present invention, a method for making a fibrous structure, for example a water-soluble fibrous structure, the method comprising the steps of:
a. providing a fibrous element-forming composition, for example an aqueous fibrous element-forming composition, comprising one or more fibrous element-forming materials, for example one or more natural polymer-based fibrous element-forming materials, for example one or more water-soluble natural polymer-based fibrous element-forming materials, comprising a modified polysaccharide, for example a modified starch, such as acetylated starch, and one or more active agents wherein at least one of the active agents comprises a surfactant, wherein the surfactant and the one or more natural polymer-based fibrous element-forming materials, for example a modified polysaccharide, are present in the fibrous element-forming composition at a weight ratio of from about 0.15:1 to about 6:1 and/or from about 0.20:1 to about 5.5:1 and/or from about 0.25:1 to about 5:1;

b. spinning the fibrous element-forming composition into a plurality of fibrous elements, for example a plurality of natural polymer-based fibrous elements, for example a plurality of water-soluble natural polymer-based fibrous elements, comprising the natural polymer-based fibrous element-forming materials and the surfactant; and c. optionally, mixing a plurality of particles, for example water-soluble and/or water-insoluble particles, for example water-soluble and/or water-insoluble active agent-containing particles, with the plurality of fibrous elements, for example natural polymer-based fibrous elements;

d. collecting the plurality of fibrous elements, for example natural polymer-based fibrous elements, which may be inter-entangled, from step (b) and/or mixture of particles and natural polymer-based fibrous elements, from optional step (c), to form a fibrous structure, for example a water-soluble fibrous structure, is provided.

In even another example, a fibrous element-forming composition comprising a polar solvent and one or more fibrous element-forming materials, for example one or more natural polymer-based fibrous element-forming materials, for example one or more water-soluble natural polymer-based fibrous element-forming materials, comprising a modified polysaccharide, for example a modified starch, such as acetylated starch, and one or more active agents wherein at least one of the active agents comprises a surfactant, wherein the surfactant and the one or more natural polymer-based fibrous element-forming materials are present within the fibrous element-forming composition at a weight ratio of from about 0.15:1 to about 6:1 and/or from about 0.20:1 to about 5.5:1 and/or from about 0.25:1 to about 5:1, is provided.

In yet another example of the present invention, a fibrous element, for example a natural polymer-based fibrous element, for example a water-soluble natural polymer-based fibrous element, wherein the fibrous element comprise one or more fibrous element-forming materials, for example one or more natural polymer-based fibrous element-forming materials, for example one or more water-soluble natural polymer-based fibrous element-forming materials, for example a modified polysaccharide, for example a modified starch, such as an acetylated starch having a degree of substitution (DS) of from about 0.1 to about 1.0 and/or from about 0.2 to about 0.9 and/or from about 0.2 to about 0.8 and/or from about 0.3 to about 0.7 and/or from about 0.3 to about 0.5, a weight average molecular weight (Mw) of from about 25,000 to about 450,000 g/mol and/or from about 35,000 to about 400,000 g/mol and/or from about 50,000 to about 400,000 g/mol and/or from about 60,000 to about 400,000 g/mol and/or from about 65,000 to about 350,000 g/mol and/or from about 70,000 to about 300,000 g/mol and/or from about 90,000 to about 300,000 g/mol and/or from about 120,000 to about 250,000 g/mol and/or from about 130,000 to about 250,000 g/mol and/or from about 150,000 to about 250,000 g/mol as measured according to the Weight Average Molecular Weight Test Method described herein, wherein the fibrous element further comprises a one or more active agents, for example one or more surfactants, such as a surfactant mixture comprising a linear alkyl benzene sulfonate and an alkyl sulfate, wherein the fibrous element is derived from a fibrous element-forming composition, for example an aqueous fibrous element-forming composition, exhibiting a viscosity of from about 0.01 Pas to about 1.2 Pas and/or from about 0.02 Pas to about 1.0 Pas as measured according to the Rotational Rheometer Test Method described herein, wherein the fibrous element-forming composition comprises the surfactant mixture and the one or more fibrous element-forming materials, for example one or more natural polymer-based fibrous element-forming materials, for example modified polysaccharide, such as modified starch, for example acetylated starch, at a weight ratio of from about 0.15:1 to about 6:1 and/or from about 0.20:1 to about 5.5:1 and/or from about 0.25:1 to about 5:1 and/or from about 0.5:1 to about 2:1, wherein the fibrous element-forming composition further comprises from about 55% to about 85% by weight of water, is provided.

In another example of the present invention, a fibrous structure, for example a water-soluble fibrous structure, comprising a plurality of fibrous elements, for example a plurality of natural polymer-based fibrous elements, for example a plurality of water-soluble natural polymer-based fibrous elements, wherein the plurality of fibrous elements comprise one or more fibrous element-forming materials, for example one or more natural polymer-based fibrous element-forming materials, for example one or more water-soluble natural polymer-based fibrous element-forming materials, for example a modified polysaccharide, for example a modified starch, such as an acetylated starch having a DS of from about 0.1 to about 1.0 and/or from about 0.2 to about 0.9 and/or from about 0.2 to about 0.8 and/or from about 0.3 to about 0.7 and/or from about 0.3 to about 0.5, a weight average molecular weight (Mw) of from about 25,000 to about 450,000 g/mol and/or from about 35,000 to about 400,000 g/mol and/or from about 50,000 to about 400,000 g/mol and/or from about 60,000 to about 400,000 g/mol and/or from about 65,000 to about 350,000 g/mol and/or from about 70,000 to about 300,000 g/mol and/or from about 90,000 to about 300,000 g/mol and/or from about 120,000 to about 250,000 g/mol and/or from about 130,000 to about 250,000 g/mol and/or from about 150,000 to about 250,000 g/mol as measured according to the Weight Average Molecular Weight Test Method described herein, wherein the plurality of fibrous elements further comprise one or more active agents, for example one or more surfactants, such as a surfactant mixture comprising a linear alkyl benzene sulfonate and an alkyl sulfate, wherein the plurality of fibrous elements is derived from a fibrous element-forming composition, for example an aqueous fibrous element-forming composition, exhibiting a viscosity of from about 0.01 Pas to about 1.2 Pas and/or from about 0.02 Pas to about 1.0 Pas as measured according to the Rotational Rheometer Test Method described herein, wherein the fibrous element-forming composition comprises the surfactant mixture and the one or more natural polymer-based fibrous element-forming materials, for example modified polysaccharide, such as modified starch, for example acetylated starch, at a weight ratio of from about 0.15:1 to about 6:1 and/or from about 0.20:1 to about 5.5:1 and/or from about 0.25:1 to about 5:1 and/or from about 0.5:1 to about 2:1, wherein the fibrous element-forming composition further comprises from about 55% to about 85% by weight of water, is provided.

In yet another example of the present invention, a fibrous element-forming composition, for example an aqueous fibrous element-forming composition, for example a natural polymer-based fibrous element-forming composition comprising a polar solvent and one or more fibrous element-forming materials, for example one or more natural polymer-based fibrous element-forming materials, for example a modified polysaccharide, such as a modified starch, for example acetylated starch, and one or more active agents, for example one or more surfactants, such as a surfactant mixture comprising a linear alkyl benzene sulfonate and an alkyl sulfate such that the natural polymer-based fibrous element-forming composition exhibits a viscosity of from about 0.01 Pas to about 1.2 Pas and/or from about 0.02 Pas to about 1.0 Pas as measured according to the Rotational Rheometer Test Method described herein, is provided.

In still yet another example of the present invention, a method for making a fibrous element, for example a natural polymer-based fibrous element, for example a water-soluble natural polymer-based fibrous element, the method comprises the steps of:
 a. providing a fibrous element-forming composition, for example a water-soluble fibrous element-forming composition, comprising one or more fibrous element-forming materials, for example one or more natural polymer-based fibrous element-forming materials, for example a modified polysaccharide, such as a modified starch, for example acetylated starch, and a surfactant mixture, for example a surfactant mixture comprising a linear alkyl benzene sulfonate and an alkyl sulfate, wherein the fibrous element-forming composition comprises the surfactant mixture and the one or more natural polymer-based fibrous element-forming materials at a weight ratio of from about 0.15:1 to about 6:1 and/or from about 0.20:1 to about 5.5:1 and/or from about 0.25:1 to about 5:1 and/or from about 0.5:1 to about 2:1;
 b. spinning the fibrous element-forming composition into one or more fibrous elements, for example one or more natural polymer-based fibrous elements comprising the one or more fibrous element-forming materials, for example one or more natural polymer-based fibrous element-forming materials and the surfactant mixture, is provided.

In yet another example of the present invention, a fibrous element comprising one or more fibrous element-forming materials comprising an acetylated starch having a degree of substitution (DS) of from about 0.3 to about 0.7, a weight average molecular weight of from about 50,000 to about 250,000 g/mol, wherein the fibrous element further comprises a surfactant mixture comprising a linear alkyl benzene sulfonate and an alkyl sulfate, wherein the aqueous composition comprises the surfactant mixture and the acetylated starch at a weight ratio of from about 0.5:1 to about 2:1, wherein the aqueous composition further comprises from about 55% to about 85% by weight of water is provided.

In still another example of the present invention, a fibrous structure comprising a plurality of fibrous elements according to the present invention, wherein the fibrous structure comprises the surfactant mixture and the acetylated starch at a weight ratio of from about 0.5:1 to about 2:1.

In even another example of the present invention, a method for making a fibrous element, the method comprises the steps of:
 a. providing a fibrous element-forming composition comprising one or more fibrous element-forming materials comprising an acetylated starch and a surfactant mixture comprising a linear alkyl benzene sulfonate and an alkyl sulfate, wherein the fibrous element-forming composition comprises the surfactant mixture and the acetylated starch at a weight ratio of from about 0.5:1 to about 2:1; and
 b. spinning the fibrous element-forming composition into one or more fibrous elements comprising the acetylated starch and the surfactant mixture is provided.

In even yet another example of the present invention, a fibrous element-forming composition comprising a polar solvent and one or more fibrous element-forming materials comprising an acetylated starch and a surfactant mixture comprising a linear alkyl benzene sulfonate and an alkyl sulfate such that the fibrous element-forming composition exhibits a viscosity of from about 0.01 Pas to about 1.2 Pas as measured according to the Rotational Rheometer Test Method is provided.

The present invention provides natural polymer-based fibrous elements, fibrous structures comprising a plurality of natural polymer-based fibrous elements, fibrous element-forming compositions comprising natural polymer-based fibrous element-forming materials, natural polymer-based fibrous element-forming materials, and methods for making same.

DETAILED DESCRIPTION OF THE INVENTION

Definitions

Figure 1:
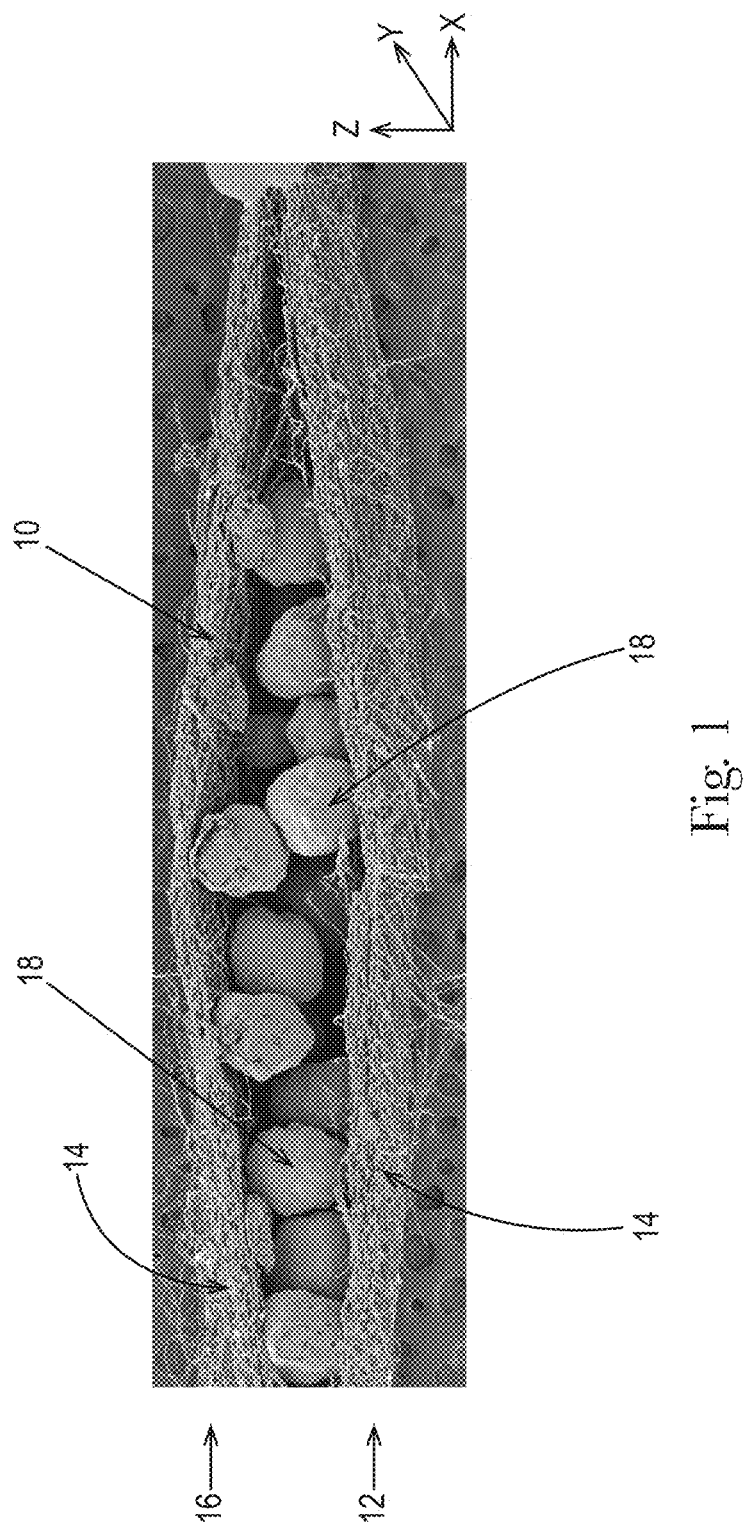
FIG. 1 is a scanning electron microscope photograph of a cross-sectional view of an example of a fibrous structure according to the present invention.

"Fibrous structure" as used herein means a structure that comprises one or more fibrous elements and optionally, one or more particles. In one example, a fibrous structure according to the present invention means an association of fibrous elements and optionally, particles, that together form a structure, such as a unitary structure, capable of performing a function. A plurality of fibrous elements may be inter-entangled.

The fibrous structures of the present invention may be homogeneous or may be layered. If layered, the fibrous structures may comprise at least two and/or at least three and/or at least four and/or at least five layers, for example one or more fibrous element layers, one or more particle layers, when present, and/or one or more fibrous element/particle mixture layers, when particles are present.

In one example, the fibrous structure is a multi-ply fibrous structure that exhibits a basis weight of less than 5000 g/m$^2$ as measured according to the Basis Weight Test Method described herein.

In one example, the fibrous structure of the present invention is a "unitary fibrous structure."

"Unitary fibrous structure" as used herein is an arrangement comprising a plurality of fibrous elements that are inter-entangled or otherwise associated with one another to form a fibrous structure. A unitary fibrous structure may further comprise in addition to the plurality of fibrous elements, one or more and/or a plurality of particles associated with the plurality of fibrous elements. A unitary fibrous structure of the present invention may be one or more plies within a multi-ply fibrous structure. In one example, a unitary fibrous structure of the present invention may comprise three or more different fibrous elements. In another example, a unitary fibrous structure of the present invention may comprise two different fibrous elements, for example a co-formed fibrous structure, upon which a different fibrous element is deposited to form a fibrous structure comprising three or more different fibrous elements.

"Fibrous element" as used herein means an elongate particulate having a length greatly exceeding its average diameter, i.e. a length to average diameter ratio of at least about 10. A fibrous element may be a filament or a fiber. In one example, the fibrous element is a single fibrous element rather than a yarn comprising a plurality of fibrous elements.

The fibrous elements of the present invention may be spun from a filament-forming composition also referred to as a fibrous element-forming composition via suitable spinning process operations, such as meltblowing, spunbonding, electro-spinning, and/or rotary spinning.

The fibrous elements of the present invention may be monocomponent and/or multicomponent. For example, the fibrous elements may comprise bicomponent fibers and/or filaments. The bicomponent fibers and/or filaments may be in any form, such as side-by-side, core and sheath, islands-in-the-sea and the like.

"Filament" as used herein means an elongate particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments.

"Fiber" as used herein means an elongate particulate as described above that exhibits a length of less than 5.08 cm (2 in.) and/or less than 3.81 cm (1.5 in.) and/or less than 2.54 cm (1 in.).

Fibers are typically considered discontinuous in nature. Non-limiting examples of fibers include staple fibers produced by spinning a filament or filament tow of the present invention and then cutting the filament or filament tow into segments of less than 5.08 cm (2 in.) thus producing fibers.

In one example, one or more fibers may be formed from a filament of the present invention, such as when the filaments are cut to shorter lengths (such as less than 5.08 cm in length). Thus, in one example, the present invention also includes a fiber made from a filament of the present invention, such as a fiber comprising one or more filament-forming materials and one or more additives, such as active agents. Therefore, references to filament and/or filaments of the present invention herein also include fibers made from such filament and/or filaments unless otherwise noted. Fibers are typically considered discontinuous in nature relative to filaments, which are considered continuous in nature.

"Filament-forming composition" and/or "fibrous element-forming composition" as used herein means a composition that is suitable for making one or more fibrous elements of the present invention such as by meltblowing and/or spunbonding, for example by spinning fibrous elements from a multi-row capillary meltblow die. The filament-forming composition comprises one or more fibrous element-forming materials, for example filament-forming materials, that exhibit properties that make them suitable for spinning into a fibrous element. In one example, the fibrous element-forming material comprises a polymer. In addition to one or more fibrous element-forming materials, the fibrous element-forming composition may comprise one or more additives, for example one or more active agents. In addition, the fibrous element-forming composition may comprise one or more polar solvents, such as water, into which one or more, for example all, of the fibrous element-forming materials and/or one or more, for example all, of the active agents are dissolved and/or dispersed prior to spinning a fibrous element, such as a filament from the fibrous element-forming composition.

In one example, a fibrous element, for example filament, of the present invention made from a fibrous element-forming composition of the present invention is such that one or more additives, for example one or more active agents, may be present in the fibrous element rather than on the fibrous element, such as a coating composition comprising one or more active agents. The one or more active agents within such a coating composition may be the same or different from the active agents in the fibrous elements and/or active agent-containing particles, if present. The total level of fibrous element-forming materials and total level of active agents present in the fibrous element-forming composition may be any suitable amount so long as the fibrous elements of the present invention are produced therefrom.

In one example, one or more additives, such as active agents, may be present in the fibrous element and one or more additional additives, such as active agents, may be present on a surface of the fibrous element. In another example, a fibrous element of the present invention may comprise one or more additives, such as active agents, that are present in the fibrous element when originally made, but then bloom to a surface of the fibrous element prior to and/or when exposed to conditions of intended use of the fibrous element and/or are released from the fibrous element, for example upon dissolution, when exposed to conditions of intended use.

"Fibrous element-forming material" and/or "Filament-forming material" and/or "Fiber-forming material" as used herein means a material, such as a polymer or monomers capable of producing a polymer that exhibits properties suitable for making a fibrous element. In one example, the fibrous element-forming material comprises one or more natural polymer-based polymers such as an anionic, cationic, zwitterionic, and/or nonionic polymer. In another example, the polymer may comprise a hydroxyl polymer, for example a modified polysaccharide, for example a modified starch, such as acetylated starch. In yet another example, the natural polymer-based fibrous element-forming material, for example the modified polysaccharide is a polar solvent-soluble, for example water-soluble, natural polymer-based material.

"Commingled" and/or "commingling" as used herein means the state or form where particles are mixed with fibrous elements, for example filaments. The mixture of fibrous elements, for example filaments, and particles, for example active agent-containing particles, can be in and/or throughout a composite structure or within a plane or a region of the composite structure. In one example, the commingled fibrous elements, for example filaments, and particles may form at least a surface of a composite structure. In one example, the particles may be homogeneously dispersed in and/or throughout the composite structure and/or plane and/or region of the composite structure. In one example, the particles may be homogeneously distributed in and/or throughout a composite structure, which avoids and/or prevents sag and/or free movement and/or migration of the particles within the composite structure to other areas within the composite structure thus resulting in higher concentrated zones of particles and lower concentrated zones or zero concentration zones of particles within the composite structure. In one example, µCT cross-sections of a composite structure can show whether the particles are homogeneously distributed in and/or throughout a composite structure.

"Additive" as used herein means any material present in the fibrous element of the present invention that is not a fibrous element-forming material. In one example, an additive comprises an active agent. In another example, an additive comprises a processing aid. In still another example, an additive comprises a filler. In one example, an additive comprises any material present in the fibrous element that its absence from the fibrous element would not result in the fibrous element losing its fibrous element structure, in other words, its absence does not result in the fibrous element losing its solid form. In another example, an additive, for example an active agent, comprises a non-polymer material.

In another example, an additive may comprise a plasticizer for the fibrous element. Non-limiting examples of suitable plasticizers for the present invention include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexanediol, 2,2,4-trimethylpentane-1,3-diol, polyethylene glycol (200-600), pentaerythritol, sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, high fructose corn syrup solids, and dextrins, and ascorbic acid.

In one example, the plasticizer includes glycerin and/or propylene glycol and/or glycerol derivatives such as propoxylated glycerol. In still another example, the plasticizer is selected from the group consisting of: glycerin, ethylene glycol, polyethylene glycol, propylene glycol, glycidol, urea, sorbitol, xylitol, maltitol, sugars, ethylene bis-formamide, amino acids, and mixtures thereof In another example, an additive may comprise a rheology modifier, such as a shear modifier and/or an extensional modifier. Non-limiting examples of rheology modifiers include but not limited to polyacrylamide, polyurethanes, polyethylene oxide, polyvinyl pyrrolidone, polyvinyl caprolactam, polyvinyl imidazole, high molecular weight polysaccharides, polyvinyl alcohol, polyacrylates, and mixtures thereof that may be used in the fibrous elements of the present invention. Non-limiting examples of rheology modifiers are commercially available from The Dow Chemical Company (Midland, MI).

In yet another example, an additive may comprise one or more colors and/or dyes that are incorporated into the fibrous elements of the present invention to provide a visual signal when the fibrous elements are exposed to conditions of intended use and/or when an active agent is released from the fibrous elements and/or when the fibrous element's morphology changes.

In still yet another example, an additive may comprise one or more release agents and/or lubricants. Non-limiting examples of suitable release agents and/or lubricants include fatty acids, fatty acid salts, fatty alcohols, fatty esters, sulfonated fatty acid esters, fatty amine acetates, fatty amide, silicones, aminosilicones, fluoropolymers, and mixtures thereof. In one example, the release agents and/or lubricants may be applied to the fibrous element, in other words, after the fibrous element is formed. In one example, one or more release agents/lubricants may be applied to the fibrous element prior to collecting the fibrous elements on a collection device to form a fibrous structure. In another example, one or more release agents/lubricants may be applied to a fibrous structure formed from the fibrous elements of the present invention prior to contacting one or more fibrous structures, such as in a stack of fibrous structures. In yet another example, one or more release agents/lubricants may be applied to the fibrous element of the present invention and/or fibrous structure comprising the fibrous element prior to the fibrous element and/or fibrous structure contacting a surface, such as a surface of equipment used in a processing system so as to facilitate removal of the fibrous element and/or fibrous structure and/or to avoid layers of fibrous elements and/or plies of fibrous structures of the present invention sticking to one another, even inadvertently. In one example, the release agents/lubricants comprise particles.

In even still yet another example, an additive may comprise one or more anti-blocking and/or detackifying agents. Non-limiting examples of suitable anti-blocking and/or detackifying agents include starches, starch derivatives, crosslinked polyvinylpyrrolidone, crosslinked cellulose, microcrystalline cellulose, silica, metallic oxides, calcium carbonate, talc, mica, and mixtures thereof.

In one example, it has unexpectedly been found that the inclusion of silica in the fibrous structures of the present invention results in a stable foam with greater foam height then without the inclusion of silica.

"Conditions of intended use" as used herein means the temperature, physical, chemical, and/or mechanical conditions that a fibrous element and/or particle and/or fibrous structure of the present invention is exposed to when the fibrous element and/or particle and/or fibrous structure is used for one or more of its designed purposes. For example, if a fibrous element and/or a particle and/or a fibrous structure comprising a fibrous element is designed to be used in a washing machine for laundry care purposes, the conditions of intended use will include those temperature, chemical, physical and/or mechanical conditions present in a washing machine, including any wash water, during a laundry washing operation. In another example, if a fibrous element and/or a particle and/or a fibrous structure comprising a fibrous element is designed to be used by a human as a shampoo for hair care purposes, the conditions of intended use will include those temperature, chemical, physical and/or mechanical conditions present during the shampooing of the human's hair. Likewise, if a fibrous element and/or a particle and/or a fibrous structure comprising a fibrous element is designed to be used in a dishwashing operation, by hand or by a dishwashing machine, the conditions of intended use will include the temperature, chemical, physical and/or mechanical conditions present in a dishwashing water and/or dishwashing machine, during the dishwashing operation.

"Active agent" as used herein means an additive that produces an intended effect in an environment external to a fibrous element and/or a particle and/or a fibrous structure comprising a fibrous element of the present invention, such as when the fibrous element and/or a particle and/or fibrous structure is exposed to conditions of intended use of the fibrous element and/or a particle and/or a fibrous structure comprising a fibrous element. In one example, an active agent comprises an additive that treats a surface, such as a hard surface (i.e., kitchen countertops, bath tubs, toilets, toilet bowls, sinks, floors, walls, teeth, cars, windows, mirrors, dishes) and/or a soft surface (i.e., fabric, hair, skin, carpet, crops, plants,). In another example, an active agent comprises an additive that creates a chemical reaction (i.e., foaming, fizzing, coloring, warming, cooling, lathering, disinfecting and/or clarifying and/or chlorinating, such as in clarifying water and/or disinfecting water and/or chlorinating water). In yet another example, an active agent comprises an additive that treats an environment (i.e., deodorizes, purifies, perfumes air). In one example, the active agent is formed in situ, such as during the formation of the fibrous element and/or particle containing the active agent, for example the fibrous element and/or particle may comprise a water-soluble polymer (e.g., starch) and a surfactant (e.g., anionic surfactant), which may create a polymer complex or coacervate that functions as the active agent used to treat fabric surfaces.

"Treats" as used herein with respect to treating a surface means that the active agent provides a benefit to a surface or environment. Treats includes regulating and/or immediately improving a surface's or environment's appearance, cleanliness, smell, purity and/or feel. In one example treating in reference to treating a keratinous tissue (for example skin and/or hair) surface means regulating and/or immediately improving the keratinous tissue's cosmetic appearance and/or feel. For instance, "regulating skin, hair, or nail (keratinous tissue) condition" includes: thickening of skin, hair, or nails (e.g, building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair.

In another example, treating means removing stains and/or odors from fabric articles, such as clothes, towels, linens, and/or hard surfaces, such as countertops and/or dishware including pots and pans.

"Fabric care active agent" as used herein means an active agent that when applied to a fabric provides a benefit and/or improvement to the fabric. Non-limiting examples of benefits and/or improvements to a fabric include cleaning (for example by surfactants), stain removal, stain reduction, wrinkle removal, color restoration, static control, wrinkle resistance, permanent press, wear reduction, wear resistance, pill removal, pill resistance, soil removal, soil resistance (including soil release), shape retention, shrinkage reduction, softness, fragrance, anti-bacterial, anti-viral, odor resistance, and odor removal.

"Dishwashing active agent" as used herein means an active agent that when applied to dishware, glassware, pots, pans, utensils, and/or cooking sheets provides a benefit and/or improvement to the dishware, glassware, plastic items, pots, pans and/or cooking sheets. Non-limiting examples of benefits and/or improvements to the dishware, glassware, plastic items, pots, pans, utensils, and/or cooking sheets include food and/or soil removal, cleaning (for example by surfactants) stain removal, stain reduction, grease removal, water spot removal and/or water spot prevention, glass and metal care, sanitization, shining, and polishing.

"Hard surface active agent" as used herein means an active agent when applied to floors, countertops, sinks, windows, mirrors, showers, baths, and/or toilets provides a benefit and/or improvement to the floors, countertops, sinks, windows, mirrors, showers, baths, and/or toilets. Non-limiting examples of benefits and/or improvements to the floors, countertops, sinks, windows, mirrors, showers, baths, and/or toilets include food and/or soil removal, cleaning (for example by surfactants), stain removal, stain reduction, grease removal, water spot removal and/or water spot prevention, limescale removal, disinfection, shining, polishing, and freshening.

"Particle", for example an active agent-containing particle, as used herein means a powder, granule, and/or agglomerate. The shape of the particle can be in the form of spheres, rods, plates, tubes, squares, rectangles, discs, stars, fibers or have regular or irregular random forms. The particles of the present invention, at least those of at least 44 μm, can be measured by the Particle Size Distribution Test Method described herein. For particles that are less than 44 μm, a different test method may be used, for example light scattering, to determine the particle sizes less than 44 μm, for example perfume microcapsules that typically range from about 15 μm to about 44 μm and/or about 25 μm in size.

In one aspect, particles may comprise re-cycled fibrous-structure materials, specifically where said fibrous materials are re-cycled by grinding fibers into a finely-divided solid and re-incorporating said finely-divided solids into agglomerates, granules or other particle forms. In another aspect, particles may comprise re-cycled fibrous-structure materials, specifically where said fibrous materials are incorporated into a fluid paste, suspension or solution, and then processed to form agglomerates, granules or other particle forms. In another aspect, said fluid pastes, suspensions or solutions comprising recycled fibrous materials may be directly applied to fibrous layers in the process of making new fibrous articles.

In one example, the particles exhibit a D50 of less than 500 μm and/or less than 450 μm and/or less than 400 μm and/or less than 350 μm to about 100 μm or to about 150 μm or to about 200 μm as measured according to the Particle Size Distribution Test Method described herein.

In one example, the particles, which may be discrete particles and/or agglomerates (discrete particles bound together) may exhibit a D50 particle size of from about 100 μm to about 5000 μm and/or from about 100 μm to about 2000 μm and/or from about 250 μm to about 1200 μm and/or from about 250 μm to about 850 μm as measured according to the Particle Size Distribution Test Method described herein.

In one example, the particles, which may be discrete particles and/or agglomerates (discrete particles bound together), may exhibit a D10 of 250 μm as measured according to the Particle Size Distribution Test Method described herein.

In another example, the particles and/or agglomerates (discrete particles bound together), may exhibit a D90 of 1200 μm and/or 850 μm as measured according to the Particle Size Distribution Test Method described herein.

In one example, the particles and/or agglomerates (discrete particles bound together), may exhibit a D10 of greater than 44 μm and/or greater than 90 μm and/or greater than 150 μm and/or greater than 212 μm and/or greater than 300 μm as measured according to the Particle Size Distribution Test Method described herein.

In one example, the particles and/or agglomerates (discrete particles bound together), may exhibit a D90 of less than 1400 μm and/or less than 1180 μm and/or less than 850 μm and/or less than 600 μm and/or less than 425 μm as measured according to the Particle Size Distribution Test Method described herein.

In one example, the particles and/or agglomerates (discrete particles bound together), may exhibit any combination of the above-identified D10, D50, and/or D90 so long as D50, when present, is greater than D10, when present, and D90, when present, is greater than D10 and D50, when present.

In one example, the particles and/or agglomerates (discrete particles bound together), may exhibit any combination of the above-identified D10 and D90 so long as D90 is greater than D10.

In one example, the particles and/or agglomerates (discrete particles bound together), may exhibit a D10 of greater than 212 μm and a D90 of less than 1180 μm as measured according to the Particle Size Distribution Test Method described herein.

In one example, the particles and/or agglomerates (discrete particles bound together), may exhibit a D10 of greater than 90 μm and a D90 of less than 425 μm as measured according to the Particle Size Distribution Test Method described herein.

"Effervescent system" as used herein means a mixture of one or more effervescent acids and/or effervescent acid particles and one or more effervescent salts and/or effervescent salt particles. In one example, the selection of specific effervescent acids, for example effervescent acid particles, and/or effervescent salts, for example effervescent salt particles, and their proportions depends, at least in part, upon the requirements for the amount of gas, for example $CO_2$ release. In one example, the effervescent acid, for example effervescent acid particle, such as citric acid, may be added in an amount of about 10% to about 60% by weight of the effervescent system, while the effervescent salt, for example effervescent salt particle, such as an alkali metal salt, for example sodium bicarbonate, may also be added in an amount of about 10% to 60% by weight of the effervescent components.

"Effervescent acid" or "Effervescent acid particle" as used herein means an acid and/or acid particle that generates effervescence, for example gas, such as $CO_2$, when combined with an Effervescent salt or Effervescent salt particle. Non-limiting examples of suitable effervescent acids and/or effervescent acid particles for use in the foaming compositions of the present invention include, but are not limited to, tartaric acid, citric acid, fumaric acid, adipic acid, malic acid, oxalic acid, sulfamic acid, and mixtures thereof. In one example, the effervescent acid and/or effervescent acid particle comprises citric acid or a mixture of citric acid and tartaric acid. The effervescent acid and/or effervescent acid particle may be anhydrous.

"Effervescent salt" or "Effervescent salt particle" as used herein means a salt and/or salt particle that generates effervescence, for example gas, such as $CO_2$, when combined with an effervescent acid and/or effervescent acid particle. Non-limiting examples of suitable effervescent salts and/or effervescent salt particles include, but are not limited to, alkali metal salts and/or carbonate salts and/or bicarbonate salts, such as sodium carbonate, calcium carbonate, magnesium carbonate, ammonium carbonate, potassium carbonate, sodium bicarbonate, calcium bicarbonate, and mixtures thereof. The effervescent salt and/or effervescent salt particle may be anhydrous.

"Weight ratio" as used herein means the ratio between two materials on their dry basis. For example, the weight ratio of fibrous element-forming materials to active agents within a fibrous element and/or plurality of fibrous elements is the ratio of the weight of fibrous element-forming material on a dry weight basis (g or %) in the fibrous element and/or in the plurality of fibrous elements to the weight of additive, such as active agent(s) on a dry weight basis (g or %—same units as the fibrous element-forming material weight) in the fibrous element and/or in the plurality of fibrous elements. In another example, the weight ratio of particles to fibrous elements within a fibrous structure is the ratio of the weight of particles on a dry weight basis (g or %) in the fibrous structure to the weight of fibrous elements on a dry weight basis (g or %—same units as the particle weight) in the fibrous structure.

"Water-soluble material" and/or "water-soluble fibrous structure" and/or "water-soluble fibrous element-forming material" and/or "water-soluble particle" as used herein means a material that is miscible in water. In other words, a material that is capable of forming a stable (does not separate for greater than 5 minutes after forming the homogeneous solution) homogeneous solution with water at ambient conditions.

"Ambient conditions" as used herein means 23° C.±1.0° C. and a relative humidity of 50%±2%.

"Weight average molecular weight" means the weight average molecular weight determined according to the Weight Average Molecular Weight Test Methods described herein.

"Length" as used herein, with respect to a fibrous element, means the length along the longest axis of the fibrous element from one terminus to the other terminus. If a fibrous element has a kink, curl or curves in it, then the length is the length along the entire path of the fibrous element from one terminus to the other terminus.

"Diameter" as used herein, with respect to a fibrous element, is measured according to the Diameter Test Method described herein. In one example, a fibrous element of the present invention exhibits a diameter of less than 100 µm and/or less than 75 µm and/or less than 50 µm and/or less than 25 µm and/or less than 20 µm and/or less than 15 µm and/or less than 10 µm and/or less than 6 µm and/or greater than 1 µm and/or greater than 3 µm.

"Triggering condition" as used herein in one example means anything, as an act or event, that serves as a stimulus and initiates or precipitates a change in the fibrous element and/or particle and/or fibrous structure of the present invention, such as a loss or altering of the fibrous element's and/or fibrous structure's physical structure and/or a release of an additive, such as an active agent therefrom. In another example, the triggering condition may be present in an environment, such as water, when a fibrous element and/or particle and/or fibrous structure of the present invention is added to the water. In other words, nothing changes in the water except for the fact that the fibrous element and/or fibrous structure of the present invention is added to the water.

"Morphology changes" as used herein with respect to a fibrous element's and/or particle's morphology changing means that the fibrous element experiences a change in its physical structure. Non-limiting examples of morphology changes for a fibrous element and/or particle of the present invention include dissolution, melting, swelling, shrinking, breaking into pieces, exploding, lengthening, shortening, and combinations thereof. The fibrous elements and/or particles of the present invention may completely or substantially lose their fibrous element or particle physical structure or they may have their morphology changed or they may retain or substantially retain their fibrous element or particle physical structure as they are exposed to conditions of intended use.

"By weight on a dry fibrous element basis" and/or "by weight on a dry particle basis" and/or "by weight on a dry fibrous structure basis" means the weight of the fibrous element and/or particle and/or fibrous structure, respectively, measured immediately after the fibrous element and/or particle and/or fibrous structure, respectively, has been conditioned in a conditioned room at a temperature of 23° C.±1.0° C. and a relative humidity of 50%±10% for 2 hours. In one example, by weight on a dry fibrous element basis and/or dry particle basis and/or dry fibrous structure basis means that the fibrous element and/or particle and/or fibrous structure comprises less than 20% and/or less than 15% and/or less than 10% and/or less than 7% and/or less than 5% and/or less than 3% to about or greater than 0% based on the dry weight of the fibrous element and/or particle and/or fibrous structure of moisture, such as water, for example free water, as measured according to the Water Content Test Method described herein.

"Total level" as used herein, for example with respect to the total level of one or more active agents present in the fibrous element and/or particle and/or fibrous structure, means the sum of the weights or weight percent of all of the subject materials, for example active agents. In other words, a fibrous element and/or particle and/or fibrous structure may comprise 25% by weight on a dry fibrous element basis and/or dry particle basis and/or dry fibrous structure basis of an anionic surfactant, 15% by weight on a dry fibrous element basis and/or dry particle basis and/or dry fibrous structure basis of a nonionic surfactant, 10% by weight of a chelant on a dry fibrous element basis and/or dry particle basis and/or dry fibrous structure basis, and 5% by weight of a perfume a dry fibrous element basis and/or dry particle basis and/or dry fibrous structure basis so that the total level of active agents present in the fibrous element and/or particle and/or fibrous structure is greater than 50%; namely 55% by weight on a dry fibrous element basis and/or dry particle basis and/or dry fibrous structure basis.

"Solids" or "total solids" refers to any ingredient besides water or solvent in the formula that does not evaporate. "High solids" as used herein refers to a solids and/or total solids present at a level of greater than 15% and/or greater than 20% and/or at least 25% and/or at least 35% and/or at least 40% and/or at least 50% to about 100% or to about 90% or to about 80% or to about 70% or to about 60% by weight and all ranges between these values.

"High surfactant" such as "high surfactant level(s)" refers to the ratio of surfactant to fibrous element-forming material, such as natural polymer-based fibrous element-forming material, for example a modified polysaccharide, such as a modified starch (starch derivative), for example acetylated starch (starch acetate) in the fibrous element-forming composition and/or fibrous element of the present invention. Such surfactant present in the fibrous element-forming composition and/or fibrous elements is different and independent of any surfactants that may be present in particles, such as active agent-containing particles, present in the fibrous structures and/or products of the present invention. In one example, the weight ratio range of surfactant to fibrous element-forming material is from about 1:2 up to about 5:1 and/or from about 1:1 to about 4:1 and/or from about 2:1 to about 3:1 and/or about 2:1.

"Fibrous structure product" as used herein means a solid form, for example a rectangular solid, sometimes referred to as a sheet, in this case one or more fibrous structures of the present invention, that comprises a plurality of fibrous elements and a plurality of particles. The fibrous structure products comprises one or more active agents, for example an effervescent agent, a fabric care active agent, a dishwashing active agent, a hard surface active agent, and mixtures thereof, present in the fibrous elements and/or particles of the fibrous structure and/or fibrous structure product. In one example, a fibrous structure product of the present invention comprises one or more surfactants, one or more enzymes (such as in the form of an enzyme prill), one or more perfumes and/or one or more suds suppressors. In another example, a fibrous structure product of the present invention comprises a builder and/or a chelating agent. In another example, a fibrous structure product of the present invention comprises a bleaching agent (such as an encapsulated bleaching agent).

"Different from" or "different" as used herein means, with respect to a material, such as a fibrous element as a whole and/or a fibrous element-forming material within a fibrous element and/or an active agent within a fibrous element, that one material, such as a fibrous element and/or a fibrous element-forming material and/or an active agent, is chemically, physically and/or structurally different from another material, such as a fibrous element and/or a fibrous element-forming material and/or an active agent. For example, a fibrous element-forming material in the form of a filament is different from the same fibrous element-forming material in the form of a fiber. Likewise, a starch polymer is different from a cellulose polymer. However, different molecular weights of the same material, such as different molecular weights of a starch, are not different materials from one another for purposes of the present invention.

"Random mixture of polymers" as used herein means that two or more different fibrous element-forming materials are randomly combined to form a fibrous element. Accordingly, two or more different fibrous element-forming materials that are orderly combined to form a fibrous element, such as a core and sheath bicomponent fibrous element, is not a random mixture of different fibrous element-forming materials for purposes of the present invention.

"Associate," "Associated," "Association," and/or "Associating" as used herein with respect to fibrous elements and/or particle means combining, either in direct contact or in indirect contact, fibrous elements and/or particles such that a fibrous structure is formed. In one example, the associated fibrous elements and/or particles may be bonded together for example by adhesives and/or thermal bonds. In another example, the fibrous elements and/or particles may be associated with one another by being deposited onto the same fibrous structure making belt and/or patterned belt.

"Aperture" as used herein means an opening or void or indentation in a fibrous structure which is distinct from the surrounding fibrous structure. In one example, an aperture may comprise any feature where there is a localized disruption of the fibrous structure. In one example, an aperture may comprise a local indentation or localized disruption of the basis weight, thickness, or caliper of the fibrous structure. In another example, an aperture may be an opening in a fibrous structure wherein the opening passes substantially or completely through both generally planar surfaces of the fibrous structure, through one generally planar surface of the fibrous structure, or even through neither planar surface of the fibrous structure. In another example, an aperture may be an opening in the fibrous structure wherein there is a complete opening, partial opening, or even no apparent opening. In still another example, an aperture may comprise a feature which is an embossment in the fibrous structure. In even another example, an aperture is an internal feature to a fibrous structure and/or multi-ply fibrous structure wherein for example the aperture feature may be present on an internal ply of a multi-ply fibrous structure. In even yet another example, an aperture comprises an opening or void or indentation in a fibrous structure wherein the opening or void or indentation is a non-random and/or designed and/or fabricated opening, void, or indentation rather than a random pore that exists between and/or amongst fibrous elements of a fibrous structure resulting from the collection and interentangling of fibrous elements on a collection device.

"Machine Direction" or "MD" as used herein means the direction parallel to the flow of the fibrous structure through the fibrous structure making machine and/or fibrous structure product manufacturing equipment.

"Cross Machine Direction" or "CD" as used herein means the direction perpendicular to the machine direction in the same plane of the fibrous structure and/or fibrous structure product comprising the fibrous structure.

"Ply" or "Plies" as used herein means an individual fibrous structure optionally to be disposed in a substantially contiguous, face-to-face relationship with other plies, forming a multiple ply fibrous structure. It is also contemplated that a single fibrous structure can effectively form two "plies" or multiple "plies", for example, by being folded on itself.

As used herein, the articles "a" and "an" when used herein, for example, "an anionic surfactant" or "a fiber" is understood to mean one or more of the material that is claimed or described.

All percentages and ratios are calculated by weight unless otherwise indicated. All percentages and ratios are calculated based on the total composition unless otherwise indicated.

Unless otherwise noted, all component or composition levels are in reference to the active level of that component or composition, and are exclusive of impurities, for example, residual solvents or by-products, which may be present in commercially available sources.

Fibrous Structure

The fibrous structure of the present invention comprises a plurality of natural polymer-based fibrous elements, for example a plurality of natural polymer-based filaments, and optionally, one or more particles, for example one or more active agent-containing particles, such as water-soluble, active agent-containing particles.

In one example, the fibrous elements and/or particles may be arranged within the fibrous structure to provide the fibrous structure with two or more regions that comprise different active agents. For example, one region of the fibrous structure may comprise bleaching agents and/or surfactants and another region of the fibrous structure may comprise softening agents.

Non-limiting examples of various fibrous structures and/or fibrous structure products according to the present invention are discussed below. Even though the non-limiting examples described below illustrate particles being a part of the fibrous structures and/or fibrous structure products, the fibrous structures and/or fibrous structure products may be void of such particles and contain only fibrous elements, for example natural polymer-based fibrous elements.

As shown in FIG. 1, an example of a fibrous structure 10 according to the present invention comprises a first layer 12 comprising a plurality of fibrous elements 14, for example natural polymer-based fibrous elements, in this case filaments, for example natural polymer-based filaments, a second layer 16 comprising a plurality of fibrous elements 14, for example natural polymer-based fibrous elements, in this case filaments, for example natural polymer-based filaments, and a plurality of particles 18, for example active agent-containing particles, positioned between the first and second layers 12 and 16. A similar fibrous structure can be formed by depositing a plurality of particles, for example active agent-containing particles on a surface of a first ply of fibrous structure comprising a plurality of fibrous elements, for example natural polymer-based fibrous elements, and then associating a second ply of fibrous structure, for example a fibrous structure according to the present invention, comprising a plurality of fibrous elements, for example natural polymer-based fibrous elements, such that the particles are positioned between the first and second plies.

Figure 2:
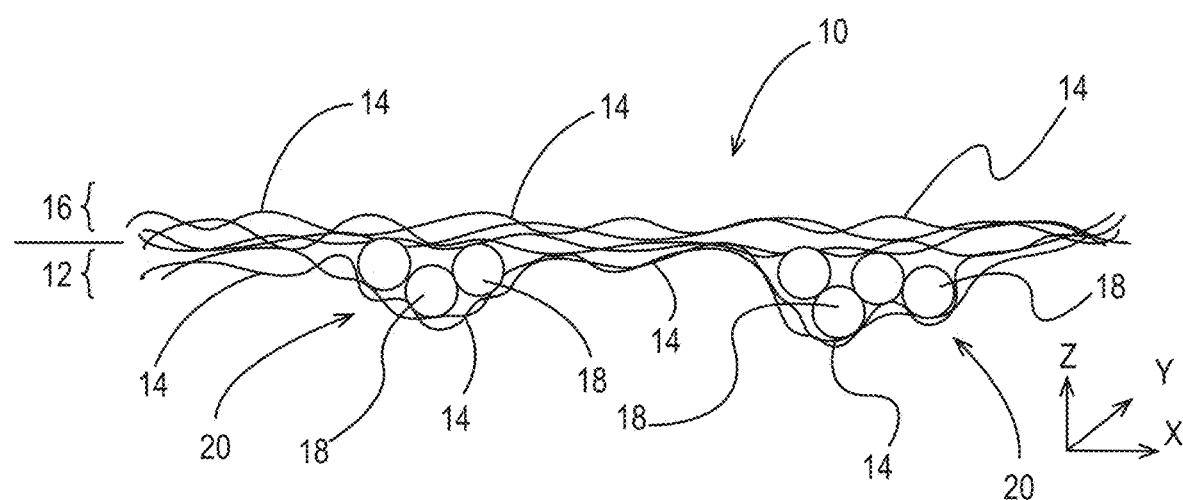
FIG. 2 is a schematic representation of a cross-sectional view of another example of a fibrous structure according to the present invention.

As shown in FIG. 2, another example of a fibrous structure 10 of the present invention comprises a first layer 12 comprising a plurality of fibrous elements 14, for example natural polymer-based fibrous elements, in this case filaments, for example natural polymer-based filaments, wherein the first layer 12 comprises one or more pockets 20 (also referred to as recesses), which may be in a non-random, repeating pattern. One or more of the pockets 20 may contain one or more particles 18, for example active agent-containing particles. The fibrous structure 10 further comprises a second layer 16 that is associated with the first layer 12 such that the particles 18, for example active agent-containing particles, are entrapped in the pockets 20. Like above, a similar fibrous structure can be formed by depositing a plurality of particles, for example active agent-containing particles, in pockets of a first ply of fibrous structure comprising a plurality of fibrous elements, for example natural polymer-based fibrous elements, and then associating a second ply of fibrous structure, for example a fibrous structure according to the present invention, comprising a plurality of fibrous elements, for example natural polymer-based fibrous elements, such that the particles, for example active agent-containing particles, are entrapped within the pockets of the first ply. In one example, the pockets may be separated from the fibrous structure to produce discrete pockets.

Figure 3:
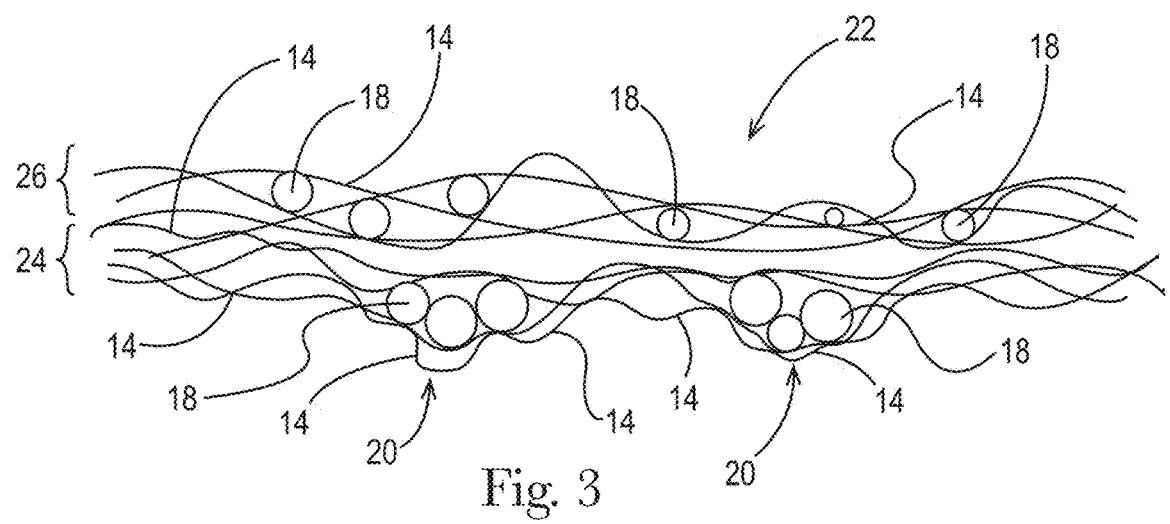
FIG. 3 is a schematic representation of a cross-sectional view of another example of a fibrous structure according to the present invention.

As shown in FIG. 3, an example of a multi-ply fibrous structure 22 of the present invention comprises a first ply 24 of a fibrous structure according to FIG. 2 above and a second ply 26 of a fibrous structure, for example a fibrous structure according to the present invention, associated, for example by an edge seam (not shown), with the first ply 24, wherein the second ply 26 comprises a plurality of fibrous elements 14, for example natural polymer-based fibrous elements, in this case filaments, for example natural polymer-based filaments, and a plurality of particles 18, for example active agent-containing particles, dispersed, in this case randomly, in the x, y, and z axes, throughout one or both plies and/or throughout the entire multi-ply fibrous structure. In other words, the particles, for example active agent-containing particles, such as water-soluble, active agent-containing particles, are commingled with the fibrous elements, for example natural polymer-based fibrous elements, of one or both fibrous structure plies.

Figure 4:
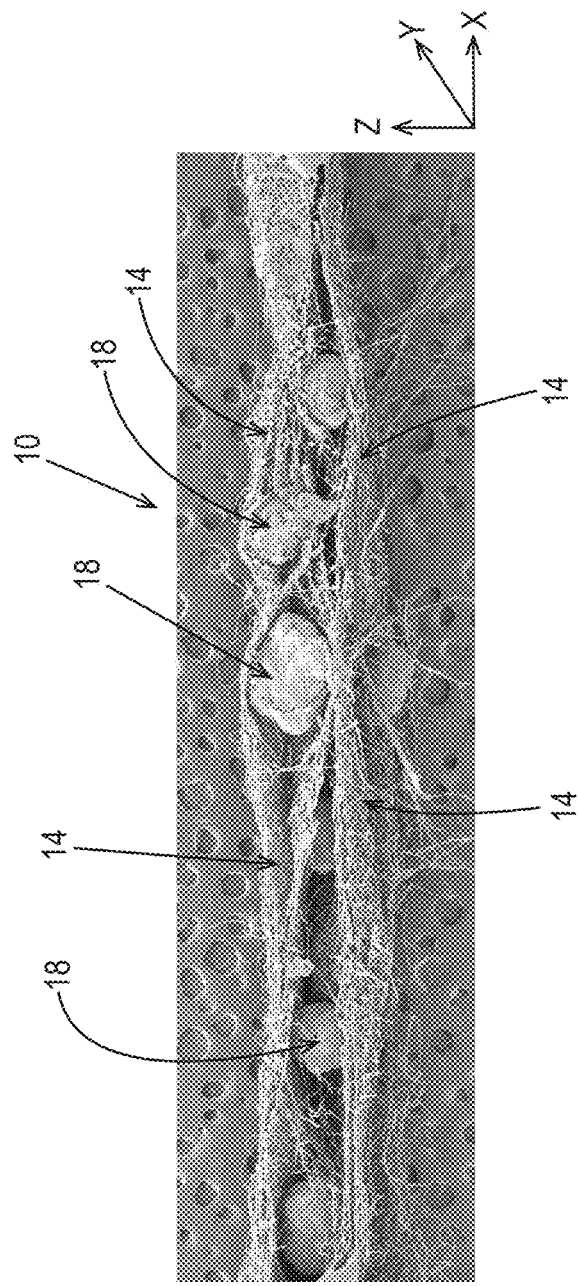
FIG. 4 is a scanning electron microscope photograph of a cross-sectional view of another example of a fibrous structure according to the present invention.

As shown in FIG. 4, an example of a fibrous structure 10 of the present invention comprises a plurality of fibrous elements 14, for example natural polymer-based fibrous elements, in this case filaments, for example natural polymer-based filaments, and a plurality of particles 18, for example active agent-containing particles, dispersed, in this case randomly, in the x, y, and z axes, throughout the fibrous structure 10.

Even though the fibrous elements and/or fibrous structure of the present invention are in solid form, the filament-forming composition used to make the fibrous elements of the present invention may be in the form of a liquid.

In one example, the fibrous structure comprises a plurality of identical or substantially identical (from a compositional perspective) fibrous elements, for example natural polymer-based fibrous elements, and/or particles, for example active agent-containing particles, according to the present invention. In another example, the fibrous structure may comprise two or more different fibrous elements, for example natural polymer-based fibrous elements, and/or particles, for example active agent-containing particles, according to the present invention. Non-limiting examples of differences in the fibrous elements and/or particles may be physical differences such as differences in diameter, length, texture, shape, rigidness, elasticity, and the like; chemical differences such as crosslinking level, solubility, melting point, Tg, active agent, filament-forming material, color, level of active agent, basis weight, density, level of filament-forming material, presence of any coating on fibrous element, biodegradable or not, hydrophobic or not, contact angle, and the like; differences in whether the fibrous element and/or particle loses its physical structure when the fibrous element and/or particle is exposed to conditions of intended use; differences in whether the fibrous element's and/or particle's morphology changes when the fibrous element and/or particle is exposed to conditions of intended use; and differences in rate at which the fibrous element and/or particle releases one or more of its active agents when the fibrous element and/or particle is exposed to conditions of intended use. In one example, two or more fibrous elements, for example natural polymer-based fibrous elements, and/or particles, for example active agent-containing particles, within the fibrous structure may comprise different active agents. This may be the case where the different active agents may be incompatible with one another, for example an anionic surfactant (such as a shampoo active agent) and a cationic surfactant (such as a hair conditioner active agent).

In another example, the fibrous structure may exhibit different regions, such as different regions of basis weight, density and/or caliper. In yet another example, the fibrous structure may comprise texture on one or more of its surfaces. A surface of the fibrous structure may comprise a pattern, such as a non-random, repeating pattern. The fibrous structure may be embossed with an emboss pattern. In another example, the fibrous structure may comprise apertures. The apertures may be arranged in a non-random, repeating pattern.

In another example of the present invention, the fibrous structure comprises one or more apertures and thus is an apertured fibrous structure. In one example, the fibrous structure comprises a plurality of apertures. The apertures may be arranged in a pattern, for example a repeating pattern, such as a non-random, repeating pattern, and/or a non-repeating pattern.

Apertures within the apertured fibrous structure of the present invention may be of virtually any shape and size. In one example, the apertures within the apertured fibrous structures are generally round or oblong shaped, in a regular pattern of spaced apart openings. In one example, the fibrous structure comprises two or more apertures that are spaced apart from one another at a distance of from about 0.2 mm to about 100 mm and/or from about 0.5 mm to about 10 mm.

Aperturing of fibrous structures, for example soluble fibrous structures, such as water soluble fibrous structures, can be accomplished by any number of techniques. For example, aperturing can be accomplished by various processes involving bonding and stretching, such as those described in U.S. Pat. Nos. 3,949,127 and 5,873,868. In one example, the apertures may be formed by forming a plurality of spaced, melt stabilized regions, and then ring-rolling the web to stretch the web and form apertures in the melt stabilized regions, as described in U.S. Pat. Nos. 5,628,097 and 5,916,661, both of which are hereby incorporated by reference herein. In another example, apertures can be formed in a multilayer, fibrous structure configuration by the method described in U.S. Pat. Nos. 6,830,800, 6,863,960, 8,241,543, 10,792,229, which are hereby incorporated herein by reference. Non-limiting examples of processes for imparting apertures to a fibrous structure of the present invention include embossing, rodding, rotary knife aperturing, pinning, die cutting, die punching, needlepunching, knurling, crush cutting, shear cutting, pneumatic forming, hydraulic forming, laser cutting, and tufting. In one example, the fibrous structure of the present invention comprises pinning-imparted apertures. In another example, the fibrous structure of the present invention comprises rodding-imparted apertures. In another example, the fibrous structure of the present invention comprises rotary knife aperturing-imparted apertures. In still another example, the fibrous structure of the present invention may comprise apertures that have been imparted to the fibrous structure by different types of aperturing processes.

In one example, apertures may be imparted to a fibrous structure during forming of the fibrous structure on a collection device, such as a patterned belt, that has features, for example depressions and/or protrusions that impart apertures to the fibrous structure upon the fibrous elements contacting the collection device during formation.

In one example, the fibrous structure may comprise discrete regions of fibrous elements that differ from other parts of the fibrous structure.

Non-limiting examples of use of the fibrous structure of the present invention include, but are not limited to a laundry dryer substrate, washing machine substrate, washcloth, hard surface cleaning and/or polishing substrate, floor cleaning and/or polishing substrate, as a component in a battery, baby wipe, adult wipe, feminine hygiene wipe, bath tissue wipe, window cleaning substrate, oil containment and/or scavenging substrate, insect repellant substrate, swimming pool chemical substrate, food, breath freshener, deodorant, waste disposal bag, packaging film and/or wrap, wound dressing, medicine delivery, building insulation, crops and/or plant cover and/or bedding, glue substrate, skin care substrate, hair care substrate, air care substrate, water treatment substrate and/or filter, toilet bowl cleaning substrate, candy substrate, pet food, livestock bedding, teeth whitening substrates, carpet cleaning substrates, and other suitable uses of the active agents of the present invention.

The fibrous structure of the present invention may be used as is or may be coated with one or more active agents.

In one example, the article, for example fibrous structure of the present invention may exhibit an average disintegration time of less than 360 seconds (s) and/or less than 200 s and/or less than 100 s and/or less than 60 s and/or less than 30 s, and/or less than 10 s and/or less than 5 s and/or less than 2.0 s and/or less than 1.5 s and/or about 0 s and/or greater than 0 s as measured according to the Dissolution Test Method described herein.

In one example, the article, for example fibrous structure of the present invention may exhibit an average dissolution time of less than 3600 seconds (s) and/or less than 3000 s and/or less than 2400 s and/or less than 1800 s and/or less than 1200 s and/or less than 600 s and/or less than 400 s and/or less than 300 s and/or less than 200 s and/or less than 175 s and/or less than 100 s and/or less than 50 s and/or greater than 1 s as measured according to the Dissolution Test Method described herein.

In another example, the article, for example fibrous structure of the present invention exhibits an average dissolution time of less than 24 hours and/or less than 12 hours and/or less than 6 hours and/or less than 1 hour (3600 seconds) and/or less than 30 minutes and/or less than 25 minutes and/or less than 20 minutes and/or less than 15 minutes and/or less than 10 minutes and/or less than 5 minutes and/or greater than 1 second and/or greater than 5 seconds and/or greater than 10 seconds and/or greater than 30 seconds and/or greater than 1 minute as measured according to the Dissolution Test Method described herein.

In one example, the article, for example fibrous structure of the present invention may exhibit an average disintegration time per gsm of sample of about 1.0 second/gsm (s/gsm) or less, and/or about 0.5 s/gsm or less, and/or about 0.2 s/gsm or less, and/or about 0.1 s/gsm or less, and/or about 0.05 s/gsm or less, and/or about 0.03 s/gsm or less as measured according to the Dissolution Test Method described herein.

In one example, the article, for example fibrous structure of the present invention may exhibit an average dissolution time per gsm of sample of about 10 seconds/gsm (s/gsm) or less, and/or about 5.0 s/gsm or less, and/or about 3.0 s/gsm or less, and/or about 2.0 s/gsm or less, and/or about 1.8 s/gsm or less, and/or about 1.5 s/gsm or less as measured according to the Dissolution Test Method described herein.

In one example, the fibrous structure of the present invention exhibits a thickness of greater than 0.01 mm and/or greater than 0.05 mm and/or greater than 0.1 mm to about 100 mm or to about 50 mm or to about 20 mm or to about 10 mm or to about 5 mm or to about 2 mm or to about 0.5 mm or to about 0.3 mm as measured by the Thickness Test Method described herein.

In one example, the fibrous structure of the present invention comprises a plurality of fibrous elements, for example natural polymer-based fibrous elements that comprising a total level of the one or more fibrous element-forming materials, for example natural polymer-based fibrous element-forming materials, of less than 80% by weight of the dry fibrous elements and a total level of the one or more active agents comprising a surfactant or surfactant mixture and optionally additional non-surfactant active agents of greater than 20% by weight of the dry fibrous elements.

In one example, the fibrous structure of the present invention comprises a plurality of fibrous elements, for example natural polymer-based fibrous elements, comprising a total level of the one or more fibrous element-forming materials, for example natural polymer-based fibrous element-forming materials, of less than 70% by weight of the dry fibrous elements and a total level of the one or more active agents comprising a surfactant or surfactant mixture and optionally additional non-surfactant active agents of greater than 30% by weight of the dry fibrous elements.

In one example, the fibrous structure of the present invention comprises a plurality of fibrous elements, for example natural polymer-based fibrous elements, comprising a total level of the one or more fibrous element-forming materials, for example natural polymer-based fibrous element-forming materials, of less than 60% by weight of the dry fibrous elements and a total level of the one or more active agents comprising a surfactant or surfactant mixture and optionally additional non-surfactant active agents of greater than 40% by weight of the dry fibrous elements.

In one example, the fibrous structure of the present invention comprises a plurality of fibrous elements, for example natural polymer-based fibrous elements, comprising a total level of the one or more fibrous element-forming materials, for example natural polymer-based fibrous element-forming materials, of about 50% by weight of the dry fibrous elements and a total level of the one or more active agents comprising a surfactant or surfactant mixture and optionally additional non-surfactant active agents of about 50% by weight of the dry fibrous elements.

In one example, the fibrous structure of the present invention comprises a plurality of fibrous elements, for example natural polymer-based fibrous elements, comprising a total level of the one or more fibrous element-forming materials, for example natural polymer-based fibrous element-forming materials, of less than 40% by weight of the dry fibrous elements and a total level of the one or more active agents comprising a surfactant or surfactant mixture and optionally additional non-surfactant active agents of greater than 60% by weight of the dry fibrous elements.

In one example, the fibrous structure of the present invention comprises a plurality of fibrous elements, for example natural polymer-based fibrous elements, comprising a total level of the one or more fibrous element-forming materials, natural polymer-based fibrous element-forming materials, of less than 30% by weight of the dry fibrous elements and a total level of the one or more active agents comprising a surfactant or surfactant mixture and optionally additional non-surfactant active agents of greater than 70% by weight of the dry fibrous elements.

In one example, the fibrous structure of the present invention comprises a plurality of fibrous elements, for example natural polymer-based fibrous elements, comprising a fibrous element-forming material, for example a natural polymer-based fibrous element-forming material, such as a modified polysaccharide, for example a modified starch, such as acetylated starch, and one or more active agents comprising a surfactant or surfactant mixture, for example comprising a linear alkylbenzene sulfonate and an alkyl sulfate, wherein the surfactant or surfactant mixture and the fibrous element-forming material, for example the natural polymer-based material, for example acetylated starch, are present in the fibrous structure at a weight ratio of surfactant or surfactant mixture to natural polymer-based fibrous element-forming material, for example acetylated starch, from about 0.15:1 to about 6:1 and/or from about 0.20:1 to about 5.5:1 and/or from about 0.25:1 to about 5:1 and/or from about 0.5:1 to about 2:1.

In one example, the surfactant and/or surfactant mixture present in the fibrous structures and/or fibrous elements and/or particles of the present invention may comprise surfactants suitable for beauty care and/or personal care applications such as hand wash, face wash, body wash, shampoo and other hair cleaning and/or conditioning application. Non-limiting examples of surfactants suitable for such beauty care and/or personal care applications include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one example, the surfactant and/or surfactant mixture comprises one or more sulfate-free surfactants and/or 100% sulfate-free surfactants.

In one example, the fibrous structure and/or fibrous elements and/or particles comprises a plurality of fibrous elements of the present invention further comprises a coating composition, for example a coating composition comprising one or more active agents, present on an external surface of the fibrous structure and/or fibrous element and/or particle.

In one example, the fibrous structure and/or fibrous elements and/or particles of the present invention comprises a natural polymer-based material, for example a modified polysaccharide, such as a modified starch, for example acetylated starch, and two or more different active agents, at least one of which is a surfactant or surfactant mixture.

In one example, the fibrous structure and/or fibrous elements and/or particles of the present invention exhibit a water content of from 0% to about 20% and/or greater than 0% to less than 15% as measured according to the Water Content Test Method.

The fibrous structures, fibrous elements and fibrous element-forming compositions of the present invention may comprise or be void of extensional aids. In other words, in one example, the fibrous elements of the present invention may be spun from a fibrous element-forming composition without the need for an extensional aid.

Fibrous Elements

The fibrous elements, for example natural polymer-based fibrous elements, may be water-soluble or water-insoluble. In one example, the fibrous elements, for example natural polymer-based fibrous elements, comprise one or more filament-forming materials, for example a natural polymer-based fibrous element-forming material. In another example, the fibrous elements, for example natural polymer-based fibrous elements, comprise one or more active agents. In still another example, the fibrous elements, for example natural polymer-based fibrous elements, comprise one or more filament-forming materials, for example natural polymer-based fibrous element-forming materials, and one or more active agents. In another example, the fibrous elements, for example natural polymer-based fibrous elements, are water-soluble, natural polymer-based fibrous elements.

The fibrous element, for example a natural polymer-based fibrous elements, such as a filament and/or fiber, for example a natural polymer-based filament and/or natural polymer-based fiber, of the present invention comprises one or more filament-forming materials, for example natural polymer-based fibrous element-forming materials. In addition to the filament-forming materials, the fibrous element, for example natural polymer-based fibrous element, may further comprise one or more active agents that are releasable from the fibrous element, such as when the fibrous element and/or fibrous structure comprising the fibrous element is exposed to conditions of intended use. In one example, the total level of the one or more filament-forming materials, for example natural polymer-based fibrous element-forming materials, present in the fibrous element, for example natural polymer-based fibrous element, and/or plurality of fibrous elements is less than 80% by weight on a dry fibrous element basis and/or dry fibrous structure basis and the total level of the one or more active agents present in the fibrous element, for example natural polymer-based fibrous element, and/or plurality of fibrous elements is greater than 20% by weight on a dry fibrous element basis and/or dry fibrous structure basis.

In one example, the fibrous element, for example natural polymer-based fibrous element, and/or a plurality of the fibrous elements of the present invention comprises about 100% and/or greater than 95% and/or greater than 90% and/or greater than 85% and/or greater than 75% and/or greater than 50% by weight on a dry fibrous element basis and/or dry fibrous structure basis of one or more filament-forming materials, for example natural polymer-based fibrous element-forming materials, such as a modified polysaccharide, for example a modified starch, such as acetylated starch.

In another example, the fibrous element, for example natural polymer-based fibrous element, and/or a plurality of the fibrous elements of the present invention comprises one or more filament-forming materials, for example natural polymer-based fibrous element-forming materials, such as a modified polysaccharide, for example a modified starch, such as acetylated starch, and one or more active agents wherein at least one of the active agents comprises a surfactant, for example a surfactant mixture comprising two or more surfactants, such as linear alkylbenzene sulfonate and alkyl sulfate, wherein the total level of filament-forming materials, for example natural polymer-based fibrous element-forming materials, present in the fibrous element, for example natural polymer-based fibrous element, and/or a plurality of the fibrous elements is from about 5% to less than 80% by weight on a dry fibrous element basis and/or dry fibrous structure basis and the total level of active agents comprising a surfactant or surfactant mixture and optionally one or more additional non-surfactant active agents, present in the fibrous element, for example natural polymer-based fibrous element, and/or a plurality of the fibrous elements is greater than 20% to about 95% by weight on a dry fibrous element basis and/or dry fibrous structure basis.

In one example, the fibrous element, for example natural polymer-based fibrous element, and/or a plurality of the fibrous elements of the present invention comprises at least 10% and/or at least 15% and/or at least 20% and/or less than less than 80% and/or less than 75% and/or less than 65% and/or less than 60% and/or less than 55% and/or less than 50% and/or less than 45% and/or less than 40% by weight on a dry fibrous element basis and/or dry fibrous structure basis of the filament-forming materials, for example natural polymer-based fibrous element-forming materials, and greater than 20% and/or at least 35% and/or at least 40% and/or at least 45% and/or at least 50% and/or at least 60% and/or less than 95% and/or less than 90% and/or less than 85% and/or less than 80% and/or less than 75% by weight on a dry fibrous element basis and/or dry fibrous structure basis of active agents comprising a surfactant or surfactant mixture and optionally one or more additional non-surfactant active agents.

In one example, the fibrous element, for example natural polymer-based fibrous element, and/or a plurality of the fibrous elements of the present invention comprises at least 5% and/or at least 10% and/or at least 15% and/or at least 20% and/or less than 50% and/or less than 45% and/or less than 40% and/or less than 35% and/or less than 30% and/or less than 25% by weight on a dry fibrous element basis and/or dry fibrous structure basis of the filament-forming materials, for example natural polymer-based fibrous element-forming materials, and greater than 50% and/or at least 55% and/or at least 60% and/or at least 65% and/or at least 70% and/or less than 95% and/or less than 90% and/or less than 85% and/or less than 80% and/or less than 75% by weight on a dry fibrous element basis and/or dry fibrous structure basis of active agents comprising a surfactant or surfactant mixture and optionally one or more additional non-surfactant active agents. In one example, the fibrous element, for example natural polymer-based fibrous element, and/or a plurality of the fibrous elements of the present invention comprises greater than 80% by weight on a dry fibrous element basis and/or dry fibrous structure basis of active agents comprising a surfactant or surfactant mixture and optionally one or more additional non-surfactant active agents.

In one example, the fibrous element, for example natural polymer-based fibrous element and/or plurality of fibrous elements of the present invention comprises a total level of the modified polysaccharide of less than 80% by weight of the dry fibrous elements and a total level of the surfactant of greater than 20% by weight of the dry fibrous elements.

In one example, the fibrous element, for example natural polymer-based fibrous element and/or plurality of fibrous elements of the present invention comprises a total level of the modified polysaccharide of less than 70% by weight of the dry fibrous elements and a total level of the surfactant of greater than 30% by weight of the dry fibrous elements.

In one example, the fibrous element, for example natural polymer-based fibrous element and/or plurality of fibrous elements of the present invention comprises a total level of the modified polysaccharide of less than 60% by weight of the dry fibrous elements and a total level of the surfactant of greater than 40% by weight of the dry fibrous elements.

In one example, the fibrous element, for example natural polymer-based fibrous element and/or plurality of fibrous elements of the present invention comprises a total level of the modified polysaccharide of about 50% by weight of the dry fibrous elements and a total level of the surfactant of about 50% by weight of the dry fibrous element.

In one example, the fibrous element, for example natural polymer-based fibrous element and/or plurality of fibrous elements of the present invention comprises a total level of the modified polysaccharide of less than 40% by weight of the dry fibrous elements and a total level of the surfactant of greater than 60% by weight of the dry fibrous elements.

In one example, the fibrous element, for example natural polymer-based fibrous element and/or plurality of fibrous elements comprises a total level of the modified polysaccharide of less than 30% by weight of the dry fibrous elements and a total level of the surfactant of greater than 70% by weight of the dry fibrous elements.

In one example, the fibrous element, for example natural polymer-based fibrous element and/or plurality of fibrous elements of the present invention comprises a modified polysaccharide and a surfactant or surfactant mixture present in the dry fibrous element at a weight ratio of modified polysaccharide to surfactant of 1 or less. The surfactant and/or surfactant mixture may comprise one or more surfactants selected from the group consisting of: anionic surfactants, cationic surfactants, nonionic surfactants, zwitterionic surfactants, amphoteric surfactants, and mixtures thereof.

In one example, the fibrous element, for example natural polymer-based fibrous element and/or plurality of fibrous elements of the present invention comprises a modified polysaccharide and one or more active agents comprising a surfactant or surfactant mixture and optionally additional non-surfactant active agents present in the dry fibrous element at a weight ratio of modified polysaccharide to surfactant of 1 or less. The surfactant and/or surfactant mixture may comprise one or more surfactants selected from the group consisting of: anionic surfactants, cationic surfactants, nonionic surfactants, zwitterionic surfactants, amphoteric surfactants, and mixtures thereof and the non-surfactant active agents may be selected from the group consisting of: skin care active agents, medicinal agents, lotions, fabric care active agents, dishwashing active agents, carpet care active agents, surface care active agents, hair care active agents, air care active agents, tooth care active agents, and mixtures thereof.

In another example, the one or more filament-forming materials, for example natural polymer-based fibrous element-forming materials, and active agents comprising a surfactant or surfactant mixture and optionally one or more additional non-surfactant active agents are present in the fibrous element, for example natural polymer-based fibrous element, and/or a plurality of the fibrous elements at a weight ratio of total level of filament-forming materials, for example natural polymer-based fibrous element-forming materials, to active agents, for example surfactant or surfactant mixture, of 4.0 or less and/or 3.5 or less and/or 3.0 or less and/or 2.5 or less and/or 2.0 or less and/or 1.85 or less and/or less than 1.7 and/or less than 1.6 and/or less than 1.5 and/or less than 1.3 and/or less than 1.2 and/or less than 1 and/or less than 0.7 and/or less than 0.5 and/or less than 0.4 and/or less than 0.3 and/or greater than 0.1 and/or greater than 0.15 and/or greater than 0.2.

In one example, the fibrous element, for example natural polymer-based fibrous element and/or plurality of fibrous elements of the present invention comprise one or more fibrous element-forming materials, for example natural polymer-based fibrous element-forming materials, and one or more active agents comprising a surfactant or surfactant mixture at a weight ratio of the fibrous element-forming materials to the active agents of 1 or less.

In still another example, the fibrous element, for example natural polymer-based fibrous element, and/or a plurality of the fibrous elements of the present invention comprises from about 10% and/or from about 15% to less than 80% by weight on a dry fibrous element basis and/or dry fibrous structure basis of a filament-forming material, for example natural polymer-based filament forming material, such as a modified polysaccharide, such as modified starch, for example acetylated starch, and greater than 20% to about 90% or to about 85% by weight on a dry fibrous element basis and/or dry fibrous structure basis of an active agent, for example surfactant or surfactant mixture. The fibrous element may further comprise a plasticizer, such as glycerin and/or pH adjusting agents, such as citric acid.

In yet another example, the fibrous element, for example natural polymer-based fibrous element, and/or a plurality of the fibrous elements of the present invention comprises from about 10% and/or from about 15% to less than 80% by weight on a dry fibrous element basis and/or dry fibrous structure basis of a filament-forming material, for example natural polymer-based filament forming material, such as a modified polysaccharide, such as modified starch, for example acetylated starch, and greater than 20% to about 90% or to about 85% by weight on a dry fibrous element basis and/or dry fibrous structure basis of an active agent, wherein the weight ratio of filament-forming material to active agent, for example surfactant or surfactant mixture is 4.0 or less. The fibrous element, for example natural polymer-based fibrous element, and/or a plurality of the fibrous elements may further comprise a plasticizer, such as glycerin and/or pH adjusting agents, such as citric acid.

In even another example of the present invention, a fibrous element, for example natural polymer-based fibrous element, and/or a plurality of the fibrous elements comprises one or more filament-forming materials, for example natural polymer-based fibrous element-forming materials, and one or more active agents selected from the group consisting of: enzymes, bleaching agents, builder, chelants, sensates, dispersants, and mixtures thereof that are releasable and/or released when the fibrous element and/or fibrous structure comprising the fibrous element is exposed to conditions of intended use. In one example, the fibrous element, for example natural polymer-based fibrous element, and/or a plurality of the fibrous elements comprises a total level of filament-forming materials, for example natural polymer-based fibrous element-forming materials, of less than 95% and/or less than 90% and/or less than 80% and/or less than 50% and/or less than 35% to about 5% or to about 10% or to about 20% by weight on a dry fibrous element basis and/or dry fibrous structure basis and a total level of active agents comprising a surfactant or surfactant mixture and optionally one or more additional active agents selected from the group consisting of: enzymes, bleaching agents, builder, chelants, perfumes, antimicrobials, antibacterials, antifungals, and mixtures thereof of greater than 5% and/or greater than 10% and/or greater than 20% and/or greater than 35% and/or greater than 50% and/or greater than 65% or to about 95% or to about 90% or to about 80% by weight on a dry fibrous element basis and/or dry fibrous structure basis. In one example, the active agent comprises one or more enzymes. In another example, the active agent comprises one or more bleaching agents. In yet another example, the active agent comprises one or more builders. In still another example, the active agent comprises one or more chelants. In still another example, the active agent comprises one or more perfumes. In even still another example, the active agent comprise one or more antimicrobials, antibacterials, and/or antifungals.

In yet another example of the present invention, the fibrous elements, for example natural polymer-based fibrous elements, of the present invention may safely comprise active agents that may otherwise create health and/or safety concerns if they become airborne. For example, the fibrous element, for example natural polymer-based fibrous element, may be used to inhibit enzymes within the fibrous element from becoming airborne.

In one example, the fibrous elements, for example natural polymer-based fibrous elements, of the present invention may be meltblown fibrous elements. In another example, the fibrous elements, for example natural polymer-based fibrous elements, of the present invention may be spunbond fibrous elements. In another example, the fibrous elements, for example natural polymer-based fibrous elements, may be hollow fibrous elements prior to and/or after release of one or more of its active agents.

The fibrous elements, for example natural polymer-based fibrous elements, of the present invention may be hydrophilic or hydrophobic. The fibrous elements, for example natural polymer-based fibrous elements, may be surface treated and/or internally treated to change the inherent hydrophilic or hydrophobic properties of the fibrous element.

In one example, the fibrous element, for example natural polymer-based fibrous element and/or plurality of fibrous elements of the present invention exhibits a diameter of less than 100 µm and/or less than 75 µm and/or less than 50 µm and/or less than 25 µm and/or less than 10 µm and/or less than 5 µm and/or less than 1 µm as measured according to the Diameter Test Method described herein. In another example, the fibrous element, for example natural polymer-based fibrous elements and/or plurality of fibrous elements of the present invention exhibits a diameter of greater than 1 µm as measured according to the Diameter Test Method described herein. The diameter of a fibrous element of the present invention may be used to control the rate of release of one or more active agents present in the fibrous element and/or the rate of loss and/or altering of the fibrous element's physical structure.

The fibrous element, for example natural polymer-based fibrous element, may comprise two or more different active agents comprising a surfactant or surfactant mixture and optionally addition non-surfactant active agents. In one example, the fibrous element comprises two or more different active agents, wherein the two or more different active agents are compatible with one another. In another example, the fibrous element comprises two or more different active agents, wherein the two or more different active agents are incompatible with one another.

In one example, the fibrous element, for example natural polymer-based fibrous element, may comprise an active agent comprising a surfactant or surfactant mixture within the fibrous element and an active agent on an external surface of the fibrous element, such as an active agent coating on the fibrous element. The active agent on the external surface of the fibrous element may be the same or different from the active agent present in the fibrous element. If different, the active agents may be compatible or incompatible with one another.

In one example, one or more active agents comprising a surfactant or surfactant mixture and optionally additional non-surfactant active agents may be uniformly distributed or substantially uniformly distributed throughout the fibrous element, for example natural polymer-based fibrous element. In another example, one or more active agents comprising a surfactant or surfactant mixture and optionally additional non-surfactant active agents may be distributed as discrete regions within the fibrous element. In still another example, at least one active agent comprising a surfactant or surfactant mixture and optionally additional non-surfactant active agents is distributed uniformly or substantially uniformly throughout the fibrous element, for example natural polymer-based fibrous element, and at least one other active agent is distributed as one or more discrete regions within the fibrous element. In still yet another example, at least one active agent comprising a surfactant or surfactant mixture and optionally additional non-surfactant active agents is distributed as one or more discrete regions within the fibrous element and at least one other active agent is distributed as one or more discrete regions different from the first discrete regions within the fibrous element.

In one example, the fibrous element, for example natural polymer-based fibrous element and/or a plurality of fibrous elements of the present invention comprise one or more fibrous element-forming materials, for example one or more natural polymer-based fibrous element-forming materials, for example a modified polysaccharide, such as a modified starch, for example an acetylated starch having a DS of from about 0.1 to about 1.0 and/or from about 0.2 to about 0.9 and/or from about 0.2 to about 0.8 and/or from about 0.3 to about 0.7, a weight average molecular weight of from about 25,000 to about 450,000 g/mol and/or from about 35,000 to about 400,000 g/mol and/or from about 35,000 to about 350,000 g/mol and/or from about 45,000 to about 300,000 g/mol and/or from about 50,000 to about 300,000 g/mol and/or from about 50,000 to about 250,000 g/mol, wherein the fibrous element further comprises a surfactant mixture or blend comprising a linear alkyl benzene sulfonate and an alkyl sulfate, wherein the fibrous element is derived from a fibrous element-forming composition exhibiting a viscosity of from about 0.01 Pas to about 1.2 Pas and/or from about 0.02 Pas to about 1.0 Pas as measured according to the Rotational Rheometer Test Method, wherein the fibrous element-forming composition comprises the surfactant mixture and the one or more natural polymer-based fibrous element-forming materials such as acetylated starch at a weight ratio of from about 0.15:1 to about 6:1 and/or from about 0.20:1 to about 5.5:1 and/or from about 0.25:1 to about 5:1 and/or from about 0.5:1 to about 2:1, for example 2:1, wherein the aqueous composition further comprises from about 55% to about 85%, for example about 55%, by weight of water.

In one example, the surfactant and/or surfactant mixture present in the fibrous elements of the present invention may comprise surfactants suitable for beauty care and/or personal care applications such as hand wash, face wash, body wash, shampoo and other hair cleaning and/or conditioning application. Non-limiting examples of surfactants suitable for such beauty care and/or personal care applications include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one example, the surfactant and/or surfactant mixture comprises one or more sulfate-free surfactants and/or 100% sulfate-free surfactants.

In one example, the plurality of fibrous elements of the present invention exhibit an average diameter of less than 50 µm as measured according to the Diameter Test Method.

In one example, the plurality of fibrous elements comprise two or more different fibrous element-forming materials, for example natural polymer-based fibrous element-forming materials.

In one example, the plurality of fibrous elements of the present invention comprise two or more different active agents, at least one of which is a surfactant or surfactant mixture.

In one example, the plurality of fibrous elements of the present invention further comprises a coating composition, for example a coating composition comprising one or more active agents, present on an external surface of the plurality of fibrous elements.

In one example, the plurality of fibrous elements of the present invention exhibits a water content of from 0% to about 20% and/or greater than 0% to less than 15% as measured according to the Water Content Test Method.

The fibrous elements of the present invention are made from a fibrous element-forming composition, for example a filament-forming composition comprising one or more fibrous element-forming materials, for example natural polymer-based fibrous element-forming materials, and one or more active agents comprising a surfactant or surfactant mixture and optionally additional non-surfactant active agents, and optionally a polar solvent, such as water that solubilizes the fibrous element-forming materials and the active agents. In one example, the fibrous element-forming composition comprises a polar solvent, for example water, and one or more fibrous element-forming materials wherein at least one of the one or more fibrous element-forming materials comprises a modified polysaccharide and one or more active agents wherein at least one of the active agents comprises a surfactant, wherein the surfactant and the modified polysaccharide are present within the fibrous element-forming composition at a weight ratio of from about 0.25:1 to about 5:1.

In one example, the surfactant and/or surfactant mixture present in the fibrous element-forming compositions of the present invention may comprise surfactants suitable for beauty care and/or personal care applications such as hand wash, face wash, body wash, shampoo and other hair cleaning and/or conditioning application. Non-limiting examples of surfactants suitable for such beauty care and/or personal care applications include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In one example, the surfactant and/or surfactant mixture comprises one or more sulfate-free surfactants and/or 100% sulfate-free surfactants.

In one example, a method for making a fibrous element, for example a natural polymer-based fibrous element and/or a plurality of fibrous elements of the present invention comprises the steps of:
 a. providing a fibrous element-forming composition comprising one or more fibrous element-forming materials, for example a natural polymer-based fibrous element-forming material such as a modified polysaccharide, for example a modified starch, such as an acetylated starch, and one or more active agents comprising a surfactant or a surfactant mixture comprising a linear alkyl benzene sulfonate and an alkyl sulfate, wherein the fibrous element-forming composition comprises the surfactant or surfactant mixture and the natural polymer-based fibrous element-forming material, such as acetylated starch, at a weight ratio of surfactant or surfactant mixture to natural polymer-based fibrous element-forming material from about 0.5:1 to about 2:1;
 b. spinning the fibrous element-forming composition, for example from a multi-row capillary die, into one or more fibrous elements, for example natural polymer-based fibrous elements and/or a plurality of fibrous elements comprising the natural polymer-based fibrous element-forming material, such as acetylated starch, and the surfactant or surfactant mixture.

In one example, the fibrous element-forming composition comprises a polar solvent, such as water, one or more fibrous element-forming materials, for example natural polymer-based fibrous element-forming materials comprising an acetylated starch, and a surfactant or surfactant mixture comprising a linear alkyl benzene sulfonate and an alkyl sulfate. The fibrous element-forming composition may exhibit a viscosity of from about 0.01 Pas to about 1.2 Pas and/or from about 0.02 Pas to about 1.0 Pas as measured according to the Rotational Rheometer Test Method.

Fibrous Element-Forming Material

The fibrous element-forming material is any suitable natural polymer-based material, such as a modified natural polymer or monomers capable of producing a modified natural polymer that exhibits properties suitable for making a fibrous element, for example natural polymer-based fibrous elements, such as a filament, for example natural polymer based filament, such as by a spinning process.

In one example, the fibrous element-forming material may comprise a polar solvent-soluble natural polymer-based material, such as an alcohol-soluble natural polymer-based material and/or a water-soluble natural polymer-based material.

In another example, the fibrous element-forming material may comprise a non-polar solvent-soluble natural polymer-based material.

In still another example, the fibrous element-forming material may comprise a water-soluble natural polymer-based material and be free (less than 5% and/or less than 3% and/or less than 1% and/or 0% by weight on a dry fibrous element basis and/or dry fibrous structure basis) of water-insoluble materials.

In yet another example, the fibrous element-forming material may be a film-forming natural polymer-based material. In still yet another example, the fibrous element-forming material may be chemically, enzymatically, and/or physically modified.

Non-limiting examples of natural polymer-based fibrous element-forming materials may exhibit a weight average molecular weight of at least 10,000 g/mol and/or at least 20,000 g/mol and/or at least 40,000 g/mol and/or at least 80,000 g/mol and/or at least 100,000 g/mol and/or at least 1,000,000 g/mol and/or at least 3,000,000 g/mol and/or at least 10,000,000 g/mol and/or at least 20,000,000 g/mol to about 40,000,000 g/mol or to about 30,000,000 g/mol.

In one example, the natural polymer-based fibrous element-forming material of the present invention comprises a polysaccharide, for example a modified polysaccharide, such as a modified starch, for example acetylated starch.

"Polysaccharides" as used herein means natural polysaccharides and polysaccharide derivatives and/or modified polysaccharides. Suitable water-soluble polysaccharides include, but are not limited to, starches, starch derivatives, chitosan, chitosan derivatives, cellulose derivatives, hemicellulose, hemicellulose derivatives, gums, arabinans, galactans and mixtures thereof. The water-soluble polysaccharide may exhibit a weight average molecular weight of from about 10,000 to about 40,000,000 g/mol and/or greater than 100,000 g/mol and/or greater than 1,000,000 g/mol and/or greater than 3,000,000 g/mol and/or greater than 3,000,000 to about 40,000,000 g/mol.

The polysaccharides may comprise non-cellulose and/or non-cellulose derivative and/or non-cellulose copolymer water-soluble polysaccharides. Such non-cellulose water-soluble polysaccharides may be selected from the group consisting of: starches, starch derivatives, chitosan, chitosan derivatives, hemicellulose, hemicellulose derivatives, gums, arabinans, galactans, dextrans, and mixtures thereof.

Naturally occurring starch is generally a mixture of linear amylose and branched amylopectin polymer of D-glucose units. The amylose is a substantially linear polymer of D-glucose units joined by (1,4)-α-D links. The amylopectin is a highly branched polymer of D-glucose units joined by (1,4)-α-D links and (1,6)-α-D links at the branch points. Naturally occurring starch typically contains relatively high levels of amylopectin, for example, corn starch (64-80% amylopectin), waxy maize (93-100% amylopectin), rice (83-84% amylopectin), potato (about 78% amylopectin), and wheat (73-83% amylopectin). In one example the naturally occurring starch of the present invention is a high amylopectin natural starch and/or high amylose natural starch derived from agricultural sources. Such agricultural sources offer the advantages of being abundant in supply, easily replenishable, and relatively inexpensive as compared to starches derived from other sources.

As used herein, "starch" includes any naturally occurring unmodified starches, modified starches, synthetic starches and mixtures thereof, as well as mixtures of the amylose or amylopectin fractions; the starch may be modified by physical, chemical, or biological processes, or combinations thereof. The choice of unmodified or modified starch for the present invention may depend on the end product desired. In one example of the present invention, the starch or starch mixture useful in the present invention has an amylopectin content from about 20% to about 100%, more typically from about 40% to about 90%, even more typically from about 60% to about 85% by weight of the starch or mixtures thereof. In another example of the present invention, the starch or starch mixture useful in the present invention has an amylopectin content from about 90% to about 100% and/or from about 95% to about 99% by weight of the starch or mixtures thereof.

Suitable naturally occurring starches can include, but are not limited to, corn starch, potato starch, sweet potato starch, wheat starch, sago palm starch, tapioca starch, rice starch, soybean starch, arrow root starch, amioca starch, bracken starch, lotus starch, waxy maize starch, and high amylose corn starch. Naturally occurring starches particularly, corn starch and wheat starch, are the preferred starch polymers due to their economy and availability.

In one example, in addition to the above, when present, the natural polymer-based material comprises a modified polysaccharide having a solubility parameter of greater than 14.00 to less than 16.25 and/or greater than 14.50 to less than 16.25 and/or greater than 14.50 to less than 16.00 and/or greater than 15.00 to less than 15.50 as determined by Fedors Method described herein.

In one example, in addition to the above, when present, the natural polymer-based material comprises a modified polysaccharide exhibiting a weight average molecular weight of greater than 50,000 to less than 40,000,000 g/mol and/or greater than 50,000 to less than 20,000,000 g/mol and/or greater than 50,000 to less than 10,000,000 g/mol and/or greater than 50,000 to less than 5,000,000 g/mol and/or greater than 50,000 to less than 1,000,000 g/mol and/or greater than 100,000 to less than 750,000 g/mol and/or greater than 125,000 to less than 600,000 g/mol and/or from about 150,000 to about 400,000 g/mol as measured according to the Weight Average Molecular Weight Test Method.

In one example, in addition to the above, when present, the natural polymer-based material comprises a modified polysaccharide exhibiting a charge density of from –0.1 to +0.1 meq/g and/or of about 0 meq/g as measured by the Charge Density Test Method.

In one example, in addition to the above, when present, the natural polymer-based material comprises a modified polysaccharide is selected from the group consisting of: nonionic modified polysaccharides, acetyl-substituted polysaccharides, and mixtures thereof. In one example, the modified polysaccharide comprises a nonionic modified polysaccharide. In one example, the modified polysaccharide comprises an acetyl-substituted polysaccharide, such as an acetylated starch.

In one example, the modified polysaccharide is an acetyl-substituted polysaccharide, such as acetylated starch, exhibiting a DS of at least 0.3 to 1.0 and/or at least 0.3 to 0.7 and/or at least 0.4 to 0.6 and/or about 0.5.

In one example, the modified polysaccharide is derived from starch, for example acid thinned starch and/or enzyme degraded starch and/or waxy starch, such as waxy corn starch, and/or amioca starch.

In one example, the natural polymer-based material comprises a modified polysaccharide, for example a modified starch, such as an acetylated starch (starch acetate), for example an acetylated starch having a DS of from about 0.3 to about 0.7, that exhibits a biodegradability as determined by the OECD 301B Ready Biodegradability $CO_2$ Evolution Test Method of at least 5% and/or at least 10% and/or at least 15% and/or at least 20% and/or at least 25% and/or at least 30% and/or at least 35% and/or at least 40% and/or at least 45% and/or at least 50% and/or at least 55% and/or at least 60% and/or at least 75% and/or at least 80% to about 100% or to about 90% and/or at least 5% to about 100% and/or at least 40% to about 90% on the $28^{th}$ day of the test duration.

In one example, the natural polymer-based material comprises a modified polysaccharide, for example a modified starch, such as an acetylated starch (starch acetate) that exhibits a biodegradability as determined by the OECD 301B Ready Biodegradability $CO_2$ Evolution Test Method of at least 5% and/or at least 10% and/or at least 15% and/or at least 20% and/or at least 25% and/or at least 30% and/or at least 35% and/or at least 40% and/or at least 45% and/or at least 50% and/or at least 55% and/or at least 60% to about 100% or to about 90% and/or at least 5% to about 100% and/or at least 30% to about 90% on the $60^{th}$ day of the test duration.

In one example, the natural polymer-based material comprises a modified polysaccharide, for example a modified starch, such as an acetylated starch (starch acetate) that exhibits a biodegradability as determined by the OECD 301B Ready Biodegradability$CO_2$ Evolution Test Method of at least 5% and/or at least 10% and/or at least 15% and/or at least 20% and/or at least 25% and/or at least 30% and/or at least 35% and/or at least 40% and/or at least 45% and/or at least 50% and/or at least 55% and/or at least 60% and/or at least 65% and/or at least 70% and/or at least 75% and/or at least 80% to about 100% or to about 90% and/or at least 5% to about 100% and/or at least about 50% to about 90% on the $90^{th}$ day of the test duration.

Non-Limiting Examples of Fibrous Element-Forming Materials

Fibrous element-forming materials, for example natural polymer-based fibrous element-forming materials, such as modified polysaccharides, for example modified starches, in this case acetylated starches, some of which were suitable for use in the present invention and others of which were not, were made as follows.

Non-Limiting Examples 1-7

First, amioca starch (starting weight average molecular weight (Mw) in the range of 10,000,000 ("$10^7$") g/mol to 1,000,000,000 ("$10^9$") g/mol and average 100,000,000 ("$10^8$") g/mol commercially available from Ingredion is degraded by acid thinning as follows.

a. Starch Mw Degradation (Acid Thinning)

For the preparation of Examples 1-7, 1 kg of Mw-degraded amioca starch is prepared in a 20 L jacketed Büchi-glas reactor. To 0.5 M sulfuric acid solution, amioca starch was added to achieve a 20 wt % dispersion at about 23° C. The temperature of the dispersion was then raised to 70° C. and the resulting suspension was stirred for 105 minutes at 70° C. The suspension was then cooled to 35° C. After cooling to 35° C., NaOH was added to the suspension to adjust the pH to 7.5±0.5. The resulting Mw-degraded starch was centrifuged and washed with a 70% ethanol/deionized water mixture until the Mw-degraded starch was essentially free of $Na_2SO_4$. Finally the Mw-degraded starch was dried in an oven at 40° C. under reduced pressure. The Mw of each Mw-degraded starch was measured using GPC. The Mw of each Mw-degraded starch is set forth in Table 1 below.

TABLE 1

| Sample | Mw of Mw-Degraded Starch (g/mol) |
|---|---|
| 1 | 83,100 |
| 2 | 83,400 |
| 3 and 6 | 83,100 |
| 4 and 5 | 481,000 |
| 7 | 221,000 | b. Starch Acetylation

Each of the Mw-degraded starches (Samples 1-7) were then acetylated by an acetylation reaction to produce acetylated starches (starch acetates). The conditions for the acetylation reaction are set forth in Table 2 below.

TABLE 2

| Sample | Mol Equivalent Mw-Degraded Starch:Ac$_2$O:NaOH | Reaction temperature [° C.] | Reaction time [min] |
|---|---|---|---|
| 1 | 1:1.2:0.5 | 125 | 180 |
| 2 | 1:1.2:0.5 | 125 | 180 |
| 3 | 1:2.5:0.5 | 125 | 180 |
| 4 | 1:1.2:0.5 | 80 | 180 |
| 5 | 1:4.0:0.5 | 80 | 300 |
| 6 | 1:4.0:0.5 | 80 | 300 |
| 7 | 1:2.5:0.5 | 80 | 180 |

For each of the individual samples, 120 g (0.63 mol, 84.9% dry content) Mw-degraded starch was added to 160 g (1.57 mol) acetic acid anhydride (Ac$_2$O) and stirred at about 23° C. for 30 minutes. Next, 22.6 g (0.28 mol, 50% aq. solution) sodium hydroxide (NaOH) was added dropwise. The temperature of the mixture was raised up to 125° C. (Samples 1-3) and 80° C. (Samples 4-7). The mixture was stirred for 180 minutes (Samples 1-4 and 7) and 300 minutes (Samples 5-6) at its respective elevated temperature. The mixture was then cooled down. The resulting acetylated starch (starch acetate) was precipitated in ethanol and washed with a mixture of water/ethanol=1/9 until the washing liquid was pH-neutral. The acetylated starch was then finally dried under reduced pressure at 40° C.

The resulting acetylated starches (starch acetates) (Samples 1-7) are characterized as set forth in Table 3 below. The sulfur content is determined using a FlashEA 1112 CHNS/O Automatic Elemental Analyzer from Thermo Scientific with MAS200R auto sampler. The sodium content was determined by ICP-OES (inductive coupled plasma-optical emission spectrometry, Perkin Elmer) after a nitric acid digestion by microwave. Salt content: The amount of sodium sulfate was calculated from the sulfur content. Then it was computed how much sodium is bound in sodium sulfate. The excess of sodium was allocated to the amount of sodium acetate.

The Degree of Substitution (DS) of a starch acetate in Table 3 is determined by adding a known amount of starch acetate (150-200 mg) to 10 mL of an acetone/deionized water mixture (1:1 by volume) for 24 hours at about 23° C. Then 5 mL of 1 N NaOH in ethanol is added and the mixture is stirred for a further 24 hours at about 23° C. The excess of alkali is titrated with Y mL of 0.1 N aqueous HCl by potentiometric titration to the equivalence point. The Degree of Substitution (DS) and weight percent substituent can be calculated by the equations below. Moisture content percent is determined using a Mettler Toledo HR-83 or HR-83P Moisture Balance using an approximate 3.5 g sample heated via a standard drying program to 160° C. with a Switch-off-Criterion of 1 mg/50 s. The Degree of Substitution equation is relevant for polyglucosides. For other polymers, replace 162 g/mol with the corresponding monomer molecular weight.

$$\% \text{ Activity} = 100\% - \text{Moisture Content }\%$$

$$\text{Acetyl Content} = \frac{(5 \text{ mL } 1N \text{ NaOH} \times 1.0 \text{ mmol/mL}) - (Y \text{ mL } 0.1N \times 0.1 \text{ mmol/mL})}{\text{Wt. (g) sample titrated} \times \% \text{ Activity}} = \frac{\text{mmol acetyl}}{\text{g sample}}$$

$$\text{Degree of Substitution}(DS) = \frac{162 \text{ g/mol}}{1000 \times (\text{Acetyl Content})^{-1} - 43 \text{ g/mol}}$$

$$\text{Acetyl Weight }\% = \frac{\text{Acetyl Content} \times 43}{1000} \times 100\%$$

TABLE 3

| Sample | Visual Characterization of Starch Acetate | DS | Salt Content (%)[1] Na$_2$SO$_4$ | NaOAc | Mw of Starch Acetate (g/mol) |
|---|---|---|---|---|---|
| 1 | light brownish/beige | 0.32 | 3.3 | 1.8 | 74,100 |
| 2 | brownish | 0.40 | 0.2 | 3.7 | 69,000 |
| 3 | beige | 0.72 | 3.7 | 1.6 | 73,400 |
| 4 | white | 0.10 | 3.0 | 1.6 | 456,000 |
| 5 | white | 1.07 | 2.4 | 0.5 | 423,000 |
| 6 | white | 1.15 | 3.6 | 0.2 | 67,700 |
| 7 | white | 0.53 | 0.8 | 0.7 | 210,000 |

[1]Na$_2$SO$_4$ calculated from S-content; NaOAc (sodium acetate) calculated from Na-content minus Na$_2$SO$_4$ c. Determination of Suitability of Fibrous Element-Forming Material In one example, in order for a fibrous element-forming material, for example a natural polymer-based fibrous element-forming material, such as a modified polysaccharide, for example a modified starch, such as an acetylated starch (starch acetate), to be suitable for use as a fibrous element-forming material in the present invention, for example in the presence of a surfactant in a fibrous element and/or a fibrous element-forming composition, the fibrous element-forming material must exhibit miscibility as determined by the Fibrous Element-forming Material Miscibility Test Method described herein.

For the starch acetates (Samples 1-7), the Fibrous Element-forming Material Miscibility Test Method described herein was run. The results for the starch acetates is set forth below in Table 4. As shown in Table 4, Starch Acetate Samples 1-3 and 7 satisfied the Fibrous Element-forming Material Miscibility Test Method described herein and are thus suitable for forming the fibrous elements of the present invention and/or fibrous element-forming compositions of the present invention. Also as shown in Table 4, Starch Acetate Samples 4-6 failed the Fibrous Element-forming Material Miscibility Test Method described herein and are thus not suitable for forming the fibrous elements of the present invention and/or the fibrous element-forming compositions of the present invention.

In addition to DS and Mw and/or in the alternative, high salt content levels may negatively impact the miscibility of the starch acetates.

TABLE 4

| Starch Acetate Samples | DS | % $Na_2SO_4$ | % NaOAc | Mw (g/mol) | 15% Solids | 30% Solids[1] |
|---|---|---|---|---|---|---|
| 1 | 0.32 | 3.3 | 1.8 | 74,100 | 1 phase | 1 phase |
| 2 | 0.4 | 0.2 | 3.7 | 69,000 | 1 phase | 1 phase |
| 3 | 0.72 | 3.7 | 1.6 | 73,400 | 1 phase | 1 phase |
| 4 | 0.1 | 3 | 1.6 | 456,000 | 1 phase | 2 phase |
| 5 | 1.07 | 2.4 | 0.5 | 423,000 | Insoluble Starch | Insoluble Starch |
| 6 | 1.15 | 3.6 | 0.2 | 67,700 | Insoluble Starch | Insoluble Starch |
| 7 | 0.53 | 0.8 | 0.7 | 210,000 | 1 phase | 1 phase |

Non-Limiting Example 8

First, amioca starch (starting weight average molecular weight (Mw) in the range of 10,000,000 ("$10^7$") g/mol to 1,000,000,000 ("$10^9$") g/mol and average 100,000,000 ("$10^8$") g/mol commercially available from Ingredion is degraded by acid thinning as follows.

a. Starch Mw Degradation (Acid Thinning)

For the preparation of 8 kg of Mw-degraded amioca starch a 30 L jacketed Büchi-glas reactor is used. To 0.27 M sulfuric acid solution, amioca starch is added to achieve a 40 wt % dispersion at about 23° C. The temperature of the dispersion is then raised to 50° C. and the resulting suspension is stirred for 36 hours at 50° C. The suspension is then cooled to 25° C. After cooling to 25° C., NaOH is added to the suspension to adjust the pH to 7.5±0.5. The resulting Mw-degraded starch is filtered and dried in an oven at 50° C. under reduced pressure (60 mbar).

b. Starch Acetylation

The Mw-degraded starch is then acetylated by an acetylation reaction to produce acetylated starch (starch acetate).

To a 30 L jacketed Büchi-glas reactor add in 9 liters of deionized water and 2.5 kg of Mw-degraded starch from Step a. Cool to 10° C. and stir resulting slurry to disperse. Adjust to pH 9 using NaOH. Over 1 hour, pump in 1.88 kg acetic anhydride ($Ac_2O$) and 3.6 kg 25% NaOH solution. Maintain pH 8-9 during the addition. After addition is finished, set temperature to 25° C. Stir for 4 hours. The pH will gradually drop as the acetylation reaction continues. Periodically add in NaOH to maintain pH 8-9. Add in 6 liters of ethanol to precipitate the acetylated starch (starch acetate). Allow to settle overnight. Siphon off supernatant liquid and add in 6 liters of ethanol. Stir to disperse and filter. Dry the starch acetate under reduced pressure (60 mbar) at 50° C.

Active Agents

Active agents are a class of additives that are designed and intended to provide a benefit to something other than the fibrous element and/or particle and/or fibrous structure itself, such as providing a benefit to an environment external to the fibrous element and/or particle and/or fibrous structure. Active agents may be any suitable additive that produces an intended effect under intended use conditions of the fibrous element. For example, the active agent may be selected from the group consisting of: personal cleansing and/or conditioning agents such as hair care agents such as shampoo agents and/or hair colorant agents, hair conditioning agents, skin care agents, sunscreen agents, and skin conditioning agents; laundry care and/or conditioning agents such as fabric care agents, fabric conditioning agents, fabric softening agents, fabric anti-wrinkling agents, fabric care anti-static agents, fabric care stain removal agents, soil release agents, dispersing agents, suds suppressing agents, suds boosting agents, anti-foam agents, and fabric refreshing agents; liquid and/or powder dishwashing agents (for hand dishwashing and/or automatic dishwashing machine applications), hard surface care agents, and/or conditioning agents and/or polishing agents; other cleaning and/or conditioning agents such as antimicrobial agents, antibacterial agents, antifungal agents, fabric hueing agents, perfume, bleaching agents (such as oxygen bleaching agents, hydrogen peroxide, percarbonate bleaching agents, perborate bleaching agents, chlorine bleaching agents), bleach activating agents, chelating agents, builders, lotions, brightening agents, air care agents, carpet care agents, dye transfer-inhibiting agents, clay soil removing agents, anti-redeposition agents, polymeric soil release agents, polymeric dispersing agents, alkoxylated polyamine polymers, alkoxylated polycarboxylate polymers, amphiphilic graft copolymers, dissolution aids, buffering systems, water-softening agents, water-hardening agents, pH adjusting agents, enzymes, flocculating agents, effervescent agents, preservatives, cosmetic agents, make-up removal agents, lathering agents, deposition aid agents, coacervate-forming agents, clays, thickening agents, latexes, silicas, drying agents, odor control agents, antiperspirant agents, cooling agents, warming agents, absorbent gel agents, anti-inflammatory agents, dyes, pigments, acids, and bases; liquid treatment active agents; agricultural active agents; industrial active agents; ingestible active agents such as medicinal agents, oral care agents, such as teeth whitening agents, tooth care agents, mouthwash agents, and periodontal gum care agents, edible agents, dietary agents, vitamins, minerals; water-treatment agents such as water clarifying and/or water disinfecting agents, and mixtures thereof.

Non-limiting examples of suitable cosmetic agents, skin care agents, skin conditioning agents, hair care agents, and hair conditioning agents are described in CTFA Cosmetic Ingredient Handbook, Second Edition, The Cosmetic, Toiletries, and Fragrance Association, Inc. 1988, 1992.

One or more classes of chemicals may be useful for one or more of the active agents listed above. For example, surfactants may be used for any number of the active agents described above. Likewise, bleaching agents may be used for fabric care, hard surface cleaning, dishwashing and even teeth whitening. Therefore, one of ordinary skill in the art will appreciate that the active agents will be selected based upon the desired intended use of the fibrous element and/or particle and/or fibrous structure made therefrom.

For example, if the fibrous element and/or particle and/or fibrous structure made therefrom is to be used for hair care and/or conditioning then one or more suitable surfactants, such as a lathering surfactant could be selected to provide the desired benefit to a consumer when exposed to conditions of intended use of the fibrous element and/or particle and/or fibrous structure incorporating the fibrous element and/or particle.

In one example, if the fibrous element and/or particle and/or fibrous structure made therefrom is designed or intended to be used for laundering clothes in a laundry operation, then one or more suitable surfactants and/or enzymes and/or builders and/or perfumes and/or suds suppressors and/or bleaching agents could be selected to provide the desired benefit to a consumer when exposed to conditions of intended use of the fibrous element and/or particle and/or fibrous structure incorporating the fibrous element and/or particle. In another example, if the fibrous element and/or particle and/or fibrous structure made therefrom is designed to be used for laundering clothes in a laundry operation and/or cleaning dishes in a dishwashing operation, then the fibrous element and/or particle and/or fibrous structure may comprise a laundry detergent composition or dishwashing detergent composition or active agents used in such compositions.

In one example, the active agent comprises a non-perfume active agent. In another example, the active agent comprises a non-surfactant active agent, for example one or more non-surfactant active agents selected from the group consisting of: skin care active agents, medicinal agents, lotions, fabric care active agents, dishwashing active agents, carpet care active agents, surface care active agents, hair care active agents, air care active agents, tooth care active agents, and mixtures thereof. In still another example, the active agent comprises a non-ingestible active agent, in other words an active agent other than an ingestible active agent.

Surfactants

Non-limiting examples of suitable surfactants include anionic surfactants, cationic surfactants, nonionic surfactants, zwitterionic surfactants, amphoteric surfactants, and mixtures thereof. Co-surfactants may also be included in the fibrous elements and/or particles. For fibrous elements and/or particles designed for use as laundry detergents and/or dishwashing detergents, the total level of surfactants should be sufficient to provide cleaning including stain and/or odor removal, and generally ranges from about 0.5% to about 95%. Further, surfactant systems comprising two or more surfactants that are designed for use in fibrous elements and/or particles for laundry detergents and/or dishwashing detergents may include all-anionic surfactant systems, mixed-type surfactant systems comprising anionic-nonionic surfactant mixtures, or nonionic-cationic surfactant mixtures or low-foaming nonionic surfactants.

The surfactants herein can be linear or branched. In one example, suitable linear surfactants include those derived from agrochemical oils such as coconut oil, palm kernel oil, soybean oil, or other vegetable-based oils.

In one example, the surfactants, for example for use as hair care active agents, present in the fibrous element-forming composition, the fibrous element, particle, and/or fibrous structure made therefrom may be selected from the group consisting of: sodium lauryl sulfate, sodium laureth sulfate, linear alkylbenzene sulfonate, sodium lauroyl sarcosinate, for example Hamposyl L-30, sodium lauroyl glycinate, lauryl betaine, lauryl hydroxysultaine, sodium lauryl isethionate, cocamide monoethanolamine, decyl glucoside, disodium cocoyl glutamate (DSCG), and mixtures thereof.

a. Anionic Surfactants

The anionic surfactants for use as active agents in the present invention may comprise at least one glutamate surfactant according to the general formula (I):

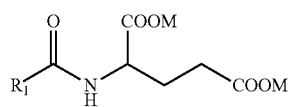

(I)

wherein $R_1$ is a saturated or unsaturated, straight or branched alkyl or alkenyl chain with from 5 to 20 carbon atoms and/or from 7 to 17 carbon atoms and/or from 9 to 13 carbon atoms; and M is independently H, ammonium, triethanolammonium (TEA), sodium or potassium and mixtures thereof.

In one example, when the fibrous element and/or particle and/or fibrous structure made therefrom comprises a glutamate surfactant, the fibrous element and/or particle and/or fibrous structure made therefrom is substantially free of (less than 5% or less than 3% or less than 1% or less than 0.5% or less than 0.1% by weight) or free of (0% by weight) of alkyl sulfate-based and alkyl ether sulfate-based surfactants.

The glutamate surfactant may selected from the group consisting of: sodium cocoyl glutamate, disodium cocoyl glutamate, potassium cocoyl glutamate, dipotassium cocoyl glutamate, ammonium cocoyl glutamate, diammonium cocoyl glutamate, sodium lauroyl glutamate, disodium lauroyl glutamate, potassium lauroyl glutamate, dipotassium lauroyl glutamate, sodium capryloyl glutamate, disodium capryloyl glutamate, potassium capryloyl glutamate, dipotassium capryloyl glutamate, sodium undecylenoyl glutamate, disodium undecylenoyl glutamate, potassium undecylenoyl glutamate, dipotassium undecylenoyl glutamate, disodium hydrogenated tallowoyl glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, sodium cocoyl/hydrogenated tallowoyl glutamate, sodium cocoyl/palmoyl/sunfloweroyl glutamate, sodium hydrogenated tallowoyl glutamate, sodium olivoyl glutamate, disodium olivoyl glutamate, sodium palmoyl glutamate, disodium palmoyl glutamate, TEA-cocoyl glutamate, TEA-hydrogenated tallowoyl glutamate, TEA-lauroyl glutamate, and mixtures thereof.

The fibrous element and/or particle and/or fibrous structure made therefrom may comprise at least one glutamate surfactant selected from the group consisting of: sodium cocoyl glutamate, disodium cocoyl glutamate, potassium cocoyl glutamate, dipotassium cocoyl glutamate, ammonium cocoyl glutamate, diammonium cocoyl glutamate, sodium lauroyl glutamate, disodium lauroyl glutamate, potassium lauroyl glutamate, dipotassium lauroyl glutamate, sodium capryloyl glutamate, disodium capryloyl glutamate, potassium capryloyl glutamate, dipotassium capryloyl glutamate, sodium stearoyl glutamate, disodium stearoyl glutamate, potassium stearoyl glutamate, dipotassium stearoyl glutamate, sodium myristoyl glutamate, disodium myristoyl glutamate, potassium myristoyl glutamate, dipotassium myristoyl glutamate, TEA-cocoyl glutamate, and mixtures thereof The fibrous element and/or particle and/or fibrous structure made therefrom may comprise at least one glutamate surfactant selected from the group consisting of: sodium cocoyl glutamate, disodium cocoyl glutamate, potassium cocoyl glutamate, dipotassium cocoyl glutamate, ammonium cocoyl glutamate, diammonium cocoyl glutamate, TEA-cocoyl glutamate, and mixtures thereof.

In one example, non-limiting examples of surfactants, for example for use as hair care active agents, may be selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and mixtures thereof.

The total level of one or more glutamate surfactants present in the fibrous element-forming composition, the fibrous element and/or particle and/or fibrous structure made therefrom may be from about 20% to about 95% and/or from about 25% to about 90% and/or from about 30% to about 70% by weight of the fibrous element-forming composition or the fibrous element and/or particle and/or fibrous structure basis.

The one or more surfactants of the one or more active agents may also comprise a co-surfactant by weight of the fibrous element-forming composition, wherein the co-surfactant is selected from the group consisting of: a non-glutamate anionic surfactant, a nonionic surfactant, a zwitterionic surfactant, an amphoteric surfactant, and mixtures thereof.

The total level of one or more co-surfactants, when present in the fibrous element-forming composition, the fibrous element and/or particle and/or fibrous structure made therefrom maybe from about 2% to about 30% and/or from about 5% to about 25% and/or from about 7% to about 20% by weight of the fibrous element-forming composition, the fibrous element and/or particle and/or fibrous structure basis.

Non-limiting examples of non-glutamate anionic surfactants present alone or in combination with a glutamate surfactant or other surfactants may include anionic surfactants selected from the group consisting of: an isethionate surfactant, a sarcosinate surfactant, a glycinate surfactant, an alanitate surfactant, a sulfosuccinate surfactant, a sulfonate surfactant, a sulfoacetate surfactant, a glucose carboxylate surfactant, an alkyl ether carboxylate surfactant, a taurate surfactant, and mixtures thereof. Each anionic surfactant just listed above will be described in more details below.

Non-limiting examples of non-glutamate anionic surfactants present alone or in combination with one or more glutamate surfactants or other surfactants may include anionic surfactants selected from the group consisting of: a lactate surfactant, a lactylate surfactant, and mixtures thereof. A non-limiting example of a lactate surfactant includes sodium lactate. Non-limiting examples of a lactylate surfactant includes sodium lauroyl lactylate, sodium cocoyl lactylate, and mixture thereof.

The one or more active agents may also comprise one or more surfactants comprising at least one isethionate surfactant according to the general formula (II):

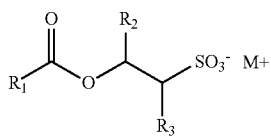

(II)

wherein $R_1$ is a saturated or unsaturated, straight or branched, alkyl or alkenyl chain with from 6 to 30 carbon atoms, from 8 to 22 and/or 9 to 18 carbon atoms, $R_2$ and $R_3$ are each independently H or ($C_1$-$C_4$) alkyl, for example methyl, and mixtures thereof, and $M^+$ is an alkali metal, for example lithium, sodium, potassium; or $M^+$ is an alkali-earth metal, for example magnesium; or $M^+$ is an ammonium or a substituted ammonium cation.

The isethionate surfactant may be selected from the group consisting of: sodium lauroyl isethionate, sodium lauroyl methyl isethionate, sodium oleoyl isethionate, sodium oleoyl methyl isethionate, sodium stearoyl isethionate, sodium stearoyl methyl isethionate, sodium myristoyl isethionate, sodium myristoyl methyl isethionate, sodium palmitoyl isethionate, sodium palmitoyl methyl isethionate, sodium cocoyl isethionate, sodium cocoyl methyl isethionate, a blend of stearic acid and sodium cocoyl isethionate, ammonium cocoyl isethionate, ammonium cocoyl methyl isethionate, and mixtures thereof.

The isethionate surfactant may be selected from the group consisting of: sodium lauroyl isethionate, sodium lauroyl methyl isethionate, sodium oleoyl isethionate, sodium stearoyl isethionate, sodium myristoyl isethionate, sodium palmitoyl isethionate, sodium cocoyl isethionate, ammonium cocoyl isethionate, and mixtures thereof.

The isethionate surfactant may be selected from the group consisting of: sodium lauroyl isethionate, sodium lauroyl methyl isethionate, sodium stearoyl isethionate, sodium myristoyl isethionate, sodium cocoyl isethionate, ammonium cocoyl isethionate, and mixtures thereof.

The isethionate surfactant may be selected from the group consisting of: sodium lauroyl isethionate, sodium cocoyl isethionate, ammonium cocoyl isethionate, and mixtures thereof.

Corresponding commercial products are available, for example, from the company Innospec under the trade name "Iselux®" and from Clariant or Uniquema under the trade names "Hostapon®" or "Arlatone®". Examples of other commercial fatty acyl isethionates that may be used can be Hostapon® surfactants from Clariant such as for sodium cocoyl isethionate: Hostapon® SCI-85C, Hostapon® SCI-78C, or a blend of stearic acid with sodium cocoyl isethionate: Hostapon® SCI-65C. Examples of other commercial fatty acyl isethionates that may be used can be "Jordapon®" surfactants from BASF such as Jordapon® CI prill or Jordapon® CI65; and sodium cocoyl isethionate from Yongan Daily Chemical Co. such as YA-SCI-85® or YA-SCI-65®.

The sarcosinate surfactant may have the general formula (III):

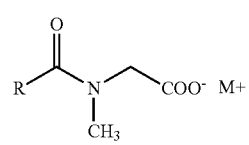

(III)

wherein R is a saturated or unsaturated, straight or branched alkyl or alkenyl, for example an alkyl chain with 7 to 17 and/or 9 to 13 carbon atoms, and $M^+$ is H to form —COOH or $M^+$ is a sodium, potassium, ammonium or triethanolammonium cation.

The one or more active agents may comprise a sarcosinate surfactant. The sarcosinate surfactant may be selected from the group consisting of: sodium lauroyl sarcosinate, sodium cocoyl sarcosinate, sodium myristoyl sarcosinate, TEA-cocoyl sarcosinate, ammonium cocoyl sarcosinate, ammonium lauroyl sarcosinate, dimer dilinoleyl bis-lauroyl glutamate/lauroyl sarcosinate, disodium lauroamphodiacetate, lauroyl sarcosinate, isopropyl lauroyl sarcosinate, potassium cocoyl sarcosinate, potassium lauroyl sarcosinate, sodium cocoyl sarcosinate, sodium lauroyl sarcosinate, sodium myristoyl sarcosinate, sodium oleoyl sarcosinate, sodium palmitoyl sarcosinate, TEA-cocoyl sarcosinate, TEA-lauroyl sarcosinate, TEA-oleoyl sarcosinate, TEA-palm kernel sarcosinate, and mixtures thereof.

The sarcosinate surfactant may be selected from the group consisting of: sodium lauroyl sarcosinate, sodium myristoyl sarcosinate, sodium cocoyl sarcosinate, and mixtures thereof.

The one or more active agents may include a glycinate surfactant. The glycinate surfactant may be selected from the group consisting of: sodium cocoyl glycinate, sodium lauroyl glycinate, and mixture thereof.

The one or more active agents may include an alaninate surfactant. The alaninate surfactant may be selected from the group consisting of: sodium cocoyl alaninate, sodium lauroyl alaninate, sodium N-dodecanoyl-1-alaninate, and mixture thereof.

The one or more active agents may include a sulfosuccinate surfactant. The sulfosuccinate surfactant may be selected from the group consisting of: disodium N-octadecyl sulfosuccinate, disodium lauryl sulfosuccinate, diammonium lauryl sulfosuccinate, sodium lauryl sulfosuccinate, disodium laureth sulfosuccinate, tetrasodium N-(1,2-dicarboxyethyl)-N-octadecyl sulfosuccinnate, diamyl ester of sodium sulfosuccinic acid, dihexyl ester of sodium sulfosuccinic acid, dioctyl esters of sodium sulfosuccinic acid, and mixtures thereof.

The one or more active agents may include a sulfonate surfactant. The sulfonate surfactant may be selected from the group consisting of: alpha olefin sulfonates, linear alkylbenzene sulfonates, sodium laurylglucosides hydroxypropylsulfonate, and mixtures thereof.

The one or more surfactants may include a sulfoacetate surfactant. The sulfoacetate surfactant may be selected from the group consisting of: sodium lauryl sulfoacetate, ammonium lauryl sulfoacetate, and mixture thereof.

The one or more active agents may include a glucose carboxylate surfactant. The glucose carboxylate surfactant may be selected from the group consisting of: sodium lauryl glucoside carboxylate, sodium cocoyl glucoside carboxylate, and mixtures thereof.

The one or more active agents may include an alkyl ether carboxylate surfactant. The akyl ether carboxylate surfactant may be selected from the group consisting of: sodium laureth-4 carboxylate, laureth-5 carboxylate, laureth-13 carboxylate, sodium C12-13 pareth-8 carboxylate, sodium C12-15 pareth-8 carboxylate and mixtures thereof.

The one or more active agents may include a taurate surfactant. The taurate surfactant may be selected from the group consisting of: sodium methyl cocoyl taurate, sodium methyl lauroyl taurate, sodium methyl oleoyl taurate, and mixtures thereof.

The total level of the non-glutamate anionic surfactants present in the fibrous element-forming composition, the fibrous element, particle, and/or fibrous structure made therefrom may be from about 0.5% to about 20% and/or from about 0.5% to about 15% and/or from about 1% to about 10% by weight of the fibrous element-forming composition, the fibrous element and/or particle and/or fibrous structure made therefrom.

Non-limiting examples of suitable anionic surfactants include alkyl sulfates, alkyl ether sulfates, branched alkyl sulfates, branched alkyl alkoxylates, branched alkyl alkoxylate sulfates, mid-chain branched alkyl aryl sulfonates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

Alkyl sulfates and alkyl ether sulfates suitable for use herein include materials with the respective formula $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine. Other suitable anionic surfactants are described in McCutcheon's Detergents and Emulsifiers, North American Edition (1986), Allured Publishing Corp. and McCutcheon's, Functional Materials, North American Edition (1992), Allured Publishing Corp.

In one example, anionic surfactants useful in the fibrous elements and/or particles of the present invention include $C_9$-$C_{15}$ alkyl benzene sulfonates (LAS), $C_8$-$C_{20}$ alkyl ether sulfates, for example alkyl poly(ethoxy) sulfates, $C_8$-$C_{20}$ alkyl sulfates, and mixtures thereof. Other anionic surfactants include methyl ester sulfonates (MES), secondary alkane sulfonates, methyl ester ethoxylates (MEE), sulfonated estolides, and mixtures thereof.

In another example, the anionic surfactant is selected from the group consisting of: $C_{11}$-$C_{18}$ alkyl benzene sulfonates ("LAS") and primary, branched-chain and random $C_{10}$-$C_{20}$ alkyl sulfates ("AS"), $C_{10}$-$C_{18}$ secondary (2,3) alkyl sulfates of the formula $CH_3(CH_2)_x(CHOSO_3^-M^+)$ $CH_3$ and $CH_3(CH_2)_y(CHOSO_3^-M^+)$ $CH_2CH_3$ where x and (y+1) are integers of at least about 7, preferably at least about 9, and M is a water-solubilizing cation, especially sodium, unsaturated sulfates such as oleyl sulfate, the $C_{10}$-$C_{18}$ alpha-sulfonated fatty acid esters, the $C_{10}$-$C_{18}$ sulfated alkyl polyglycosides, the $C_{10}$-$C_{18}$ alkyl alkoxy sulfates ("AE$_x$S") wherein x is from 1-30, and $C_{10}$-$C_{18}$ alkyl alkoxy carboxylates, for example comprising 1-5 ethoxy units, mid-chain branched alkyl sulfates as discussed in U.S. Pat. Nos. 6,020,303 and 6,060,443; mid-chain branched alkyl alkoxy sulfates as discussed in U.S. Pat. Nos. 6,008,181 and 6,020,303; modified alkylbenzene sulfonate (MLAS) as discussed in WO 99/05243, WO 99/05242 and WO 99/05244; methyl ester sulfonate (MES); and alpha-olefin sulfonate (AOS).

In one example, the anionic surfactant is selected from the group consisting of: sulfate-containing anionic surfactants, and sulfate-free anionic surfactants and mixtures thereof.

b. Cationic Surfactants

Non-limiting examples of suitable cationic surfactants include, but are not limited to, those having the formula (I):

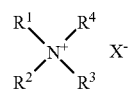

I in which $R^1$, $R^2$, $R^3$, and $R^4$ are each independently selected from (a) an aliphatic group of from 1 to 26 carbon atoms, or (b) an aromatic, alkoxy, polyoxyalkylene, alkylcarboxy, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate, nitrate, sulphate, and alkylsulphate radicals. In one example, the alkylsulphate radical is methosulfate and/or ethosulfate.

Suitable quaternary ammonium cationic surfactants of general formula (I) may include cetyltrimethylammonium chloride, behenyltrimethylammonium chloride (BTAC), stearyltrimethylammonium chloride, cetylpyridinium chloride, octadecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, didecyldimehtylammonium chloride, dioctadecyldimethylammonium chloride, distearyldimethylammonium chloride, tallowtrimethylammonium chloride, cocotrimethylammonium chloride, 2-ethylhexylstearyldimethylammonum chloride, dipalmitoylethyldimethylammonium chloride, ditallowoylethyldimethylammonium chloride, distearoylethyldimethylammonium methosulfate, PEG-2 oleylammonium chloride and salts of these, where the chloride is replaced by halogen, (e.g., bromide), acetate, citrate, lactate, glycolate, phosphate nitrate, sulphate, or alkylsulphate.

Non-limiting examples of suitable cationic surfactants are commercially available under the trade names ARQUAD® from Akzo Nobel Surfactants (Chicago, IL).

In one example, suitable cationic surfactants include quaternary ammonium surfactants, for example that have up to 26 carbon atoms include: alkoxylate quaternary ammonium (AQA) surfactants as discussed in U.S. Pat. No. 6,136,769; dimethyl hydroxyethyl quaternary ammonium as discussed in U.S. Pat. No. 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239, 660 4,260,529 and U.S. Pat. No. 6,022,844; and amino surfactants as discussed in U.S. Pat. No. 6,221,825 and WO 00/47708, for example amido propyldimethyl amine (APA).

In one example the cationic ester surfactants are hydrolyzable under the conditions of a laundry wash.

c. Nonionic Surfactants

The one or more active agents may comprise a nonionic surfactant. The nonionic surfactant may be selected from the group consisting of: alkyl polyglucosides (also referred to as alkyl glycosides), acyl glucamides and mixtures thereof. With respect to the nonionic surfactants, "alkyl" is defined as a saturated or unsaturated, straight or branched alkyl chain with 6 to 30 and/or 8 to 22 and/or 9 to 18 carbon atoms; "acyl" is defined as R—C(O)—, wherein R is a saturated or unsaturated, straight or branched alkyl or alkenyl, for example alkyl chain with 6 to 30 and/or 8 to 22 and/or 9 to 18 carbon atoms.

Non-limiting examples of alkyl polyglucosides include alkyl polyglucosides selected from the group consisting of: decyl glucoside, cocoyl glucoside, lauroyl glucoside, and mixtures thereof.

Non-limiting examples of acyl glucamides including acyl glucamides selected from the group consisting of: lauroyl/myristoyl methyl glucamide, capryloyl/caproyl methyl glucamide, cocoyl methyl glucamide and mixtures thereof.

Non-limiting examples of nonionic surfactants include nonionic surfactants selected from the group consisting of: cocoamide monoethanolamine, lauramide monoethanolamine, cocoyl glucoside, lauroyl glucoside, decyl glucoside, and mixtures thereof.

The total level of the nonionic surfactants present in the fibrous element-forming composition, the fibrous element, particle, and/or fibrous structure made therefrom may be from about 0.1% to about 10% and/or from about 0.1 to about 5% and/or from about 0.5% to about 3% by weight of the fibrous element-forming composition, present in the fibrous element-forming composition, the fibrous element, particle, and/or fibrous structure made therefrom.

Non-limiting examples of suitable nonionic surfactants include alkoxylated alcohols (AE's) and alkyl phenols, polyhydroxy fatty acid amides (PFAA's), alkyl polyglycosides (APG's), $C_{10}$-$C_{18}$ glycerol ethers, and the like.

In one example, non-limiting examples of nonionic surfactants useful in the present invention include: $C_{12}$-$C_{18}$ alkyl ethoxylates, such as, NEODOL® nonionic surfactants from Shell; $C_6$-$C_{12}$ alkyl phenol alkoxylates wherein the alkoxylate units are a mixture of ethyleneoxy and propyleneoxy units; $C_{12}$-$C_{18}$ alcohol and $C_6$-$C_{12}$ alkyl phenol condensates with ethylene oxide/propylene oxide block alkyl polyamine ethoxylates such as PLURONIC® from BASF; $C_{14}$-$C_{22}$ mid-chain branched alcohols, BA, as discussed in U.S. Pat. No. 6,150,322; $C_{14}$-$C_{22}$ mid-chain branched alkyl alkoxylates, $BAE_x$, wherein x is from 1-30, as discussed in U.S. Pat. Nos. 6,153,577, 6,020,303 and 6,093,856; alkylpolysaccharides as discussed in U.S. Pat. No. 4,565,647 Llenado, issued Jan. 26, 1986; specifically alkylpolyglycosides as discussed in U.S. Pat. Nos. 4,483, 780 and 4,483,779; polyhydroxy detergent acid amides as discussed in U.S. Pat. No. 5,332,528; and ether capped poly(oxyalkylated) alcohol surfactants as discussed in U.S. Pat. No. 6,482,994 and WO 01/42408.

Examples of commercially available nonionic surfactants suitable for the present invention include: Tergitol® 15-S-9 (the condensation product of $C_{11}$-$C_{15}$ linear alcohol with 9 moles ethylene oxide) and Tergitol® 24-L-6 NMW (the condensation product of $C_{12}$-$C_{14}$ primary alcohol with 6 moles ethylene oxide with a narrow molecular weight distribution), both marketed by Dow Chemical Company; Neodol® 45-9 (the condensation product of $C_{14}$-$C_{15}$ linear alcohol with 9 moles of ethylene oxide), Neodol® 23-3 (the condensation product of $C_{12}$-$C_{13}$ linear alcohol with 3 moles of ethylene oxide), Neodol® 45-7 (the condensation product of $C_{14}$-$C_{15}$ linear alcohol with 7 moles of ethylene oxide) and Neodol® 45-5 (the condensation product of $C_{14}$-$C_{15}$ linear alcohol with 5 moles of ethylene oxide) marketed by Shell Chemical Company; Kyro® EOB (the condensation product of $C_{13}$-$C_{15}$ alcohol with 9 moles ethylene oxide), marketed by The Procter & Gamble Company; and Genapol LA O3O or O5O (the condensation product of $C_{12}$-$C_{14}$ alcohol with 3 or 5 moles of ethylene oxide) marketed by Clariant. The nonionic surfactants may exhibit an HLB range of from about 8 to about 17 and/or from about 8 to about 14. Condensates with propylene oxide and/or butylene oxides may also be used.

Polyethylene, polypropylene, and polybutylene oxide condensates of alkyl phenols are also suitable for use as a nonionic surfactant in the present invention. These compounds include the condensation products of alkyl phenols having an alkyl group containing from about 6 to about 14 carbon atoms, in either a straight-chain or branched-chain configuration with the alkylene oxide. Commercially available nonionic surfactants of this type include Igepal® CO-630, marketed by Solvay-Rhodia; and Triton® X-45, X-114, X-100 and X-102, all marketed by the Dow Chemical Company.

In one example, non-limiting examples of surfactants, for example for use as hair care active agents, may include nonionic surfactants suitable for use in structured aqueous cleansing phase and include condensation products of alkylene oxide groups (hydrophilic in nature) with an organic hydrophobic compound, which may be aliphatic or alkyl aromatic in nature.

For automatic dishwashing applications, low foaming nonionic surfactants may be used. Suitable low foaming nonionic surfactants are disclosed in U.S. Pat. No. 7,271,138 col. 7, line 10 to col. 7, line 60.

Examples of other suitable nonionic surfactants are the commercially-available Pluronic® surfactants, marketed by BASF, the commercially available Tetronic® compounds, marketed by BASF, and the commercially available Plurafac® surfactants, marketed by BASF.

d. Zwitterionic Surfactants

Non-limiting examples of zwitterionic surfactants include: derivatives of aliphatic quaternary ammonium, quaternary phosphonium or tertiary sulfonium compounds. See U.S. Pat. No. 3,929,678 at column 19, line 38 through column 22, line 48, for examples of zwitterionic surfactants; betaines, including alkyl dimethyl betaine and cocodimethyl amidopropyl betaine, $C_8$ to $C_{18}$ (for example from $C_{10}$ to $C_{18}$ or $C_{12}$ to $C_{18}$) amine oxides and sulfo and hydroxy betaines, such as N-alkyl-N,N-dimethylammino-1-propane sulfonate where the alkyl group can be $C_8$ to $C_{18}$ and in certain embodiments from $C_{10}$ to $C_{14}$.

Zwitterionic surfactants suitable for use alone or as a co-surfactant may include those that are broadly described as derivatives of aliphatic quaternary ammonium, phosphonium, and sulfonium compounds, in which the aliphatic radicals can be straight or branched chains, and wherein one of the aliphatic substituents can contain from 8 to 18 carbon atoms and one can contain an anionic group, e.g., carboxy, sulfonate, phosphate, or phosphonate.

The zwitterionic surfactants may comprise betaine zwitterionic surfactants. Non-limiting examples of betaine zwitterionic surfactants may be selected from the group consisting of: coco dimethyl carboxymethyl betaine, cocoamidopropyl betaine (CAPB), coco-betaine, lauryl amidopropyl betaine (LAPB), oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. Examples of sulfobetaines may include coco dimethyl sulfopropyl betaine, stearyl dimethyl sulfopropyl betaine, lauryl dimethyl sulfoethyl betaine, lauryl bis-(2-hydroxyethyl) sulfopropyl betaine and mixtures thereof.

In one example, non-limiting examples of surfactants, for example for use as hair care active agents, may be selected from the group consisting of: betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gammacarboxypropyl betaine, and lauryl bis-(2-hydroxypropyl)alpha-carboxyethyl betaine, sulfobetaines, for example coco dimethyl sulfopropyl betaine, stearyl dimethyl sulfopropyl betaine, lauryl dimethyl sulfoethyl betaine, lauryl bis-(2-hydroxyethyl) sulfopropyl betaine, amidobetaines and amidosulfobetaines, for example wherein the $RCONH(CH_2)_3$ radical in the amidobetaines and amidosulfobetaines is attached to the nitrogen atom of the betaine, and mixtures thereof.

e. Amphoteric Surfactants

Non-limiting examples of amphoteric surfactants include: aliphatic derivatives of secondary or tertiary amines, or aliphatic derivatives of heterocyclic secondary and tertiary amines in which the aliphatic radical can be straight- or branched-chain and mixtures thereof. One of the aliphatic substituents may contain at least about 8 carbon atoms, for example from about 8 to about 18 carbon atoms, and at least one contains an anionic water-solubilizing group, e.g. carboxy, sulfonate, sulfate. See U.S. Pat. No. 3,929,678 at column 19, lines 18-35, for suitable examples of amphoteric surfactants.

Amphoteric surfactants can include those that can be broadly described as derivatives of aliphatic secondary and tertiary amines in which an aliphatic radical can be straight or branched chain and wherein an aliphatic substituent can contain from 8 to 18 carbon atoms such that one carbon atom can contain an anionic water solubilizing group, e.g., carboxy, sulfonate, phosphate, or phosphonate. Examples of compounds falling within this definition can be sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378.

The amphoteric surfactant described herein may preferably selected from the group consisting of: sodium lauroamphoacetate, sodium cocoamphoacetate, disodium lauroamphodiacetate, disodium cocodiamphoacetate, and mixtures thereof.

Suitable amphoteric or zwitterionic surfactants can include those described in U.S. Pat. Nos. 5,104,646 and 5,106,609.

Hence, the one or more surfactants of the one or more active agents may comprise at least an amphoteric or zwitterionic surfactant selected from the group consisting of: cocamidopropyl betaine, lauramidopropyl betaine, cocobetaine, lauryl betaine, lauryl hydroxysultaine, cocamidopropyl hydroxysultaine, coco-hydroxysultaine, coco-sultaine, lauryl sultaine, sodium cocoamphoacetate, disodium cocoamphodiacetate, sodium lauroamphoacetate, disodium lauroamphodiacetate, lauramine oxide, and mixtures thereof.

In one example, non-limiting examples of surfactants, for example for use as hair care active agents, may be selected from the group consisting of: cocoamphoacetate, cocoamphodiacetate, lauroamphoacetate, lauroamphodiacetate, and mixtures thereof.

In one example, non-limiting examples of surfactants, for example for use as hair care active agents, may be selected from the group consisting of: amphoacetates and diamphoacetates. Non-limiting examples of suitable amphoacetates and diamphoacetates include sodium lauroamphoacetate, sodium cocoamphoactetate, disodium lauroamphoacetate, and disodium cocodiamphoacetate, and mixtures thereof.

Perfumes

One or more perfume and/or perfume raw materials such as accords and/or notes may be incorporated into one or more of the fibrous elements and/or particles of the present invention. The perfume may comprise a perfume ingredient selected from the group consisting of: aldehyde perfume ingredients, ketone perfume ingredients, and mixtures thereof.

One or more perfumes and/or perfumery ingredients may be included in the fibrous elements and/or particles of the present invention. A wide variety of natural and synthetic chemical ingredients useful as perfumes and/or perfumery ingredients include but not limited to aldehydes, ketones, esters, and mixtures thereof. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. In one example, a finished perfume typically comprises from about 0.01% to about 2% by weight on a dry fibrous element basis and/or a dry particle basis and/or dry fibrous structure basis.

Antimicrobials, Antibacterials & Antifungals

In one example, pyridinethione particulates are suitable antimicrobial active agents for use in the present invention. In another example, the antimicrobial active agent is a 1-hydroxy-2-pyridinethione salt and is in particulate form. In another example, the concentration of pyridinethione particulate ranges from about 0.01 wt % to about 5 wt %, or from about 0.1 wt % to about 3 wt %, or from about 0.1 wt % to about 2 wt %, by weight of the dry fibrous element and/or dry particle and/or dry fibrous structure of the present invention. In another example, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In another example, the 1-hydroxy-2-pyridinethione salts in platelet particle form have an average particle size of up to about 20 microns, or up to about 5 microns, or up to about 2.5 microns as measured according to the Particle Size Distribution Test Method described herein. Salts formed from other cations, such as sodium, may also be suitable. Pyridinethione actives are described, for example, in U.S. Pat. Nos. 2,809,971; 3,236,733; 3,753,196; 3,761,418; 4,345,080; 4,323,683; 4,379,753; and 4,470,982.

In another example, the antibacterial is chosen from triclosan, triclocarban, chlorhexidine, metronitazole and mixtures thereof.

In another example, in addition to the antimicrobial active selected from polyvalent metal salts of pyrithione, the composition can further include one or more anti-fungal and/or anti-microbial actives. In another example, the anti-microbial active is selected from the group consisting of: coal tar, sulfur, azoles, selenium sulphide, particulate sulphur, keratolytic agents, charcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof.

Bleaching Agents

The fibrous elements and/or particles of the present invention may comprise one or more bleaching agents. Non-limiting examples of suitable bleaching agents include peroxyacids (for example phthalimidoperoxyhexanoic acid (PAP)), perborate, percarbonate, chlorine bleaches, oxygen bleaches, hypohalite bleaches, bleach precursors, bleach activators, bleach catalysts, hydrogen peroxide, bleach boosters, photobleaches, bleaching enzymes, free radical initiators, peroxygen bleaches, and mixtures thereof.

One or more bleaching agents may be included in the fibrous elements and/or particles of the present invention may be included at a level from about 0.05% to about 30% and/or from about 1% to about 20% by weight on a dry fibrous element basis and/or dry particle basis and/or dry fibrous structure basis. If present, bleach activators may be present in the fibrous elements and/or particles of the present invention at a level from about 0.1% to about 60% and/or from about 0.5% to about 40% by weight on a dry fibrous element basis and/or dry particle basis and/or dry fibrous structure basis.

Non-limiting examples of bleaching agents include oxygen bleach, perborate bleach, percarboxylic acid bleach and salts thereof, peroxygen bleach, persulfate bleach, percarbonate bleach, and mixtures thereof. Further, non-limiting examples of bleaching agents are disclosed in U.S. Pat. No. 4,483,781, U.S. patent application Ser. No. 740,446, European Patent Application 0 133 354, U.S. Pat. Nos. 4,412, 934, and 4,634,551.

Non-limiting examples of bleach activators (e.g., acyl lactam activators) are disclosed in U.S. Pat. Nos. 4,915,854; 4,412,934; 4,634,551; and 4,966,723.

In one example, the bleaching agent comprises a transition metal bleach catalyst, which may be encapsulated. The transition metal bleach catalyst typically comprises a transition metal ion, for example a transition metal ion from a transition metal selected from the group consisting of: Mn(II), Mn(III), Mn(IV), Mn(V), Fe(II), Fe(III), Fe(IV), Co(I), Co(II), Co(III), Ni(I), Ni(II), Ni(III), Cu(I), Cu(II), Cu(III), Cr(II), Cr(III), Cr(IV), Cr(V), Cr(VI), V(III), V(IV), V(V), Mo(IV), Mo(V), Mo(VI), W(IV), W(V), W(VI), Pd(II), Ru(II), Ru(III), and Ru(IV). In one example, the transition metal is selected from the group consisting of: Mn(II), Mn(III), Mn(IV), Fe(II), Fe(III), Cr(II), Cr(III), Cr(IV), Cr(V), and Cr(VI). The transition metal bleach catalyst typically comprises a ligand, for example a macropolycyclic ligand, such as a cross-bridged macropolycyclic ligand. The transition metal ion may be coordinated with the ligand. Further, the ligand may comprise at least four donor atoms, at least two of which are bridgehead donor atoms. Non-limiting examples of suitable transition metal bleach catalysts are described in U.S. Pat. Nos. 5,580,485, 4,430,243; 4,728,455; 5,246,621; 5,244,594; 5,284,944; 5,194,416; 5,246,612; 5,256,779; 5,280,117; 5,274,147; 5,153,161; 5,227,084; 5,114,606; 5,114,611, EP 549,271 A1; EP 544,490 A1; EP 549,272 A1; and EP 544,440 A2. In one example, a suitable transition metal bleach catalyst comprises a manganese-based catalyst, for example disclosed in U.S. Pat. No. 5,576,282. In another example, suitable cobalt bleach catalysts are described, in U.S. Pat. Nos. 5,597,936 and 5,595,967. Such cobalt catalysts are readily prepared by known procedures, such as taught for example in U.S. Pat. Nos. 5,597,936, and 5,595,967. In yet another, suitable transition metal bleach catalysts comprise a transition metal complex of ligand such as bispidones described in WO 05/042532 A1.

Non-limiting examples of bleach catalysts include a catalyst system comprising a transition metal cation of defined bleach catalytic activity, such as copper, iron, titanium, ruthenium tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243. Other types of bleach catalysts include the manganese-based complexes disclosed in U.S. Pat. Nos. 5,246,621 and 5,244,594. Preferred examples of theses catalysts include $Mn^{IV}_2(u-O)_3$ (1,4,7-trimethyl-1,4,7-triazacyclononane)$_2$-(PF$_6$)$_2$ ("MnTACN"), $Mn^{III}_2(u-O)_1$ (u-OAc)$_2$ (1,4,7-trimethyl-1,4,7-triazacyclononane)$_2$-(ClO$_4$)$_2$, $Mn^{IV}_4(u-O)_6$(1,4,7-triazacyclononane)$_4$-(ClO$_4$)$_2$, $Mn^{IV}_4(u-O)_1$ (u-OAc)$_2$(1,4,7-trimethyl-1,4,7-triazacyclononane)$_2$-(ClO$_4$)$_3$, and mixtures thereof. See also European patent application publication no. 549,272. Other ligands suitable for use herein include 1,5,9-trimethyl-1,5,9-triazacyclododecane, 2-methyl-1,4,7-triazacyclononane, 2-methyl-1,4,7-triazacyclononane, and mixtures thereof. The bleach catalysts useful in automatic dishwashing compositions and concentrated powder detergent compositions may also be selected as appropriate for the present invention. For examples of suitable bleach catalysts see U.S. Pat. Nos. 4,246,612 and 5,227,084. See also U.S. Pat. No. 5,194,416 which teaches mononuclear manganese (IV) complexes such as Mn(1,4,7-trimethyl-1,4,7-triazacyclononane (OCH$_3$)$_3$-(PF$_6$). Still another type of bleach catalyst, as disclosed in U.S. Pat. No. 5,114,606, is a water-soluble complex of manganese (II), (III), and/or (UV) with a ligand which is a non-carboxylate polyhydroxy compound having at least three consecutive C—OH groups. Preferred ligands include sorbitol, iditol, dulsitol, mannitol, xylitol, arabitol, adonitol, meso-erythritol, meso-inositol, lactose, and mixtures thereof. U.S. Pat. No. 5,114,611 teaches a bleach catalyst comprising a complex of transition metals, including Mn, Co, Fe, or Cu, with an non-(macro)-cyclic ligand. Non-limiting examples of ligands include pyridine, pyridazine, pyrimidine, pyrazine, imidazole, pyrazole, and triazole rings. In one example, the ligand is 2,2'-bispyridylamine In one example, the bleach catalysts includes a Co, Cu, Mn, Fe,-bispyridylmethane and-bispyridylamine complex, such as Co(2,2'-bispyridylamine)Cl$_2$, Di(isothiocyanato) bispyridylamine-cobalt (II), trisdipyridylamine-cobalt(II) perchlorate, Co(2,2-bispyridylamine)$_2$O$_2$ClO$_4$, Bis-(2,2'-bispyridylamine) copper(II) perchlorate, tris(di-2-pyridylamine) iron(II) perchlorate, and mixtures thereof. Other examples of bleach catalysts include Mn gluconate, Mn(CF$_3$SO$_3$)$_2$, Co(NH$_3$)$_5$Cl, and the binuclear Mn complexed with tetra-N-dentate and bi-N-dentate ligands, including N$_4$Mn(III) (u-O)$_2$ Mn(IV)N$_4$)$^+$ and [Bipy$_2$Mn(III) (u-O)$_2$Mn(IV) bipy$_2$]-(ClO$_4$)$_3$.

The bleach catalysts may also be prepared by combining a water-soluble ligand with a water-soluble manganese salt in aqueous media and concentrating the resulting mixture by evaporation. Any convenient water-soluble salt of manganese can be used herein. Manganese (II), (III), (IV) and/or (V) is readily available on a commercial scale. In some instances, sufficient manganese may be present in the wash liquor, but, in general, it is preferred to detergent composition Mn cations in the compositions to ensure its presence in catalytically-effective amounts. Thus, the sodium salt of the ligand and a member selected from the group consisting of: MnSO$_4$, Mn(ClO$_4$)$_2$ or MnCl$_2$ (not as desirable) are dissolved in water at molar ratios of ligand:Mn salt in the range of about 1:4 to 4:1 at neutral or slightly alkaline pH. The water may first be de-oxygenated by boiling and cooled by spraying with nitrogen. The resulting solution is evaporated (under N$_2$, if desired) and the resulting solids are used in the bleaching and detergent compositions herein without further purification.

In an alternate mode, the water-soluble manganese source, such as MnSO$_4$, is added to the bleach/cleaning composition or to the aqueous bleaching/cleaning bath which comprises the ligand. Some type of complex is apparently formed in situ, and improved bleach performance is secured. In such an in situ process, it is convenient to use a considerable molar excess of the ligand over the manganese, and mole ratios of ligand:Mn typically are 3:1 to 15:1. The additional ligand also serves to scavenge vagrant metal ions such as iron and copper, thereby protecting the bleach from decomposition. One possible such system is described in European patent application, publication no. 549,271.

While the structures of the bleach-catalyzing manganese complexes useful in the present invention have not been elucidated, it may be speculated that they comprise chelates or other hydrated coordination complexes which result from the interaction of the carboxyl and nitrogen atoms of the ligand with the manganese cation. Likewise, the oxidation state of the manganese cation during the catalytic process is not known with certainty, and may be the (+II), (+III), (+IV) or (+V) valence state. Due to the ligands' possible six points of attachment to the manganese cation, it may be reasonably speculated that multi-nuclear species and/or "cage" structures may exist in the aqueous bleaching media. Whatever the form of the active Mn ligand species which actually exists, it functions in an apparently catalytic manner to provide improved bleaching performances on stubborn stains such as tea, ketchup, coffee, wine, juice, and the like.

Other bleach catalysts are described, for example, in European patent application, publication no. 408,131 (cobalt complex catalysts), European patent applications, publication nos. 384,503, and 306,089 (metallo-porphyrin catalysts), U.S. Pat. No. 4,728,455 (manganese/multidentate ligand catalyst), U.S. Pat. No. 4,711,748 and European patent application, publication no. 224,952, (absorbed manganese on aluminosilicate catalyst), U.S. Pat. No. 4,601,845 (aluminosilicate support with manganese and zinc or magnesium salt), U.S. Pat. No. 4,626,373 (manganese/ligand catalyst), U.S. Pat. No. 4,119,557 (ferric complex catalyst), German Pat. specification 2,054,019 (cobalt chelant catalyst) Canadian 866,191 (transition metal-containing salts), U.S. Pat. No. 4,430,243 (chelants with manganese cations and non-catalytic metal cations), and U.S. Pat. No. 4,728,455 (manganese gluconate catalysts).

In one example, the bleach catalyst comprises a cobalt pentaamine chloride salts having the formula [Co(NH$_3$)$_5$Cl] Y$_y$, and especially [Co(NH$_3$)$_5$Cl]Cl$_2$. Other cobalt bleach catalysts useful herein are described for example along with their base hydrolysis rates, in M. L. Tobe, "Base Hydrolysis of Transition-Metal Complexes", Adv. Inorg. Bioinorg. Mech., (1983), 2, pages 1-94. For example, Table 1 at page 17, provides the base hydrolysis rates (designated therein as km) for cobalt pentaamine catalysts complexed with oxalate, formate, and acetate. Non-limiting examples of cobalt catalysts useful herein are cobalt pentaamine acetate salts having the formula [Co(NH$_3$)$_5$ OAc]T$_y$, wherein OAc represents an acetate moiety, and especially cobalt pentaamine acetate chloride, [Co(NH$_3$)$_5$OAc]Cl$_2$; as well as [Co(NH$_3$)$_5$OAc](OAc)$_2$; [Co(NH$_3$)$_5$OAc](PF$_6$)$_2$; [Co(NH$_3$)$_5$OAc](SO$_4$); [Co(NH$_3$)$_5$OAc](BF$_4$)$_2$; and [Co(NH$_3$)$_5$OAc](NO$_3$)$_2$.

These bleach catalysts may be readily prepared by known procedures, such as taught for example in the Tobe article hereinbefore and the references cited therein, in U.S. Pat. No. 4,810,410, to Diakun et al, issued Mar. 7, 1989, J. Chem.

Ed. (1989), 66 (12), 1043-45; The Synthesis and Characterization of Inorganic Compounds, W. L. Jolly (Prentice-Hall; 1970), pp. 461-3; Inorg. Chem., 18, 1497-1502 (1979); Inorg. Chem., 21, 2881-2885 (1982); Inorg. Chem., 18, 2023-2025 (1979); Inorg. Synthesis, 173-176 (1960); and Journal of Physical Chemistry 56, 22-25 (1952). These bleach catalysts may also be coprocessed with adjunct materials so as to reduce the color impact if desired for the aesthetics of the product, or to be included in enzyme-containing particles as exemplified hereinafter, or the compositions may be manufactured to contain catalyst "speckles".

Bleaching agents other than oxygen bleaching agents are also known in the art and can be utilized herein (e.g., photoactivated bleaching agents such as the sulfonated zinc and/or aluminum phthalocyanines (U.S. Pat. No. 4,033,718, incorporated herein by reference)), and/or pre-formed organic peracids, such as peroxycarboxylic acid or salt thereof, and/or peroxysulphonic acids or salts thereof. In one example, a suitable organic peracid comprises phthaloylimidoperoxycaproic acid or salt thereof. When present, the photoactivated bleaching agents, such as sulfonated zinc phthalocyanine, may be present in the fibrous elements and/or particles and/or fibrous structures of the present invention at a level from about 0.025% to about 1.25% by weight on a dry fibrous element basis and/or dry particle basis and/or dry fibrous structure basis.

Non-limiting examples of bleach activators are selected from the group consisting of: tetraacetyl ethylene diamine (TAED), benzoylcaprolactam (BzCL), 4-nitrobenzoylcaprolactam, 3-chlorobenzoyl-caprolactam, benzoyloxybenzenesulphonate (BOBS), nonanoyloxybenzene-sulphonate (NOBS), phenyl benzoate (PhBz), decanoyloxybenzenesulphonate (C.sub.10-OBS), benzoylvalerolactam (BZVL), octanoyloxybenzenesulphonate (C.sub.8-OBS), perhydrolyzable esters and mixtures thereof, most preferably benzoylcaprolactam and benzoylvalerolactam. Particularly preferred bleach activators in the pH range from about 8 to about 9.5 are those selected having an OBS or VL leaving group. Quaternary substituted bleach activators (a quaternary substituted bleach activator (QSBA) or a quaternary substituted peracid (QSP)) may also be included.

Non-limiting examples of organic peroxides, such as diacyl peroxides are extensively illustrated in Kirk Othmer, Encyclopedia of Chemical Technology, Vol. 17, John Wiley and Sons, 1982 at pages 27-90 and especially at pages 63-72, all incorporated wherein by reference. If a diacyl peroxide is used, it may be one which exerts minimal adverse impact on spotting/filming.

Dye Transfer Inhibiting Agents

The fibrous elements and/or particles of the present invention may include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. The dye transfer inhibiting agents may be present in the fibrous elements and/or particles and/or fibrous structure products of the present invention at levels from about 0.0001% to about 10%, from about 0.01% to about 5% or even from about 0.1% to about 3% by weight on a dry fibrous element basis and/or dry particle basis and/or dry fibrous structure basis.

Brighteners

The fibrous elements and/or particles of the present invention may contain active agents, such as brighteners, for example fluorescent brighteners. Such brighteners may tint articles being cleaned.

The fibrous elements and/or particles may comprise C.I. fluorescent brightener 260 in α-crystalline form having the following structure:

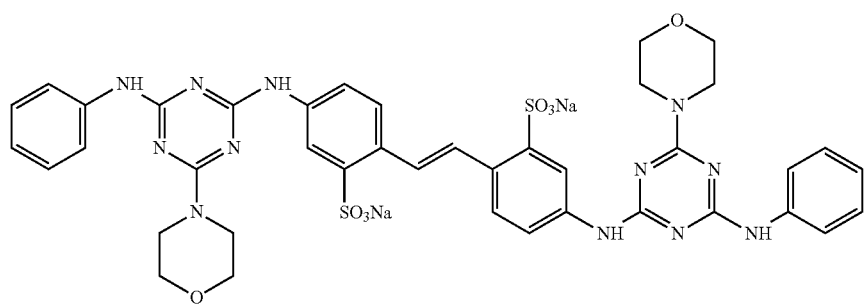

In one aspect, the brightener is a cold water-soluble brightener, such as the C.I. fluorescent brightener 260 in α-crystalline form.

In one aspect the brightener is predominantly in α-crystalline form, which means that typically at least 50 wt %, at least 75 wt %, at least 90 wt %, at least 99 wt %, or even substantially all, of the C.I. fluorescent brightener 260 is in α-crystalline form.

The brightener is typically in a micronized particulate form, having a weight average primary particle size of from 3 to 30 μm, from 3 to 20 μm, or from 3 to 10 μm as measured according to the Particle Size Distribution Test Method The composition may comprise C.I. fluorescent brightener 260 in β-crystalline form, and the weight ratio of: (i) C.I. fluorescent brightener 260 in α-crystalline form, to (ii) C.I. fluorescent brightener 260 in β-crystalline form may be at least 0.1, or at least 0.6.

BE680847 relates to a process for making C.I fluorescent brightener 260 in α-crystalline form.

Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982). Specific nonlimiting examples of optical brighteners which are useful in the present compositions are those identified in U.S. Pat. Nos. 4,790,856 and 3,646,015.

A further suitable brightener has the structure below:

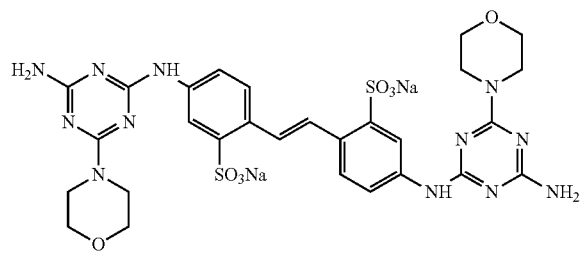

Suitable fluorescent brightener levels include lower levels of from about 0.01, from about 0.05, from about 0.1 or even from about 0.2 wt % to upper levels of 0.5 or even 0.75 wt %.

In one aspect the brightener may be loaded onto a clay to form a particle.

Hueing Agents

The composition may comprise a hueing agent. Suitable hueing agents include dyes, dye-clay conjugates, and pigments. Suitable dyes include small molecule dyes and polymeric dyes. Suitable small molecule dyes include small molecule dyes selected from the group consisting of: dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof.

In another aspect, suitable small molecule dyes include small molecule dyes selected from the group consisting of: Colour Index (Society of Dyers and Colourists, Bradford, UK) numbers Direct Violet 9, Direct Violet 35, Direct Violet 48, Direct Violet 51, Direct Violet 66, Direct Violet 99, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Red 52, Acid Violet 49, Acid Violet 50, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159 and mixtures thereof. In another aspect, suitable small molecule dyes include small molecule dyes selected from the group consisting of: Colour Index (Society of Dyers and Colourists, Bradford, UK) numbers Acid Violet 17, Acid Violet 43, Acid Red 52, Acid Red 73, Acid Red 88, Acid Red 150, Acid Blue 25, Acid Blue 29, Acid Blue 45, Acid Blue 113, Acid Black 1, Direct Blue 1, Direct Blue 71, Direct Violet 51 and mixtures thereof. In another aspect, suitable small molecule dyes include small molecule dyes selected from the group consisting of: Colour Index (Society of Dyers and Colourists, Bradford, UK) numbers Acid Violet 17, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of: polymers containing conjugated chromogens (dye-polymer conjugates) and polymers with chromogens co-polymerized into the backbone of the polymer and mixtures thereof.

In another aspect, suitable polymeric dyes include polymeric dyes selected from the group consisting of: surface-substantive colorants sold under the name of Liquitint® (Milliken, Spartanburg, South Carolina, USA), dye-polymer conjugates formed from at least one reactive dye and a polymer selected from the group consisting of: polymers comprising a moiety selected from the group consisting of: a hydroxyl moiety, a primary amine moiety, a secondary amine moiety, a thiol moiety and mixtures thereof. In still another aspect, suitable polymeric dyes include polymeric dyes selected from the group consisting of: Liquitint® (Milliken, Spartanburg, South Carolina, USA) Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colourants, alkoxylated thiophene polymeric colourants, and mixtures thereof.

Preferred hueing dyes include the whitening agents found in WO 08/87497 A1. These whitening agents may be characterized by the following structure (I):

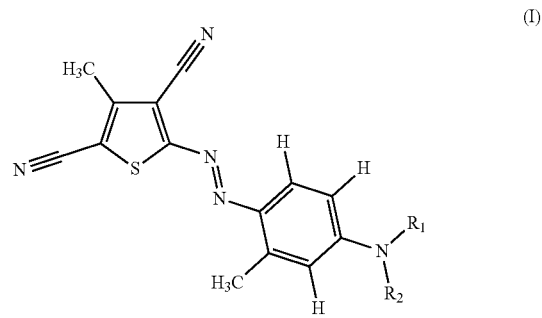

wherein $R_1$ and $R_2$ can independently be selected from:

a) $[(CH_2CR'HO)_x(CH_2CR''HO)_yH]$ wherein R' is selected from the group consisting of: H, $CH_3$, $CH_2O(CH_2CH_2O)_zH$, and mixtures thereof; wherein R'' is selected from the group consisting of: H, $CH_2O(CH_2CH_2O)_zH$, and mixtures thereof; wherein $x+y \leq 5$; wherein $y \geq 1$; and wherein $z=0$ to 5;

b) $R_1$=alkyl, aryl or aryl alkyl and $R_2=[(CH_2CR'HO)_x(CH_2CR''HO)_yH]$ wherein R' is selected from the group consisting of: H, $CH_3$, $CH_2O(CH_2CH_2O)_zH$, and mixtures thereof; wherein R'' is selected from the group consisting of: H, $CH_2O(CH_2CH_2O)_zH$, and mixtures thereof; wherein $x+y \leq 10$; wherein $y \geq 1$; and wherein $z=0$ to 5;

c) $R_1=[CH_2CH_2(OR_3)CH_2OR_4]$ and $R_2=[CH_2CH_2(OR_3)CH_2O R_4]$ wherein $R_3$ is selected from the group consisting of: H, $(CH_2CH_2O)_zH$, and mixtures thereof; and wherein $z=0$ to 10;

wherein $R_4$ is selected from the group consisting of: $(C_1-C_{16})$alkyl, aryl groups, and mixtures thereof; and d) wherein $R_1$ and $R_2$ can independently be selected from the amino addition product of styrene oxide, glycidyl methyl ether, isobutyl glycidyl ether, isopropylglycidyl ether, t-butyl glycidyl ether, 2-ethylhexylgycidyl ether, and glycidylhexadecyl ether, followed by the addition of from 1 to 10 alkylene oxide units.

A preferred whitening agent of the present invention may be characterized by the following structure (II):

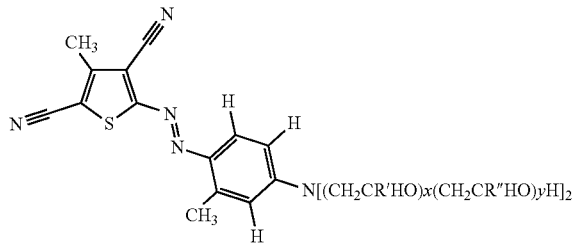

(II)

wherein R' is selected from the group consisting of: H, $CH_3$, $CH_2O(CH_2CH_2O)_zH$, and mixtures thereof; wherein R" is selected from the group consisting of: H, $CH_2O(CH_2CH_2O)_zH$, and mixtures thereof; wherein x+y≤5; wherein y≥1; and wherein z=0 to 5.

A further preferred whitening agent of the present invention may be characterized by the following structure (III):

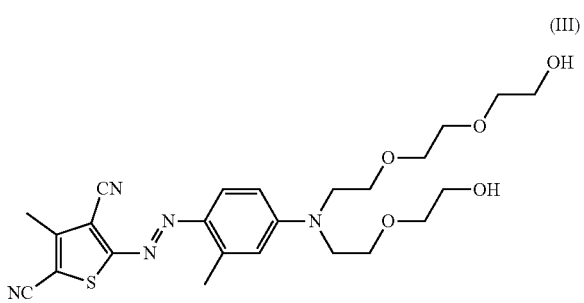 [SMILES: Cc1cc(N(CCOCCO)CCOCCOCCO)ccc1/N=N/c1sc(C#N)c(C)c1C#N]

(III)

This whitening agent is commonly referred to as "Violet DD". Violet DD is typically a mixture having a total of 5 EO groups. This structure is arrived the following selection in Structure I of the following pendant groups in "part a" above:

|   | R1 | | | | R2 | | | |
|---|----|---|---|---|----|---|---|---|
|   | R' | R" | X | Y | R' | R" | x | y |
| a | H | H | 3 | 1 | H | H | 0 | 1 |
| b | H | H | 2 | 1 | H | H | 1 | 1 |
| c = b | H | H | 1 | 1 | H | H | 2 | 1 |
| d = a | H | H | 0 | 1 | H | H | 3 | 1 |

Further whitening agents of use include those described in USPN 2008 34511 A1 (Unilever). A preferred agent is "Violet 13".

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of: one cationic/basic dye selected from the group consisting of: C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of: Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of: flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.

In another aspect, suitable pigments include pigments selected from the group consisting of: Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used). Suitable fabric hueing agents can be purchased from Aldrich, Milwaukee, Wisconsin, USA; Ciba Specialty Chemicals, Basel, Switzerland; BASF, Ludwigshafen, Germany; Dayglo Color Corporation, Mumbai, India; Organic Dyestuffs Corp., East Providence, Rhode Island, USA; Dystar, Frankfurt, Germany; Lanxess, Leverkusen, Germany; Megazyme, Wicklow, Ireland; Clariant, Muttenz, Switzerland; Avecia, Manchester, UK and/or made in accordance with the examples contained herein. Suitable hueing agents are described in more detail in U.S. Pat. No. 7,208,459 B2.

Enzymes

One or more enzymes may be present in the fibrous elements and/or particles of the present invention. Non-limiting examples of suitable enzymes include proteases, amylases, lipases, cellulases, carbohydrases including mannanases and endoglucanases, pectinases, hemicellulases, peroxidases, xylanases, phopholipases, esterases, cutinases, keratanases, reductases, oxidases, phenoloxidases, lipoxygenases, ligninases, pullulanases, tannases, penosanases, malanases, glucanases, arabinosidases, hyaluraonidases, chrondroitinases, laccases, and mixtures thereof.

Enzymes may be included in the fibrous elements and/or particles of the present invention for a variety of purposes, including but not limited to removal of protein-based, carbohydrate-based, or triglyceride-based stains from substrates, for the prevention of refugee dye transfer in fabric laundering, and for fabric restoration. In one example, the fibrous elements and/or particles of the present invention may include proteases, amylases, lipases, cellulases, peroxidases, and mixtures thereof of any suitable origin, such as vegetable, animal, bacterial, fungal and yeast origin. Selections of the enzymes utilized are influenced by factors such as pH-activity and/or stability optima, thermostability, and stability to other additives, such as active agents, for example builders, present within the fibrous elements and/or particles. In one example, the enzyme is selected from the group consisting of: bacterial enzymes (for example bacterial amylases and/or bacterial proteases), fungal enzymes (for example fungal cellulases), and mixtures thereof.

When present in the fibrous elements and/or particles of the present invention, the enzymes may be present at levels sufficient to provide a "cleaning-effective amount". The term "cleaning effective amount" refers to any amount capable of producing a cleaning, stain removal, soil removal, whitening, deodorizing, or freshness improving effect on substrates such as fabrics, dishware, flooring, porcelain and ceramics, metal surfaces and the like. In practical terms for current commercial preparations, typical amounts are up to about 5 mg by weight, more typically 0.01 mg to 3 mg, of active enzyme per gram of the fibrous element and/or particle of the present invention. Stated otherwise, the fibrous elements and/or particles of the present invention will typically comprise from about 0.001% to about 5% and/or from about 0.01% to about 3% and/or from about 0.01% to about 1% by weight on a dry fibrous element basis and/or dry particle basis and/or dry fibrous structure basis.

One or more enzymes may be applied to the fibrous element and/or particle after the fibrous element and/or particle is produced.

A range of enzyme materials and means for their incorporation into the filament-forming composition of the present invention, which may be a synthetic detergent composition, is also disclosed in WO 9307263 A; WO 9307260 A; WO 8908694 A; U.S. Pat. Nos. 3,553,139; 4,101,457; and 4,507,219.

Enzyme Stabilizing System

When enzymes are present in the fibrous elements and/or particles of the present invention, an enzyme stabilizing system may also be included in the fibrous elements and/or particles. Enzymes may be stabilized by various techniques. Non-limiting examples of enzyme stabilization techniques are disclosed and exemplified in U.S. Pat. Nos. 3,600,319 and 3,519,570; EP 199,405, EP 200,586; and WO 9401532 A.

In one example, the enzyme stabilizing system may comprise calcium and/or magnesium ions.

The enzyme stabilizing system may be present in the fibrous elements and/or particles of the present invention at a level of from about 0.001% to about 10% and/or from about 0.005% to about 8% and/or from about 0.01% to about 6% by weight on a dry fibrous element basis and/or dry particle basis and/or dry fibrous structure basis. The enzyme stabilizing system can be any stabilizing system which is compatible with the enzymes present in the fibrous elements and/or particles. Such an enzyme stabilizing system may be inherently provided by other formulation actives, or be added separately, e.g., by the formulator or by a manufacturer of enzymes. Such enzyme stabilizing systems may, for example, comprise calcium ion, magnesium ion, boric acid, propylene glycol, short chain carboxylic acids, boronic acids, and mixtures thereof, and are designed to address different stabilization problems.

Heat Forming Agents

The fibrous elements and/or particles of the present invention may contain a heat forming agent. Heat forming agents are formulated to generate heat in the presence of water and/or oxygen (e.g., oxygen in the air, etc.) and to thereby accelerate the rate at which the fibrous structure degrades in the presence of water and/or oxygen, and/or to increase the effectiveness of one or more of the actives in the fibrous element. The heat forming agent can also or alternatively be used to accelerate the rate of release of one or more actives from the fibrous structure. The heat forming agent is formulated to undergo an exothermic reaction when exposed to oxygen (i.e., oxygen in the air, oxygen in the water, etc.) and/or water. Many different materials and combination of materials can be used as the heat forming agent. Non-limiting heat forming agents that can be used in the fibrous structure include electrolyte salts (e.g., aluminum chloride, calcium chloride, calcium sulfate, cupric chloride, cuprous chloride, ferric sulfate, magnesium chloride, magnesium sulfate, manganese chloride, manganese sulfate, potassium chloride, potassium sulfate, sodium acetate, sodium chloride, sodium carbonate, sodium sulfate, etc.), glycols (e.g., propylene glycol, dipropylenenglycol, etc.), lime (e.g., quick lime, slaked lime, etc.), metals (e.g., chromium, copper, iron, magnesium, manganese, etc.), metal oxides (e.g., aluminum oxide, iron oxide, etc.), polyalkyleneamine, polyalkyleneimine, polyvinyl amine, zeolites, glycerin, 1,3, propanediol, polysorbates esters (e.g., Tweens 20, 60, 85, 80), and/or poly glycerol esters (e.g., Noobe, Drewpol and Drewmulze from Stepan). The heat forming agent can be formed of one or more materials. For example, magnesium sulfate can singularly form the heat forming agent. In another non-limiting example, the combination of about 2-25 weight percent activated carbon, about 30-70 weight percent iron powder and about 1-10 weight percent metal salt can form the heat forming agent. As can be appreciated, other or additional materials can be used alone or in combination with other materials to form the heat forming agent. Non-limiting examples of materials that can be used to form the heat forming agent used in a fibrous structure are disclosed in U.S. Pat. Nos. 5,674,270 and 6,020,040; and in U.S. Patent Application Publication Nos. 2008/0132438 and 2011/0301070.

Degrading Accelerators

The fibrous elements and/or particles of the present invention may contain a degrading accelerators used to accelerate the rate at which a fibrous structure degrades in the presence of water and/or oxygen. The degrading accelerator, when used, is generally designed to release gas when exposed to water and/or oxygen, which in turn agitates the region about the fibrous structure so as to cause acceleration in the degradation of a carrier film of the fibrous structure. The degrading accelerator, when used, can also or alternatively be used to accelerate the rate of release of one or more actives from the fibrous structure; however, this is not required. The degrading accelerator, when used, can also or alternatively be used to increase the effectivity of one or more of the actives in the fibrous structure; however, this is not required. The degrading accelerator can include one or more materials such as, but not limited to, alkali metal carbonates (e.g. sodium carbonate, potassium carbonate, etc.), alkali metal hydrogen carbonates (e.g., sodium hydrogen carbonate, potassium hydrogen carbonate, etc), ammonium carbonate, etc. The water soluble strip can optionally include one or more activators that are used to activate or increase the rate of activation of the one or more degrading accelerators in the fibrous structure. As can be appreciated, one or more activators can be included in the fibrous structure even when no degrading accelerator exists in the fibrous structure; however, this is not required. For instance, the activator can include an acidic or basic compound, wherein such acidic or basic compound can be used as a supplement to one or more actives in the fibrous structure when a degrading accelerator is or is not included in the fibrous structure. Non-limiting examples of activators, when used, that can be included in the fibrous structure include organic acids (e.g., hydroxy-carboxylic acids [citric acid, tartaric acid, malic acid, lactic acid, gluconic acid, etc.], saturated aliphatic carboxylic acids [acetic acid, succinic acid, etc.], unsaturated aliphatic carboxylic acids [e.g., fumaric acid, etc.]. Non-limiting examples of materials that can be used to form degrading accelerators and activators used in a fibrous structure are disclosed in U.S. Patent Application Publication No. 2011/0301070.

Release of Active Agent

One or more active agents may be released from the fibrous element and/or particle and/or fibrous structure when the fibrous element and/or particle and/or fibrous structure is exposed to a triggering condition. In one example, one or more active agents may be released from the fibrous element and/or particle and/or fibrous structure or a part thereof when the fibrous element and/or particle and/or fibrous structure or the part thereof loses its identity, in other words, loses its physical structure. For example, a fibrous element and/or particle and/or fibrous structure loses its physical structure when the filament-forming material dissolves, melts or undergoes some other transformative step such that its structure is lost. In one example, the one or more active agents are released from the fibrous element and/or particle and/or fibrous structure when the fibrous element's and/or particle's and/or fibrous structure's morphology changes.

In another example, one or more active agents may be released from the fibrous element and/or particle and/or fibrous structure or a part thereof when the fibrous element and/or particle and/or fibrous structure or the part thereof alters its identity, in other words, alters its physical structure rather than loses its physical structure. For example, a fibrous element and/or particle and/or fibrous structure alters its physical structure when the filament-forming material swells, shrinks, lengthens, and/or shortens, but retains its filament-forming properties.

In another example, one or more active agents may be released from the fibrous element and/or particle and/or fibrous structure with its morphology not changing (not losing or altering its physical structure).

In one example, the fibrous element and/or particle and/or fibrous structure may release an active agent upon the fibrous element and/or particle and/or fibrous structure being exposed to a triggering condition that results in the release of the active agent, such as by causing the fibrous element and/or particle and/or fibrous structure to lose or alter its identity as discussed above. Non-limiting examples of triggering conditions include exposing the fibrous element and/or particle and/or fibrous structure to solvent, a polar solvent, such as alcohol and/or water, and/or a non-polar solvent, which may be sequential, depending upon whether the filament-forming material comprises a polar solvent-soluble material and/or a non-polar solvent-soluble material; exposing the fibrous element and/or particle and/or fibrous structure to heat, such as to a temperature of greater than 75° F. and/or greater than 100° F. and/or greater than 150° F. and/or greater than 200° F. and/or greater than 212° F.; exposing the fibrous element and/or particle and/or fibrous structure to cold, such as to a temperature of less than 40° F. and/or less than 32° F. and/or less than 0° F.; exposing the fibrous element and/or particle and/or fibrous structure to a force, such as a stretching force applied by a consumer using the fibrous element and/or particle and/or fibrous structure; and/or exposing the fibrous element and/or particle and/or fibrous structure to a chemical reaction; exposing the fibrous element and/or particle and/or fibrous structure to a condition that results in a phase change; exposing the fibrous element and/or particle and/or fibrous structure to a pH change and/or a pressure change and/or temperature change; exposing the fibrous element and/or particle and/or fibrous structure to one or more chemicals that result in the fibrous element and/or particle and/or fibrous structure releasing one or more of its active agents; exposing the fibrous element and/or particle and/or fibrous structure to ultrasonics; exposing the fibrous element and/or particle and/or fibrous structure to light and/or certain wavelengths; exposing the fibrous element and/or particle and/or fibrous structure to a different ionic strength; and/or exposing the fibrous element and/or particle and/or fibrous structure to an active agent released from another fibrous element and/or particle and/or fibrous structure.

In one example, one or more active agents may be released from the fibrous elements and/or particles of the present invention when a fibrous structure product comprising the fibrous elements and/or particles is subjected to a triggering step selected from the group consisting of: pre-treating stains on a fabric article with the fibrous structure product; forming a wash liquor by contacting the fibrous structure product with water; tumbling the fibrous structure product in a dryer; heating the fibrous structure product in a dryer; and combinations thereof.

Fibrous Element-Forming Composition

The fibrous elements of the present invention are made from a fibrous element-forming composition, for example a filament-forming composition. The fibrous element-forming composition is a polar-solvent-based composition. In one example, the fibrous element-forming composition is an aqueous composition comprising one or more fibrous element-forming materials and one or more active agents.

The fibrous element-forming composition of the present invention may have a shear viscosity as measured according to the Shear Viscosity Test Method described herein of from about 1 Pa·s to about 25 Pa·s and/or from about 2 Pa·s to about 20 Pa·s and/or from about 3 Pa·s to about 10 Pa·s, as measured at a shear rate of 3,000 sec$^{-1}$ and at the processing temperature (50° C. to 100° C.).

The fibrous element-forming composition of the present invention may exhibit a viscosity (rotational rheometer viscosity) of from about 0.01 Pas to about 1.2 Pas and/or from about 0.02 Pas to about 1.0 Pas as measured according to the Rotational Rheometer Test Method described herein.

The fibrous element-forming composition may be processed at a temperature of from about 50° C. to about 100° C. and/or from about 65° C. to about 95° C. and/or from about 70° C. to about 90° C. when making fibrous elements from the fibrous element-forming composition.

In one example, the fibrous element-forming composition may comprise at least 20% and/or at least 30% and/or at least 40% and/or at least 45% and/or at least 50% to about 90% or about 85% or to about 80% or to about 75% by weight of one or more fibrous element-forming materials, one or more active agents, and mixtures thereof. The fibrous element-forming composition may comprise from about 10% to about 80% by weight of a polar solvent, such as water.

In one example, non-volatile components of the fibrous element-forming composition may comprise from about 20% and/or 30% and/or 40% and/or 45% and/or 50% to about 75% and/or 80% and/or 85% and/or 90% by weight based on the total weight of the fibrous element-forming composition. The non-volatile components may be composed of fibrous element-forming materials, such as backbone polymers, active agents and combinations thereof. Volatile components of the fibrous element-forming composition will comprise the remaining percentage and range from 10% to 80% by weight based on the total weight of the fibrous element-forming composition.

In a fibrous element spinning process, the fibrous elements need to have initial stability as they leave the spinning die. Capillary Number is used to characterize this initial stability criterion. At the conditions of the die, the Capillary Number should be at least 1 and/or at least 3 and/or at least 4 and/or at least 5.

In one example, the fibrous element-forming composition exhibits a Capillary Number of from at least 1 to about 50 and/or at least 3 to about 50 and/or at least 5 to about 30 such that the fibrous element-forming composition can be effectively polymer processed into a fibrous element.

"Polymer processing" as used herein means any spinning operation and/or spinning process by which a fibrous element comprising a processed fibrous element-forming material is formed from a fibrous element-forming composition. The spinning operation and/or process may include spun bonding, melt blowing, electro-spinning, rotary spinning, continuous filament producing and/or tow fiber producing operations/processes. A "processed fibrous element-forming material" as used herein means any fibrous element-forming material that has undergone a melt processing operation and a subsequent polymer processing operation resulting in a fibrous element.

The Capillary number is a dimensionless number used to characterize the likelihood of this droplet breakup. A larger capillary number indicates greater fluid stability upon exiting the die. The Capillary number is defined as follows:

$$Ca = \frac{V * \eta}{\sigma}$$

V is the fluid velocity at the die exit (units of Length per Time), $\eta$ is the fluid viscosity at the conditions of the die (units of Mass per Length*Time), $\sigma$ is the surface tension of the fluid (units of mass per Time$^2$). When velocity, viscosity, and surface tension are expressed in a set of consistent units, the resulting Capillary number will have no units of its own; the individual units will cancel out.

The Capillary number is defined for the conditions at the exit of the die. The fluid velocity is the average velocity of the fluid passing through the die opening. The average velocity is defined as follows:

$$V = \frac{Vol'}{Area}$$

Vol'=volumetric flowrate (units of Length$^3$ per Time),
Area=cross-sectional area of the die exit (units of Length$^2$).

When the die opening is a circular hole, then the fluid velocity can be defined as $$V = \frac{Vol'}{\pi * R^2}$$

R is the radius of the circular hole (units of length).

The fluid viscosity will depend on the temperature and may depend of the shear rate. The definition of a shear thinning fluid includes a dependence on the shear rate. The surface tension will depend on the makeup of the fluid and the temperature of the fluid.

In one example, the fibrous element-forming composition may comprise one or more release agents and/or lubricants. Non-limiting examples of suitable release agents and/or lubricants include fatty acids, fatty acid salts, fatty alcohols, fatty esters, sulfonated fatty acid esters, fatty amine acetates and fatty amides, silicones, aminosilicones, fluoropolymers and mixtures thereof.

In one example, the fibrous element-forming composition may comprise one or more antiblocking and/or detackifying agents. Non-limiting examples of suitable antiblocking and/or detackifying agents include starches, modified starches, crosslinked polyvinylpyrrolidone, crosslinked cellulose, microcrystalline cellulose, silica, metallic oxides, calcium carbonate, talc and mica.

Active agents of the present invention may be added to the fibrous element-forming composition prior to and/or during fibrous element formation and/or may be added to the fibrous element after fibrous element formation. For example, a perfume active agent may be applied to the fibrous element and/or fibrous structure comprising the fibrous element after the fibrous element and/or fibrous structure according to the present invention are formed. In another example, an enzyme active agent may be applied to the fibrous element and/or fibrous structure comprising the fibrous element after the fibrous element and/or fibrous structure according to the present invention are formed. In still another example, one or more particles, which may not be suitable for passing through the spinning process for making the fibrous element, may be applied to the fibrous element and/or fibrous structure comprising the fibrous element after the fibrous element and/or fibrous structure according to the present invention are formed.

Extensional Aids

In one example, the fibrous element comprises an extensional aid. Non-limiting examples of extensional aids can include polymers, other extensional aids, and combinations thereof.

In one example, the extensional aids have a weight-average molecular weight of at least about 500,000 Da. In another example, the weight average molecular weight of the extensional aid is from about 500,000 to about 25,000,000, in another example from about 800,000 to about 22,000,000, in yet another example from about 1,000,000 to about 20,000,000, and in another example from about 2,000,000 to about 15,000,000. The high molecular weight extensional aids are preferred in some examples of the invention due to the ability to increase extensional melt viscosity and reducing melt fracture.

The extensional aid, when used in a meltblowing process, is added to the composition of the present invention in an amount effective to visibly reduce the melt fracture and capillary breakage of fibers during the spinning process such that substantially continuous fibers having relatively consistent diameter can be melt spun. Regardless of the process employed to produce fibrous elements and/or particles, the extensional aids, when used, can be present from about 0.001% to about 10%, by weight on a dry fibrous element basis and/or dry particle basis and/or dry fibrous structure basis, in one example, and in another example from about 0.005 to about 5%, by weight on a dry fibrous element basis and/or dry particle basis and/or dry fibrous structure basis, in yet another example from about 0.01 to about 1%, by weight on a dry fibrous element basis and/or dry particle basis and/or dry fibrous structure basis, and in another example from about 0.05% to about 0.5%, by weight on a dry fibrous element basis and/or dry particle basis and/or dry fibrous structure basis.

Non-limiting examples of polymers that can be used as extensional aids can include alginates, carrageenans, pectin, chitin, guar gum, xanthum gum, agar, gum arabic, karaya gum, tragacanth gum, locust bean gum, alkylcellulose, hydroxyalkylcellulose, carboxyalkylcellulose, and mixtures thereof.

Nonlimiting examples of other extensional aids can include modified and unmodified polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide, and mixtures thereof.

Method for Making Fibrous Elements

The fibrous elements of the present invention may be made by any suitable process. A non-limiting example of a suitable process for making the fibrous elements of the present invention is described below.

Figure 5:
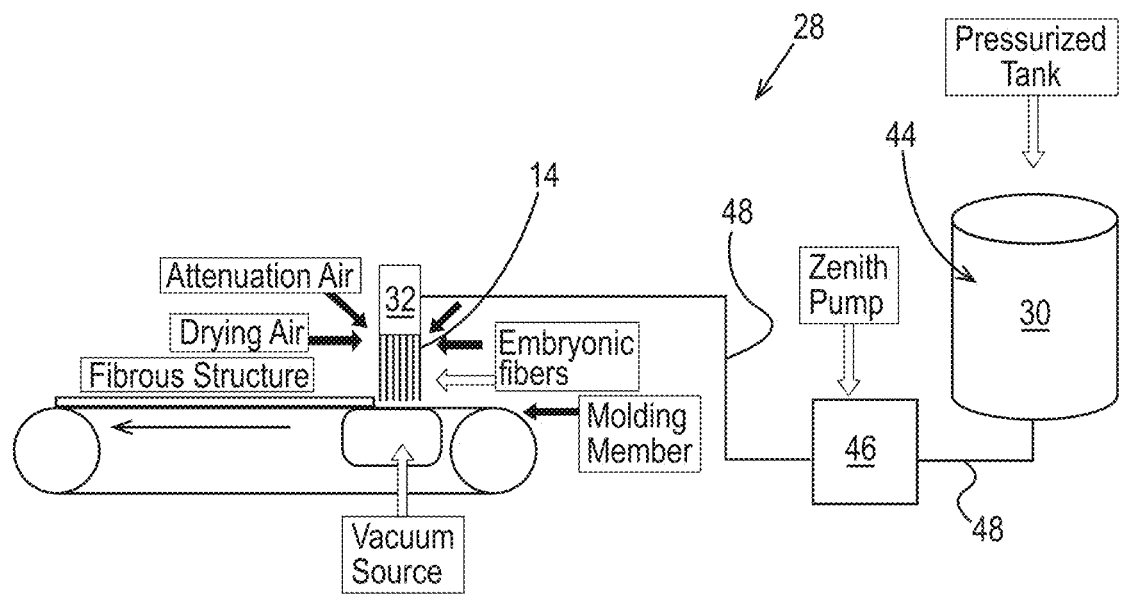
FIG. 5 is a schematic representation of an example of a process for making fibrous elements of the present invention.
Figure 6:
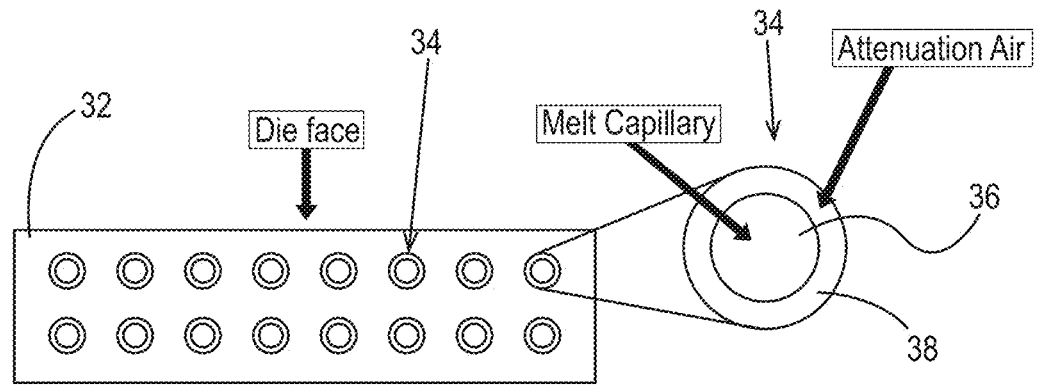
FIG. 6 is a schematic representation of an example of a die with a magnified view used in the process of FIG. 5.

In one example, as shown in FIGS. 5 and 6. a method 28 for making a fibrous element 14, for example a natural polymer-based fibrous element according to the present invention comprises the steps of:
 a. providing a fibrous element-forming composition 30 comprising one or more fibrous element-forming materials, for example one or more natural polymer-based fibrous element-forming materials, for example one or more natural polymer-based fibrous element-forming materials comprising a modified polysaccharide, for example a modified starch, such as an acetylated starch, and optionally one or more active agents; and
 b. spinning the fibrous element-forming composition 30, such as via a spinning die 32, such as a multi-row capillary die, such as a multi-row meltblow capillary die, into one or more fibrous elements 14, for example a natural polymer-based fibrous element according to the present invention, such as filaments, comprising the one or more fibrous element-forming materials and optionally, the one or more active agents. The one or more active agents may be releasable from the fibrous element when exposed to conditions of intended use. The total level of the one or more fibrous element-forming materials present in the fibrous element 14 and/or a plurality of fibrous elements 14, for example a plurality of fibrous elements in a fibrous structure, when active agents are present therein, may be less than 80% and/or less than 70% and/or less than 65% and/or less than 60% and/or about 50% or less by weight on a dry fibrous element basis and/or dry fibrous structure basis and the total level of the one or more active agents, when present in the fibrous element 14 and/or a plurality of fibrous elements 14, for example a plurality of fibrous elements in a fibrous structure, may be greater than 20% and/or greater than 30% and/or greater than 35% and/or greater than 40% and/or about 50% or greater and/or 65% or greater and/or 80% or greater by weight on a dry fibrous element basis and/or dry fibrous structure basis.

As shown in FIG. 6, the spinning die 32 may comprise a plurality of fibrous element-forming holes 34 that include a melt capillary 36 encircled by a concentric attenuation fluid hole 38 through which a fluid, such as air, passes to facilitate attenuation of the filament-forming composition 30 into a fibrous element 14 as it exits the fibrous element-forming hole 34.

In one example, during the spinning step, any volatile solvent, such as water, present in the filament-forming composition 30 is removed, such as by drying, as the fibrous element 14 is formed. In one example, greater than 30% and/or greater than 40% and/or greater than 50% of the weight of the fibrous element-forming composition's volatile solvent, such as water, is removed during the spinning step, such as by drying the fibrous element being produced.

The fibrous element-forming composition may comprise any suitable total level of fibrous element-forming materials and any suitable level of active agents so long as the fibrous element produced from the fibrous element-forming composition comprises a total level of fibrous element-forming materials in the fibrous element and/or a plurality of fibrous elements, for example a plurality of fibrous elements in a fibrous structure, of from about 5% to 50% or less by weight on a dry fibrous element basis and/or dry particle basis and/or dry fibrous structure basis and a total level of active agents in the fibrous element and/or a plurality of fibrous elements, for example a plurality of fibrous elements in a fibrous structure, of from 50% to about 95% by weight on a dry fibrous element basis and/or dry particle basis and/or dry fibrous structure basis.

In one example, the fibrous element-forming composition may comprise any suitable total level of fibrous element-forming materials and any suitable level of active agents so long as the fibrous element produced from the fibrous element-forming composition comprises a total level of fibrous element-forming materials in the fibrous element and/or particle of from about 5% to 50% or less by weight on a dry fibrous element basis and/or dry particle basis and/or dry fibrous structure basis and a total level of active agents in the fibrous element and/or particle of from 50% to about 95% by weight on a dry fibrous element basis and/or dry particle basis and/or dry fibrous structure basis, wherein the weight ratio of fibrous element-forming material to total level of active agents is 1 or less.

In one example, the fibrous element-forming composition comprises from about 1% and/or from about 5% and/or from about 10% to about 50% or to about 40% or to about 30% or to about 20% by weight of the fibrous element-forming composition of fibrous element-forming materials; from about 1% and/or from about 5% and/or from about 10% to about 50% or to about 40% or to about 30% or to about 20% by weight of the fibrous element-forming composition of active agents; and from about 20% and/or from about 25% and/or from about 30% and/or from about 40% to about 80% or to about 70% or to about 60% or to about 50% by weight of the fibrous element-forming composition of a volatile solvent, such as water. The fibrous element-forming composition may comprise minor amounts of other active agents, such as less than 10% and/or less than 5% and/or less than 3% and/or less than 1% by weight of the fibrous element-forming composition of plasticizers, pH adjusting agents, and other active agents.

The fibrous element-forming composition is spun into one or more fibrous elements and/or particles by any suitable spinning process, such as meltblowing, spunbonding, electro-spinning, and/or rotary spinning In one example, the fibrous element-forming composition is spun into a plurality of fibrous elements and/or particles by meltblowing. For example, the fibrous element-forming composition may be pumped from a tank to a meltblown spinnerette. Upon exiting one or more of the fibrous element-forming holes in the spinnerette, the fibrous element-forming composition is attenuated with air to create one or more fibrous elements and/or particles. The fibrous elements and/or particles may then be dried to remove any remaining solvent used for spinning, such as the water.

The fibrous elements and/or particles of the present invention may be collected on a belt, such as a patterned belt to form a fibrous structure comprising the fibrous elements and/or particles.

Non-Limiting Examples of Fibrous Element-Forming Compositions for Making Fibrous Elements Two non-limiting examples of fibrous element-forming compositions of the present invention (Samples A and B) that are suitable for making fibrous elements and/or ultimately fibrous structures of the present invention are shown in Table 5 below.

TABLE 5

|  | Sample A | Sample B |
| --- | --- | --- |
| Percent deionized water | 85% | 55% |
| Surfactant:acetylated starch wt ratio | 2:1 | 1:2 |
| % NaLAS in solution | 10% | 15% |
| % Acetylated starch in solution | 5% | 30% |
| Acetylated Starch | A | B |
| Acetylated Starch Mw | 60K | 215K |
| Acetylated Starch DS | 0.31 | 0.51 |
| Rotational Rheometer Viscosity[1] | 0.02 Pa · s | 0.99 Pa · s |

[1]Rotational Rheometer Viscosity measured according to the Rotational Rheometer Viscosity Test Method described herein Particles The particles may be water-soluble or water-insoluble. In one example, one group of particles may be water-soluble and a different group of particles may be water-insoluble. In another example, the particles may comprise one or more active agents (in other words, the particles may comprise active agent-containing particles). In still another example, the particles may consist essentially of and/or consist of one or more active agents (in other words, the particles may comprise 100% or about 100% by weight on a dry particle basis of one or more active agents). In still another example, the particles may comprise water-soluble particles. In yet another example, the particles may comprise water-soluble, active agent-containing particles.

In one example, the particles comprise agglomerates of different materials, for example different sub-particles, such as one or more effervescent salt particles, for example sodium bicarbonate, one or more effervescent acid particles, for example citric acid, one or more builder particles, such as zeolite, wherein the particles may be coated with a gas bubble-stabilizing agent, such as a surfactant, for example a sulfate-free surfactant like DSCG and optionally one or more polymers, for example polyvinylpyrrolidone.

In one example, the fibrous structure and/or fibrous structure product of the present invention comprises a plurality of particles and a plurality of fibrous elements, for example filaments, at a weight ratio of particles to fibrous elements of from about 3:1 to about 20:1 and/or from about 5:1 to about 15:1 and/or from about 5:1 to about 12:1 and/or from about 7:1 to about 12:1.

Method for Making Fibrous Structures

Figure 7:
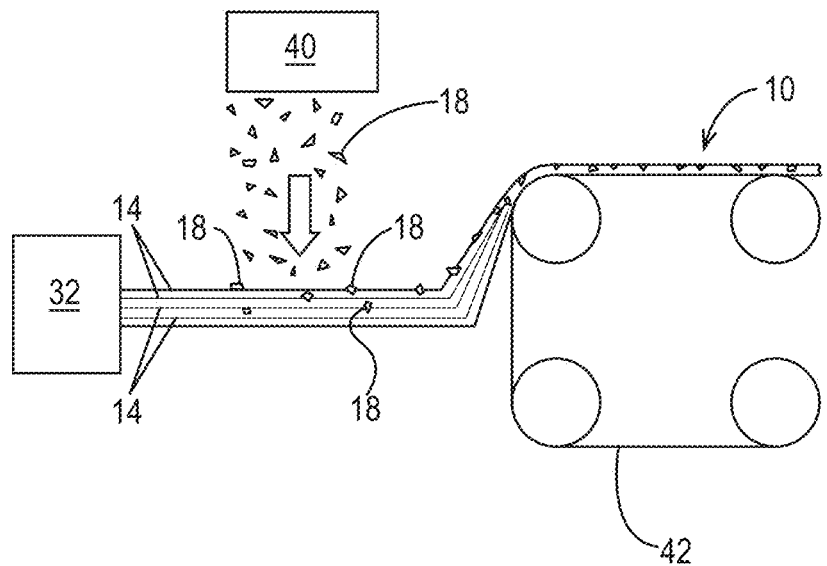
FIG. 7 is a schematic representation of an example of a process for making a fibrous structure according to the present invention.

In one example of the present invention, as shown in FIG. 7, a fibrous structure 10 of the present invention may be made by spinning a fibrous element-forming composition 30 from a spinning die 32, as described in FIGS. 5 and 6, to form a plurality of fibrous elements 14, for example a plurality of natural polymer-based fibrous elements, such as filaments, and then associating one or more particles 18 provided by a particle source 40, for example a sifter or an airlaid forming head. The particles 18 may be dispersed within the fibrous elements 14. The mixture of particles 18 and fibrous elements 14, may be collected on a collection belt 42, such as a patterned collection belt that imparts a texture, such as a three-dimensional texture to at least one surface of the fibrous structure 10.

Figure 8:
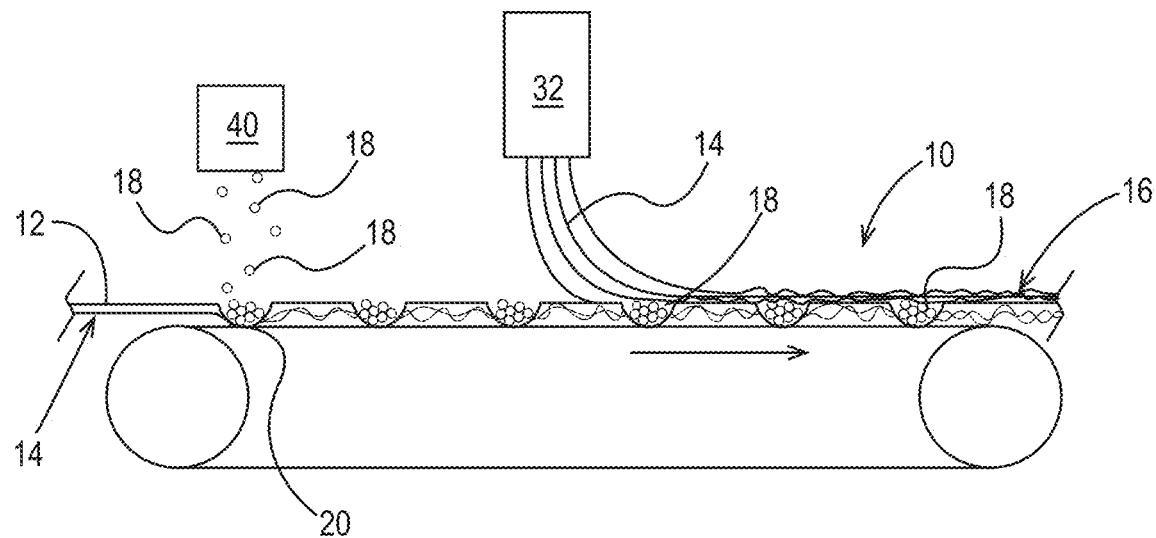
FIG. 8 is a schematic representation of another example of a process for making a fibrous structure according to the present invention.

FIG. 8 illustrates another example of a method for making a fibrous structure 10 according to FIG. 2. The method comprises the steps of forming a first layer 12 of a plurality of fibrous elements 14 such that pockets 20 are formed in a surface of the first layer 12. One or more particles 18 are deposited into the pockets 20 from a particle source 40. A second layer 16 comprising a plurality of fibrous elements 14 produced from a spinning die 32 are then formed on the surface of the first layer 12 such that the particles 18 are entrapped in the pockets 20.

Figure 9:
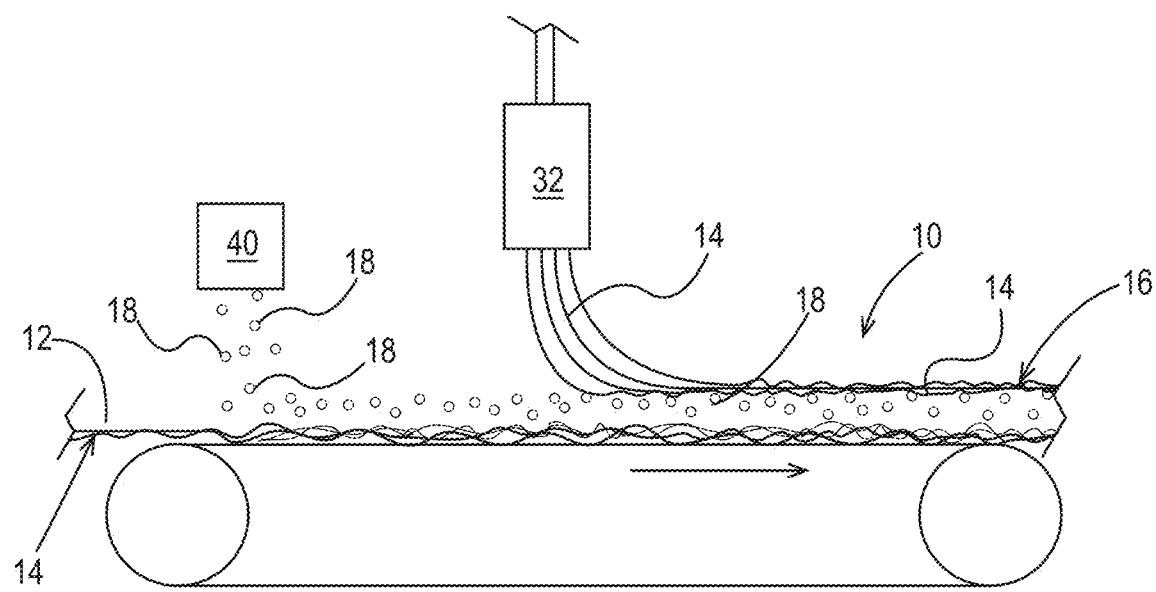
FIG. 9 is a schematic representation of another example of a process for making a fibrous structure according to the present invention.

FIG. 9 illustrates yet another example of a method for making a fibrous structure 10 according to FIG. 1. The method comprises the steps of forming a first layer 12 of a plurality of fibrous elements 14. One or more particles 18 are deposited onto a surface of the first layer 12 from a particle source 40. A second layer 16 comprising a plurality of fibrous elements 14 produced from a spinning die 32 are then formed on top of the particles 18 such that the particles 18 are positioned between the first layer 12 and the second layer 16.

Non-Limiting Example for Making Fibrous Structures

The addition of particles may be accomplished during the formation of the embryonic fibers or after collection of the embryonic fibers on the patterned belts. Disclosed are three methods involving the addition of particulates resulting in said particulates being entrapped in the structure As shown in FIGS. 5 and 6, the fibrous elements 14 of the present invention may be made as follows. Fibrous elements 14 may be formed by means of a small-scale apparatus, a schematic representation of which is shown in FIGS. 5 and 6. A pressurized tank 44, suitable for batch operation is filled with a suitable fibrous element-forming composition 30 for spinning. A pump 46, such as a Zenith®, type PEP II, having a capacity of 5.0 cubic centimeters per revolution (cc/rev), manufactured by Parker Hannifin Corporation, Zenith Pumps division, of Sanford, N.C., USA may be used to facilitate transport of the fibrous element-forming composition to a spinning die 32. The flow of the fibrous element-forming composition 30 comprising a fibrous element-forming material, for example a fibrous element-forming from the pressurized tank 44 to the spinning die 32 may be controlled by adjusting the number of revolutions per minute (rpm) of the pump 46. Pipes 48 may be used to connect the pressurized tank 44, the pump 46, and the spinning die 32.

The spinning die 32 shown in FIG. 6 has several rows of circular extrusion nozzles (fibrous element-forming holes 34) spaced from one another at a pitch P of about 1.524 millimeters (about 0.060 inches). The nozzles have individual inner diameters of about 0.305 millimeters (about 0.012 inches) and individual outside diameters of about 0.813 millimeters (about 0.032 inches). Each individual nozzle is encircled by an annular and divergently flared orifice (concentric attenuation fluid hole 38 to supply attenuation air to each individual melt capillary 36 (a "multi-row capillary die"). The filament-forming composition 30 extruded through the nozzles is surrounded and attenuated by generally cylindrical, humidified air streams supplied through the orifices.

Attenuation air can be provided by heating compressed air from a source by an electrical-resistance heater, for example, a heater manufactured by Chromalox, Division of Emerson Electric, of Pittsburgh, Pa., USA. An appropriate quantity of steam was added to saturate or nearly saturate the heated air at the conditions in the electrically heated, thermostatically controlled delivery pipe. Condensate was removed in an electrically heated, thermostatically controlled, separator.

The embryonic fibrous element are dried by a drying air stream having a temperature from about 149° C. (about 300° F.) to about 315° C. (about 600° F.) by an electrical resistance heater (not shown) supplied through drying nozzles and discharged at an angle of about 90 degrees relative to the general orientation of the non-thermoplastic embryonic fibers being extruded. The dried embryonic fibrous elements are collected on a collection device, such as, for example, a movable foraminous belt or patterned collection belt. The addition of a vacuum source directly under the formation zone may be used to aid collection of the fibers.

A particle source 40, for example a feeder, suitable to supply a flow of particles 18 may be placed directly above the drying region for the fibrous elements 14 as shown in FIG. 7. In this case a vibratory feeder made by Retsch® of Haan, Germany, is used. In order to aid in a consistent distribution of particles in the cross direction the particles are fed onto a tray that started off the width of the feeder and ended at the same width as the spinning die face to ensure particles were delivered into all areas of fibrous element formation. The tray is completely enclosed with the exception of the exit to minimize disruption of the particle feed.

While embryonic fibrous elements are being formed, the feeder is turned on and particles are introduced into the fibrous element stream. In this case, Green Zero (Green Speckle Granules) manufactured by Genencor International® of Leiden, The Netherlands is used as the particles. The particles associated and/or mixed with the fibrous elements and are collected together on the collecting belt.

Once the precursor fibrous structure has been formed, the precursor fibrous structure may be subjected to an aperturing process; namely, a process that imparts one or more apertures to the fibrous structure to produce an apertured fibrous structure. Non-limiting examples of such aperturing processes include embossing, rodding, rotary knife aperturing, pinning, die cutting, die punching, needlepunching, knurling, pneumatic forming, hydraulic forming, laser cutting, and tufting.

In one example, a precursor fibrous structure is subjected to a rotary knife aperturing operation as generally described in U.S. Pat. No. 8,679,391. In another example, the precursor fibrous structure is subjected to a pinning operation as described below. In one example, the precursor fibrous structure is passed through a nip that is formed between two opposing pin rollers of arranged in an intermeshing configuration so that pins from one roller pass through the space between pins on the opposing roller in the nip. A typical configurations may employ two rollers with the same pin design and arrangement. However, the opposing roller may be of a different pin design and arrangement, may instead not have pins, but other fibrous structure support members, or may be a solid surface comprised of a compliant material allowing for interference between the pins of the pinned roller and the compliant surface. The degree of interference between the virtual cylinders described by the tips of the pins is described as the Depth of Engagement. As the fibrous structure passes through the nip formed between the opposing rollers, the pins from each pinned roller engage with and penetrate the fibrous structure to a depth determined largely by the depth of engagement between the rollers and the nominal thickness of the fibrous structure.

Figure 10A:
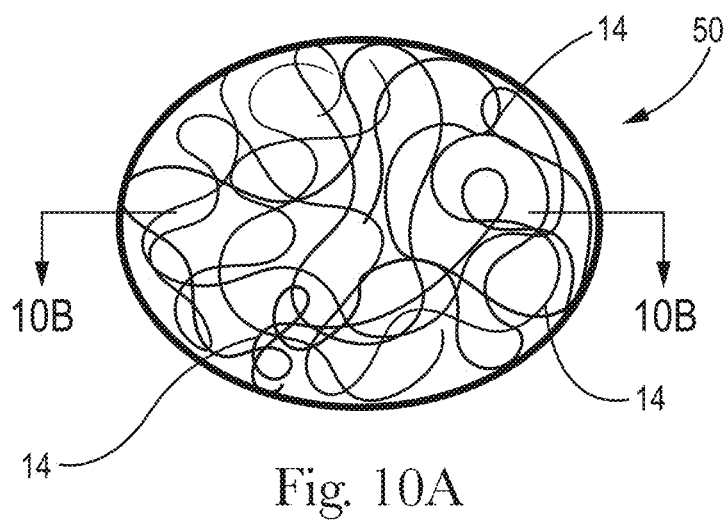
FIG. 10A is a schematic representation of an example of a foaming fibrous structure product according to the present invention.
Figure 10B:
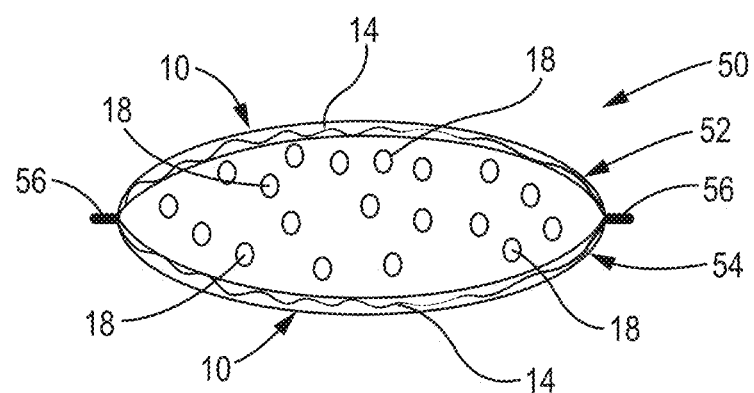
FIG. 10B is a cross-sectional view taken along line 10B-10B of FIG. 10A.

An example of a fibrous structure product 50, for example a usable unit that a consumer would use for its intended purpose, is shown in FIGS. 10A and 10B. As shown in FIG. 10A and FIG. 10B, in one example, a fibrous structure product 50 comprises a multi-ply fibrous structure comprising one or more, in this case two plies of fibrous structure 10 (a first fibrous structure ply 52 and a second fibrous structure ply 54), which themselves may or may not be fibrous structures, but are components of a fibrous structure product 50, that are associated with one another to form the multi-ply fibrous structure. In one example as shown in FIG. 10B, the fibrous structures 10 comprise a plurality of fibrous elements 14 comprising a natural polymer-based fibrous element-forming material, such as a modified polysaccharide, and an active agent comprising a surfactant or surfactant mixture present within the fibrous elements 14. A plurality of particles 18, for example water-soluble active agent-containing particles, such as agglomerates, comprising for example a surfactant, are positioned between (sandwiched between) the two fibrous structures 10. The two plies of fibrous structure 10 (the first and second fibrous structure plies 52, 54) may be bonded at their edges by an edge seam 56, which may be formed by compressing the two plies of fibrous structure 10 together along their edges to form a pouch that contains the particles 18 until at least partial dissolution of the multi-ply fibrous structure or one or more of the plies of the fibrous structure 10 occurs during use.

In one example, the fibrous structures may independently exhibit any suitable basis weight, for example from about 100 gsm to about 5000 gsm and/or from about 250 gsm to about 3000 gsm and/or from about 500 gsm to about 2000 gsm. In one example, the fibrous elements within the fibrous structures may independently be present in the fibrous structures at any suitable basis weight, for example from about 10 to about 1000 gsm and/or from about 10 gsm to about 500 gsm and/or from about 20 gsm to about 400 gsm and/or from about 100 gsm to about 300 gsm. In one example, the particles, when present within the fibrous structures may independently be present in the fibrous structures at any suitable basis weight, for example from about 100 gsm to about 4000 gsm and/or from about 250 gsm to about 3000 gsm and/or from about 500 gsm to about 2000 gsm.

In one example, other particles comprising other active agents may be added to the fibrous structures and/or between the fibrous structures. For example, a perfume may be positioned between the two fibrous structures before associating the fibrous structures together. In one example, the fibrous structures of the present invention are void or substantially void (doesn't negatively impact the foam generation by the fibrous structures) of suds suppressing agents and similar active agents that prevent and/or inhibit foam generation.

In one example, the method for making a fibrous structure of the present invention comprises the steps of:
a. providing a fibrous element-forming composition comprising one or more fibrous element-forming materials, for example natural polymer-based fibrous element-forming materials comprising a modified polysaccharide and one or more active agents wherein at least one of the active agents comprises a surfactant or surfactant mixture, wherein the surfactant or surfactant mixture and the modified polysaccharide are present within the fibrous element-forming composition at a weight ratio of from about 0.25:1 to about 5:1;
b. spinning the fibrous element-forming composition into a plurality of fibrous elements comprising the modified polysaccharide and the surfactant or surfactant mixture; and
c. collecting the plurality of fibrous elements to form a fibrous structure, for example on a collection device, such as a belt.

In one example, the method for making a fibrous structure of the present invention further comprises the step of cutting one or more articles of manufacture from the fibrous structure, for example die cutting one or more articles of manufacture from the fibrous structure.

In one example, the method for making a fibrous structure of the present invention further comprises the step of packaging one or more of the articles of manufacture into a package.

In one example, the package comprises one or more fibrous structures of the present invention.

In one example, the package comprises one or more articles of manufacture of the present invention.

In one example, the packaging material of the present invention is substantially natural and/or naturally derived and/or biosourced and/or recyclable and/or exhibits a biodegradability as determined by the OECD 301B Ready Biodegradability $CO_2$ Evolution Test Method of at least 5% and/or at least 10% and/or at least 15% and/or at least 20% and/or at least 25% and/or at least 30% and/or at least 35% and/or at least 40% and/or at least 45% and/or at least 50% and/or at least 55% and/or about 60% and/or at least 5% to about 60% on the $60^{th}$ day of the test duration and/or exhibits a biodegradability as determined by the OECD 301B Ready Biodegradability$CO_2$ Evolution Test Method of at least 5% and/or at least 10% and/or at least 15% and/or at least 20% and/or at least 25% and/or at least 30% and/or at least 35% and/or at least 40% and/or at least 45% and/or at least 50% and/or at least 55% and/or at least 60% and/or at least 65% and/or at least 70% and/or at least 75% and/or about 80% and/or at least 5% to about 80% on the $90^{th}$ day of the test duration.

Test Methods

Unless otherwise specified, all tests described herein including those described under the Definitions section and the following test methods are conducted on samples that have been conditioned in a conditioned room at a temperature of 23° C.±1.0° C. and a relative humidity of 50%±2% for a minimum of 2 hours prior to the test. The samples tested are "usable units." "Usable units" as used herein means articles, for example unit dose articles/products, used by consumers for their intended purpose. All tests are conducted under the same environmental conditions and in such conditioned room. Do not test samples that have defects such as wrinkles, tears and like. Samples conditioned as described herein are considered dry samples (such as "dry filaments") for testing purposes. All instruments are calibrated according to manufacturer's specifications.

Basis Weight Test Method

Basis weight is defined as the weight in $g/m^2$ of a sample being tested. It is determined by accurately weighing a known area of a conditioned sample using an appropriate balance, recording the weight and area of sample tested, applying the appropriate conversion factors, and finally calculating the basis weight in $g/m^2$ of the sample.

Basis weight is measured by cutting a sample from a single web, a stack of webs, or other appropriate plied up, or consumer salable unit and weighing the sample using a top loading analytical balance with a resolution of ±0.001 g. The sample must be equilibrated at a temperature of 73°±2° F. (23°±1° C.) and a relative humidity of 50% (±2%) for a minimum of two hours prior to cutting samples. During weighing, the balance is protected from air drafts and other disturbances using a draft shield. A precision cutting die, measuring 1.625×1.625 in (41.275×41.275 mm) is used to prepare all samples. Select usable sample areas which are clean, free of holes, tears, wrinkles and other defects.

For each sample use the die cutter described above to cut a sample, weigh the mass of the sample, and record the mass result to the nearest 0.001 g.

The Basis Weight is calculated in $g/m^2$ as follows:

Basis Weight=(Mass of sample)/(Area of sample).

Or specifically,

Basis Weight $(g/m^2)$=(Mass of sample (g))/(0.001704 $m^2$).

Report result to the nearest 0.1 $g/m^2$. Sample dimensions can be changed or varied using a similar precision cutter as mentioned above. If the sample dimension is decreased, then several samples should be measured and the mean value reported as its basis weight.

Water Content Test Method

The water (moisture) content present in a fibrous element and/or particle and/or fibrous structure is measured using the following Water Content Test Method. A fibrous element and/or particle and/or fibrous structure or portion thereof ("sample") in the form of a pre-cut sheet is placed in a conditioned room at a temperature of 23° C.±1.0° C. and a relative humidity of 50%±2% for at least 24 hours prior to testing. Each fibrous structure sample has an area of at least 4 square inches, but small enough in size to fit appropriately on the balance weighing plate. Under the temperature and humidity conditions mentioned above, using a balance with at least four decimal places, the weight of the sample is recorded every five minutes until a change of less than 0.5% of previous weight is detected during a 10 minute period. The final weight is recorded as the "equilibrium weight". Within 10 minutes, the samples are placed into the forced air oven on top of foil for 24 hours at 70° C.±2° C. at a relative humidity of 4%±2% for drying. After the 24 hours of drying, the sample is removed and weighed within 15 seconds. This weight is designated as the "dry weight" of the sample.

The water (moisture) content of the sample is calculated as follows:

$$\% \text{ Water in sample} = 100\% \times \frac{(\text{Equilibrium weight of sample} - \text{Dry weight of sample})}{\text{Dry weight of sample}}$$

The % Water (moisture) in sample for 3 replicates is averaged to give the reported % Water (moisture) in sample. Report results to the nearest 0.1%.

Diameter Test Method

The diameter of a discrete fibrous element or a fibrous element within a fibrous structure is determined by using a Scanning Electron Microscope (SEM) or an Optical Microscope and an image analysis software. A magnification of 200 to 10,000 times is chosen such that the fibrous elements are suitably enlarged for measurement. When using the SEM, the samples are sputtered with gold or a palladium compound to avoid electric charging and vibrations of the fibrous element in the electron beam. A manual procedure for determining the fibrous element diameters is used from the image (on monitor screen) taken with the SEM or the optical microscope. Using a mouse and a cursor tool, the edge of a randomly selected fibrous element is sought and then measured across its width (i.e., perpendicular to fibrous element direction at that point) to the other edge of the fibrous element. A scaled and calibrated image analysis tool provides the scaling to get actual reading in µm. For fibrous elements within a fibrous structure, several fibrous element are randomly selected across the sample of the fibrous structure using the SEM or the optical microscope. At least two portions of the fibrous structure are cut and tested in this manner Altogether at least 100 such measurements are made and then all data are recorded for statistical analysis. The recorded data are used to calculate average (mean) of the fibrous element diameters, standard deviation of the fibrous element diameters, and median of the fibrous element diameters.

Another useful statistic is the calculation of the amount of the population of fibrous elements that is below a certain upper limit. To determine this statistic, the software is programmed to count how many results of the fibrous element diameters are below an upper limit and that count (divided by total number of data and multiplied by 100%) is reported in percent as percent below the upper limit, such as percent below 1 micrometer diameter or %-submicron, for example. We denote the measured diameter (in µm) of an individual circular fibrous element as di.

In the case that the fibrous elements have non-circular cross-sections, the measurement of the fibrous element diameter is determined as and set equal to the hydraulic diameter which is four times the cross-sectional area of the fibrous element divided by the perimeter of the cross-section of the fibrous element (outer perimeter in case of hollow fibrous elements). The number-average diameter, alternatively average diameter is calculated as:

$$d_{num} = \frac{\sum_{i=1}^{n} d_i}{n}$$

Weight Average Molecular Weight

The Mw and Mw distribution of materials, for example fibrous element-forming materials, for example modified polysaccharides, such as modified starches, for example starch acetates are analyzed by GPC-MALS (Gel Permeation Chromatography combined with Multi Angle Light Scattering). An analysis of a fibrous element-forming material sample is conducted by dissolving the fibrous element-forming material in DMSO with 0.1% LiBr. The fibrous element-forming material solution is then separated and analyzed on a set of 3 StyraGel HT columns from Waters Corporation using separation module 2695e or equivalent from Waters Corporation in combination with a laser photometer, DAWN HELEOS, 658 nm or equivalent from Wyatt Technology and a refractive index detector 2414 or equivalent from Waters Corporation. In the case of starch acetate samples they were saponified with 1N NaOH solution at 40° C. Then the samples were precipitated in MeOH, washed and dried gently. The Mw is reported as g/mol.

Fibrous Element-Forming Material Miscibility Test Method

A fibrous element-forming material, for example a natural polymer-based fibrous element-forming material, for example modified polysaccharide, such as a modified starch, for example acetylated starch (starch acetate) is cooked out in deionized water at 95° C. and cooled to 80° C. to form a fibrous element-forming material solution. A surfactant paste (sodium linear alkylbenzene sulfonate (NaLAS) at 30% solids) is added to the fibrous element-forming material solution with a surfactant to fibrous element-forming material weight ratio of 2:1. The surfactant/fibrous element-forming material solution is then stirred for 15 minutes after which the solution is placed in an oven at 80° C. overnight. The solution is then put into a 15 mL vial and a visual inspection is performed to determine whether the solution exhibits a single phase (1 phase or transparent/no phase separation), which satisfies this test method (sufficient miscibility=suitable) or if phase separation occurs (2 phase), which does not satisfy this test method (insufficient miscibility=not suitable).

Dissolution Test Method

Figure 13:
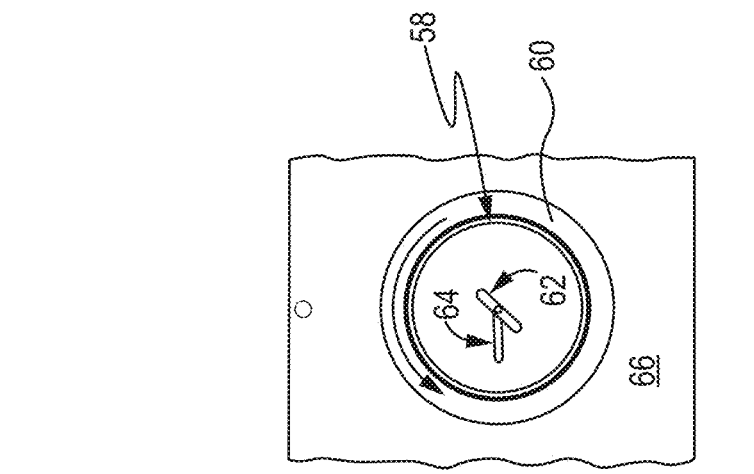
FIG. 13 is a schematic representation of a top view of FIG. 12.
Figure 12:
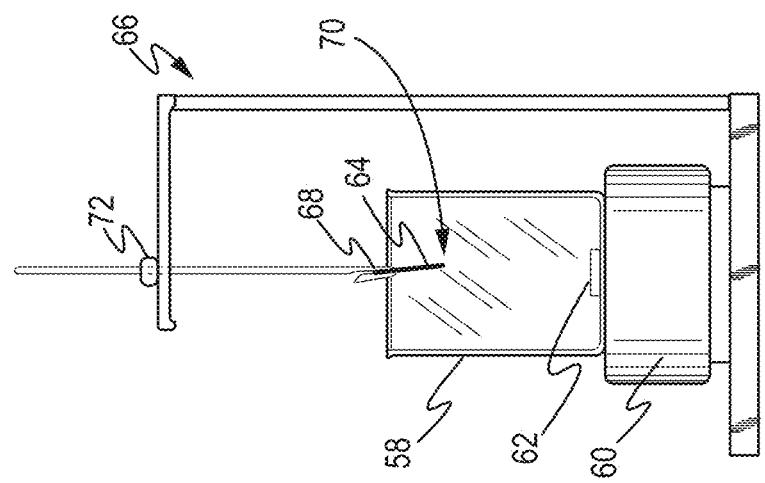
FIG. 12 is a schematic representation of FIG. 11 during the operation of the dissolution test.
Figure 11:
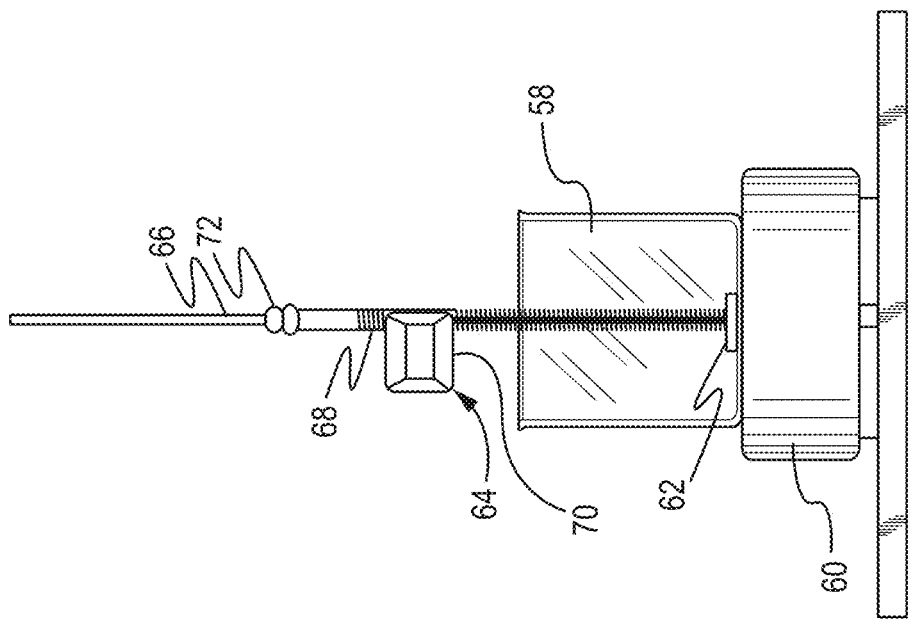
FIG. 11 is a schematic representation of an example of a setup of equipment used in measuring dissolution according to the present invention.

Apparatus and Materials (Also, See FIGS. 11 Through 13):
  600 mL Beaker 58
  Magnetic Stirrer 60 (Labline Model No. 1250 or equivalent)
  Magnetic Stirring Rod 62 (5 cm)
  Thermometer (1 to 100° C.+/−1° C.)
  Cutting Die—Stainless Steel cutting die with dimensions 3.8 cm×3.2 cm
  Timer (0-3,600 seconds or 1 hour), accurate to the nearest second. Timer used should have sufficient total time measurement range if sample exhibits dissolution time greater than 3,600 seconds. However, timer needs to be accurate to the nearest second.
  Polaroid 35 mm Slide Mount 64 (commercially available from Polaroid Corporation or equivalent)–)
  35 mm Slide Mount Holder 66 (or equivalent)
  City of Cincinnati Water or equivalent having the following properties: Total Hardness=155 mg/L as $CaCO_3$; Calcium content=33.2 mg/L; Magnesium content=17.5 mg/L; Phosphate content=0.0462.

Test Protocol

Equilibrate samples in constant temperature and humidity environment of 23° C.±1.0° C. and 50% RH±2% for at least 2 hours. Measure the basis weight of the fibrous structure sample to be measured using Basis Weight Test Method defined herein. Cut three dissolution test specimens from the fibrous structure sample using cutting die (3.8 cm×3.2 cm), so it fits within the 35 mm Slide Mount 64, which has an open area dimensions 24×36 mm Lock each specimen in a separate 35 mm slide mount 64. Place magnetic stirring rod 62 into the 600 mL beaker 58. Turn on the city water tap flow (or equivalent) and measure water temperature with thermometer and, if necessary, adjust the hot or cold water to maintain it at the testing temperature. Testing temperature is 15° C.±1° C. water. Once at testing temperature, fill beaker 58 with 500 mL±5 mL of the 15° C.±1° C. city water. Place full beaker 58 on magnetic stirrer 60, turn on stirrer 62, and adjust stir speed until a vortex develops and the bottom of the vortex is at the 400 mL mark on the beaker 58. Secure the 35 mm slide mount 64 in the alligator clamp 68 of the 35 mm slide mount holder 66 such that the long end 70 of the slide mount 64 is parallel to the water surface. The alligator clamp 68 should be positioned in the middle of the long end 70 of the slide mount 64. The depth adjuster 72 of the holder 66 should be set so that the distance between the bottom of the depth adjuster 72 and the bottom of the alligator clip 68 is ~11+/−0.125 inches. This set up will position the sample surface perpendicular to the flow of the water. In one motion, drop the secured slide and clamp into the water and start the timer. The sample is dropped so that the sample is centered in the beaker. Disintegration occurs when the nonwoven structure breaks apart. Record this as the disintegration time. When all of the visible nonwoven structure is released from the slide mount, raise the slide out of the water while continuing the monitor the solution for undissolved nonwoven structure fragments. Dissolution occurs when all nonwoven structure fragments are no longer visible. Record this as the dissolution time.

Three replicates of each sample are run and the average disintegration and dissolution times are recorded. Average disintegration and dissolution times are in units of seconds.

The average disintegration and dissolution times are normalized for basis weight by dividing each by the sample basis weight as determined by the Basis Weight Method defined herein. Basis weight normalized disintegration and dissolution times are in units of seconds/gsm of sample $(s/(g/m^2))$.

Thickness Method

Thickness of a fibrous structure is measured by cutting 5 samples of a fibrous structure sample such that each cut sample is larger in size than a load foot loading surface of a VIR Electronic Thickness Tester Model II available from Thwing-Albert Instrument Company, Philadelphia, PA. Typically, the load foot loading surface has a circular surface area of about 3.14 in$^2$. The sample is confined between a horizontal flat surface and the load foot loading surface. The load foot loading surface applies a confining pressure to the sample of 15.5 g/cm$^2$. The thickness of each sample is the resulting gap between the flat surface and the load foot loading surface. The thickness is calculated as the average thickness of the five samples. The result is reported in millimeters (mm).

Shear Viscosity Test Method

The shear viscosity of a filament-forming composition of the present invention is measured using a capillary rheometer, Goettfert Rheograph 6000, manufactured by Goettfert USA of Rock Hill SC, USA. The measurements are conducted using a capillary die having a diameter D of 1.0 mm and a length L of 30 mm (i.e., L/D=30). The die is attached to the lower end of the rheometer's 20 mm barrel, which is held at a die test temperature of 75° C. A preheated to die test temperature, 60 g sample of the filament-forming composition is loaded into the barrel section of the rheometer. Rid the sample of any entrapped air. Push the sample from the barrel through the capillary die at a set of chosen rates 1,000-10,000 seconds$^{-1}$. An apparent shear viscosity can be calculated with the rheometer's software from the pressure drop the sample experiences as it goes from the barrel through the capillary die and the flow rate of the sample through the capillary die. The log (apparent shear viscosity) can be plotted against log (shear rate) and the plot can be fitted by the power law, according to the formula $\eta = K\gamma^{n-1}$, wherein K is the material's viscosity constant, n is the material's thinning index and $\gamma$ is the shear rate. The reported apparent shear viscosity of the filament-forming composition herein is calculated from an interpolation to a shear rate of 3,000 sec$^{-1}$ using the power law relation.

Rotational Rheometer Test Method

The shear viscosity of the composition is measured using a commercially available AR-G2 rotational rheometer from TA Instruments or similar device. A cone-plate geometry of 40 mm diameter, 2.007° angle, with a truncation gap of 57 mm was used with Peltier plate for temperature control. A stepped-flow shear rate is applied from 0.1/s-100/s with a dwell time of 10 seconds at 25° C. The shear viscosity at 10/s is reported.

Fibrous Element Composition Test Method

In order to prepare fibrous elements for fibrous element composition measurement, the fibrous elements must be conditioned by removing any coating compositions and/or materials present on the external surfaces of the fibrous elements that are removable. An example of a method for doing so is washing the fibrous elements 3 times with a suitable solvent that will remove the external coating while leaving the fibrous elements unaltered. The fibrous elements are then air dried at 23° C.±1.0° C. until the fibrous elements comprise less than 10% moisture. A chemical analysis of the conditioned fibrous elements is then completed to determine the compositional make-up of the fibrous elements with respect to the filament-forming materials and the active agents and the level of the filament-forming materials and active agents present in the fibrous elements.

The compositional make-up of the fibrous elements with respect to the filament-forming material and the active agents can also be determined by completing a cross-section analysis using TOF-SIMs or SEM. Still another method for determining compositional make-up of the fibrous elements uses a fluorescent dye as a marker. In addition, as always, a manufacturer of fibrous elements should know the compositions of their fibrous elements.

Particle Size Distribution Test Method

The particle size distribution test is conducted to determine characteristic sizes of particles, which may be discrete particles, which may be gas bubble-stabilizing agent-coated effervescent acid or salt particles, and/or agglomerates (discrete particles bound together, for example by a gas bubble-stabilizing agent). It is conducted using ASTM D 502-89, "Standard Test Method for Particle Size of Soaps and Other Detergents", approved May 26, 1989, with a further specification for sieve sizes and sieve time used in the analysis. Following section 7, "Procedure using machine-sieving method," a nest of clean dry sieves containing U.S. Standard (ASTM E 11) sieves #4 (4.75 mm), #6 (3.35 mm), #8 (2.36 mm), #12 (1.7 mm), #16 (1.18 mm), #20 (850 micrometer), #30 (600 micrometer), #40 (425 micrometer), #50 (300 micrometer), #70 (212 micrometer), #100 (150 micrometer), #170 (90 micrometer), #325 (44 micrometer) and pan is required to cover the range of particle sizes referenced herein. The prescribed Machine-Sieving Method is used with the above sieve nest. A suitable sieve-shaking machine can be obtained from W.S. Tyler Company, Ohio, U.S.A. The sieve-shaking test sample is approximately 100 grams and is shaken for 5 minutes.

The data are plotted on a semi-log plot with the micrometer size opening of each sieve plotted on the logarithmic abscissa and the cumulative mass percent finer (CMPF) is plotted on the linear ordinate. An example of the above data representation is given in ISO 9276-1:1998, "Representation of results of particle size analysis—Part 1: Graphical Representation", Figure A.4. A characteristic particle size (Dx, x=10, 50,90), for the purpose of this invention, is defined as the abscissa value at the point where the cumulative mass percent is equal to x percent, and is calculated by a straight line interpolation between the data points directly above (a) and below (b) the x value using the following equation:

$$Dx=10^{[Log(Da)-(Log(Da)-Log(db))*(Qa-x\%)/(Qa-Qb)]}$$

where Log is the base 10 logarithm, Qa and Qb are the cumulative mass percentile values of the measured data immediately above and below the $x^{th}$ percentile, respectively; and Da and db are the micrometer sieve size values corresponding to these data.

Example Data and Calculations:

| sieve size (micrometer) | weight on sieve (g) | cumulative mass % finer (CMPF) |
|---|---|---|
| 1700 | 0 | 100% |
| 1180 | 0.68 | 99.3% |
| 850 | 10.40 | 89.0% |
| 600 | 28.73 | 60.3% |
| 425 | 27.97 | 32.4% |
| 300 | 17.20 | 15.2% |
| 212 | 8.42 | 6.8% |
| 150 | 4.00 | 2.8% |
| Pan | 2.84 | 0.0% |

For D10 (x=10), the micrometer screen size where CMPF is immediately above 10% (Da) is 300 micrometer, the screen below (db) is 212 micrometer. The cumulative mass immediately above 10% (Qa) is 15.2%, below (Qb) is 6.8%. D10=10^[Log(300)−(Log(300)−Log(212))*(15.2%−10%)/(15.2%−6.8%)]=242 micrometer.

For D90 (x=90), the micrometer screen size where CMPF is immediately above 90% (Da) is 1180 micrometer, the screen below (db) is 850 micrometer. The cumulative mass immediately above 90% (Qa) is 99.3%, below (Qb) is 89.0%. D90=10^[Log(1180)−(Log(1180)−Log(850))*(99.3%−90%)/(99.3%−89.0%)]=878 micrometer.

For D50 (x=50), the micrometer screen size where CMPF is immediately above 50% (Da) is 600 micrometer, the screen below (db) is 425 micrometer. The cumulative mass immediately above 50% (Qa) is 60.3%, below (Qb) is 32.4%. D50=10^[Log(600)−(Log(600)−Log(425))*(60.3%−50%)/(60.3%−32.4%)]=528 micrometer.

Fedors Method

The solubility parameter numbers of natural polymer-based fibrous element-forming materials, for example modified polysaccharides, such as modified starches, for example starch acetates is calculated using the Fedors Method.

The following is an example of calculating solubility parameter numbers for various fibrous element-forming materials.

The solubility parameter can be calculated from Equation 1 in Fedors Method (repeated here as Equation 1).

(Fedors Equation 1)

$$\delta = \left(\frac{\Delta E_v}{V}\right)^{\frac{1}{2}} \quad \text{Equation 1}$$

The values for $\Delta E_v$ and V can be calculated using Equations 24 and 25 in Fedors Method repeated as equation 2 and 3, respectively here:

$\Delta E_v = \Sigma_i \Delta e_i$      (Fedors Equation 24) Equation 2:

$V = \Sigma_i \Delta v_i$      (Fedors Equation 25) Equation 3:

Using values of $\Delta e_i$ and $\Delta v_i$ from Table 5 of Fedors Method, the atomic and group contributions are summed using the homopolymer repeat unit structure for the desired polymer (e.g. modified polysaccharide) ignoring polymer end groups. Since all these polymers have glass transition temperatures above 25° C., a correction in molar volume is necessary (see Equation 26 in Fedors Method) by counting the number (n) of main chain skeletal atoms. Then, for n<3, a correction to $\Delta v_i = 4n$ is used. For modified polysaccharides, the 6 atom cyclic ring structure necessitates both the molar volume correction (using $\Delta v_i = 2n$, since n≥3) and a ring closure adjustment for 5 or more atoms (see Table 5 of Fedors Method).

Examples of this calculation are shown for polyvinyl alcohol, poly vinyl acetate, starch, and starch acetate (with DS=1).

Polyvinyl alcohol —(CH$_2$—CH(OH))—

| Group | Number of Groups in Repeat Unit | $\Delta e_i$, cal/mole | $\Delta v_i$, cal/mole |
|---|---|---|---|
| CH$_2$ | 1 | 1180 | 16.1 |
| CH | 1 | 820 | −1 |
| OH | 1 | 7120 | 10 |
| Molar volume correction; main chain skeletal atoms = 2; $\Delta v_i = 4n$ | | | 8 |
| Sum | | 9120 | 33.1 |
| $\delta = \left(\frac{\Delta E_v}{V}\right)^{\frac{1}{2}} =$ | | d = 16.5991 | |

Polyvinyl acetate —(CH$_2$—CH(OOCCH$_3$))—

| Group | Number of Groups in Repeat Unit | $\Delta e_i$, cal/mole | $\Delta v_i$, cal/mole |
|---|---|---|---|
| CH$_2$ | 1 | 1180 | 16.1 |
| CH | 1 | 820 | −1 |
| COO | 1 | 4300 | 18 |
| CH$_3$ | 1 | 1125 | 33.5 |
| Molar volume correction; main chain skeletal atoms n = 2; $\Delta v_i = 4n$ | | | 8 |
| Sum | | 7425 | 74.6 |
| $\delta = \left(\frac{\Delta E_v}{V}\right)^{\frac{1}{2}} =$ | | d = 9.97651 | |

Starch

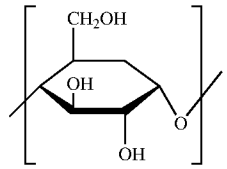

| Group | Number of Groups in Repeat Unit | $\Delta e_i$, cal/mole | $\Delta v_i$, cal/mole |
|---|---|---|---|
| CH | 5 | 4100 | −5 |
| CH$_2$ | 1 | 1180 | 16.1 |
| OH (adjacent carbons) | 2 | 10440 | 26 |
| OH | 1 | 7120 | 10 |
| O | 2 | 1600 | 7.6 |
| Ring Closure (5 or more atoms) | 1 | 250 | 16 |
| Molar volume correction; main chain skeletal atoms n = 6; $\Delta v_i = 2n$ | | | 12 |
| Sum | | 24690 | 82.7 |
| $\delta = \left(\dfrac{\Delta E_v}{V}\right)^{\frac{1}{2}} =$ | | d = 17.2786 | |

Starch Acetate (with DS=1)

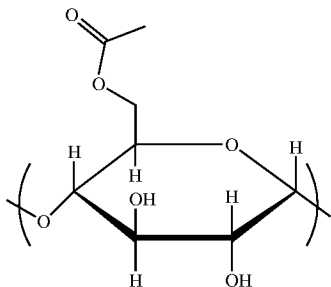

| Group | Number of Groups in Repeat Unit | $\Delta e_i$, cal/mole | $\Delta v_i$, cal/mole |
|---|---|---|---|
| CH | 5 | 4100 | −5 |
| CH$_2$ | 1 | 1180 | 16.1 |
| OH (adjacent carbons) | 2 | 10440 | 26 |
| O | 2 | 1600 | 7.6 |
| COO | 1 | 4300 | 18 |
| CH$_3$ | 1 | 1125 | 33.5 |
| Ring Closure (5 or more atoms) | 1 | 250 | 16 |
| Molar volume correction; main chain skeletal atoms n = 6; $\Delta v_i = 2n$ | | | 12 |
| Sum | | 22995 | 124.2 |
| $\delta = \left(\dfrac{\Delta E_v}{V}\right)^{\frac{1}{2}} =$ | | d = 13.6068 | |

Copolymer solubility parameters are calculated by summing the mole fraction weighted homopolymer solubility parameters as shown in Equation 4:

$$\delta_{copolymer} = X_A \delta_A + X_B \delta_B \qquad \text{Equation 4:}$$

Where $X_A$ and $\delta_A$ are the mole fraction and homopolymer solubility parameter of homopolymer A, respectively, and $X_B$ and $\delta_B$ are the mole fraction and homopolymer solubility parameter of homopolymer B, respectively, such that the sum of mole fractions equals 1. If an additional termonomer was added, an additional term for the mole fraction and homopolymer solubility parameter would be added to the equation, such that the sum of all mole fractions equals 1.

| Copolymer | Homopolymer A Mole lfraction ($X_A$) | Homopolymer A Solubility Parameter ($\delta_A$) | Homopolymer B Mole fraction ($X_B$) | Homopolymer B Solubility Parameter ($\delta_B$) | Copolymer Solubility Parameter ($\delta$copolymer) |
|---|---|---|---|---|---|
| Poly vinyl alcohol with degree of hydrolysis equal to 80% | 0.80 | 16.5991 | 0.20 | 9.97651 | 15.275 |
| Poly vinyl alcohol with degree of hydrolysis equal to 88% | 0.88 | 16.5991 | 0.12 | 9.97651 | 15.804 |
| Poly vinyl alcohol with degree of hydrolysis equal to 93% | 0.93 | 16.5991 | 0.07 | 9.97651 | 16.136 |
| Starch Acetate (with DS = 0.3) | 0.7 | 17.2786 | 0.3 | 13.6068 | 16.177 |
| Starch Acetate (with DS = 0.5) | 0.5 | 17.2786 | 0.5 | 13.6068 | 15.443 |
| Starch Acetate (with DS = 0.7) | 0.3 | 17.2786 | 0.7 | 13.6068 | 14.708 |

Charge Density Test Method

If one has identified or knows the fibrous element-forming material, for example natural polymer-based fibrous element-forming material in the fibrous element, then the charge density of the fibrous element-forming material can be determined by using a Mutek PCD-04 Particle Charge Detector available from BTG, or equivalent instrument. The following guidelines provided by BTG are used. Clearly, producers of fibrous elements comprising fibrous element-forming materials know what fibrous element-forming materials are being included in their fibrous elements. Therefore, such producers of fibrous elements can determine the charge density of the fibrous element-forming material.

1. Start with a 0.1% solution (0.1 g fibrous element-forming material+99.9 g deionized water). Depending on the titrant consumption increase or decrease fibrous element-forming material content. Solution pH is adjusted prior to final dilution as charge density of many additives is dependent upon solution pH. A pH of 4.5 is used here.

2. Place 20 mL of sample in the PCD measuring cell and insert piston.

3. Put the measuring cell with piston and sample in the PCD, the electrodes are facing the rear. Slide the cell along the guide until it touches the rear.

4. Pull piston upwards and turn it counter-clock-wise to lock the piston in place.

5. Switch on the motor. The streaming potential is shown on the touch panel. Wait 2 minutes until the signal is stable.

6. Use an oppositely charged titrant (for example for a cationic sample having a positive streaming potential: use an anionic titrant). Titrants are available from BTG consisting of 0.001N PVSK or 0.001N PolyDADMAC.

7. An automatic titrator available from BTG is utilized. After selecting the proper titrant, set the titrator to rinse the tubing by dispensing 10 mL insuring that all air bubbles have been purged.

8. Place tubing tip below the surface of the sample and start titration. The automatic titrator is set to stop automatically when the potential reaches 0 mV.

9. Record consumption of titrant, ideally, the consumption of titrant should be 0.2 mL to 10 mL; otherwise decrease or increase fibrous element-forming material content.

10. Repeat titration of a second 20 mL aliquot of the fibrous element-forming material sample.

11. Calculate charge demand (solution) or charge demand (solids);

$$\text{Charge demand } (eq/L) = \frac{V \text{ titrant used } (L) \times \text{Conc. of titrant in Normality } (eq/L)}{\text{Volume of sample titrated } (L)}$$

$$\text{Charge demand } (eq/g) = \frac{V \text{ titrant used } (L) \times \text{Conc. of titrant in Normality } (eq/L)}{\text{Wt. solids of the sample or its active substance } (g)}$$

The charge density (charge demand) of a fibrous element-forming material is reported in meq/g units.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fibrous structure comprising a plurality of fibrous elements,
    wherein the plurality of fibrous elements comprise one or more fibrous element-forming materials wherein at least one of the one or more fibrous element-forming materials comprises a modified polysaccharide and one or more active agents wherein at least one of the active agents comprises a surfactant, wherein the surfactant and the modified polysaccharide are present within the plurality of fibrous elements at a weight ratio of from about 0.15:1 to about 6:1;
    wherein the modified polysaccharide and surfactant fibrous element forming material is miscible as determined by the Fibrous Element-forming Material Miscibility Test Method described herein;
    wherein the modified polysaccharide has a solubility parameter of greater than 14.00 to less than 16.25 as determined according to the Fedors Method; and
    wherein the modified polysaccharide exhibits a weight average molecular weight of greater than 50,000 to less than 40,000,000 g/mol as measured according to the Weight Average Molecular Weight Test Method.

2. The fibrous structure according to claim 1 wherein the plurality of fibrous elements comprises a plurality of filaments.

3. The fibrous structure according to claim 1 wherein the modified polysaccharide is a nonionic modified polysaccharide.

4. The fibrous structure according to claim 1 wherein the modified polysaccharide is derived from starch.

5. The fibrous structure according to claim 4 wherein the acetyl-substituted polysaccharide exhibits a Degree of Substitution (DS) of at least 0.3 to 1.0.

6. The fibrous structure according to claim 1 wherein the modified polysaccharide is derived from starch.

7. The fibrous structure according to claim 1 wherein the plurality of fibrous elements comprise a total level of the modified polysaccharide of less than 80% by weight of the dry fibrous elements and a total level of the surfactant of greater than 20% by weight of the dry fibrous elements.

8. Structure according to claim 1 wherein the modified The fibrous polysaccharide and the surfactant are present in the dry fibrous element at a weight ratio of modified polysaccharide to surfactant of 1 or less.

9. A package comprising one or more fibrous structures according to claim 1.

10. A method for making a fibrous structure according to claim 1, the method comprising the steps of:
    a. providing a fibrous element-forming composition comprising one or more fibrous element-forming materials comprising a modified polysaccharide and one or more active agents wherein at least one of the active agents comprises a surfactant, wherein the surfactant and the modified polysaccharide are present within the fibrous element-forming composition at a weight ratio of from about 0.15:1 to about 6:1;

b. spinning the fibrous element-forming composition into a plurality of fibrous elements comprising the modified polysaccharide and the surfactant; and c. collecting the plurality of fibrous elements to form a fibrous structure.

11. The fibrous structure according to claim 1 wherein the one or more active agents further comprise at least one additional non-surfactant active agent selected from the group consisting of: skin care active agents, medicinal agents, lotions, fabric care active agents, dishwashing active agents, carpet care active agents, surface care active agents, hair care active agents, air care active agents, tooth care active agents, and mixtures thereof.

12. The fibrous structure according to claim 1 wherein the modified polysaccharide exhibits a biodegradability as determined by the OECD 301B Ready Biodegradability$CO_2$ Evolution Test Method of at least 5% on the $28^{th}$ day of the test duration.

\* \* \* \* \*